US008012487B2

(12) United States Patent
Ben-Nun et al.

(10) Patent No.: US 8,012,487 B2
(45) Date of Patent: Sep. 6, 2011

(54) SYNTHETIC PEPTIDES AND DNA SEQUENCES FOR TREATMENT OF MULTIPLE SCLEROSIS

(75) Inventors: Avraham Ben-Nun, Yavne (IL); Nicole Kerlero De Rosbo, Rehovot (IL)

(73) Assignee: Avraham Ben-Nun, Yavne (IL)

( * ) Notice: Subject to any disclaimer, the term of this patent is extended or adjusted under 35 U.S.C. 154(b) by 648 days.

(21) Appl. No.: 10/492,794

(22) PCT Filed: Oct. 17, 2002

(86) PCT No.: PCT/IL02/00837
§ 371 (c)(1),
(2), (4) Date: Apr. 16, 2004

(87) PCT Pub. No.: WO03/033645
PCT Pub. Date: Apr. 24, 2003

(65) Prior Publication Data
US 2005/0037422 A1 Feb. 17, 2005

(30) Foreign Application Priority Data
Oct. 17, 2001 (IL) .......................................... 146016

(51) Int. Cl.
A61K 39/00 (2006.01)
(52) U.S. Cl. .................................................. 424/185.1
(58) Field of Classification Search .................. None
See application file for complete search history.

(56) References Cited

FOREIGN PATENT DOCUMENTS
WO 9634622 A 11/1996
WO WO 01/31037 A2 5/2001

OTHER PUBLICATIONS

Marketletter, Marketletter Pubs (UK), Sep. 13, 1999.*
Anderton, S.M., et al. J. Immunol. 1998;161:3357-3364.*
Anderton, S.M. Immunology. 2001;104:367-376.*
Dong, V.M., et al. Ped. Transplant. 1998;161:181-189.*
Elliott et al., Treatment of experimental encephalomyelitis with a novel chimeric fusion protein of myelin basic protein and proteolipid protein, *The Journal of Clinical Investigation*, 98(7):1602-1612 (Oct. 1996).
Karin et al., Short peptide-based tolerogens without self-antigenic or pathogenic activity reverse autoimmune disease, *The Journal of Immunology*, 160:5188-5194 (1998).
Leadbetter et al., Experimental autoimmune encephalomyelitis induced with a combination of myelin basic protein and myelin oligodendrocyte glycoprotein is ameliorated by administration of a single myelin basic protein peptide, *The Journal of Immunology*, 161:504-512 (1998).
Bielekova, B., et al., "Encephalitogenic Potential of the Myelin Basic Protein (Amino Acids 83-89) in Multiple Sclerosis: Results of a Phase II Clinical Trial With an Altered Peptide Ligand", Nature Medicine, vol. 6, No. 10, pp. 1167-1175 (2000).
Crowe, P. D., et al., "NBI-5788, An Altered MBP83-99 Peptide, Induces a T-Helper 2-Like Immune Response in Multiple Sclerosis Patients", Annals of Neurology, vol. 48, No. 5, pp. 758-765 (2000).
Falk, K. et al., "Induction and Suppression of an Autoimmune Disease by Oligomerized T cell Epitopes: Enhanced in vivo Potency of Encephalitogenic Peptides", Journal of Experimental Medicine, vol. 191, No. 4, pp. 717-730 (2000).
Fridikis-Hareli, M., et al., "Synthetic Peptides that Inhibit Binding of the Myelin Basic Protein 85-99 Epitope to Multiple Sclerosis-Associated HLA-DR2 Molecules and MBP-specific T-cell Responses", Human Immunology, vol. 62, No. 8, pp. 753-763 (2001).
Gaur, A., et al., "Amelioration of Relapsing Experimental Autoimmune Encephalomyelitis With Altered Myelin Basic Protein Peptides Involves Different Cellular Mechanisms", Journal of Neuroimmunology, vol. 74, No. 1-2, pp. 149-158 (1997).
Rosbo, De N. K., et al., "T-Cell Response to Myelin Antigens in Multiple Sclerosis; Relevance of the Predominant Autoimmune Reactivity to Myelin Oligodendrocyte Glycoprotein", Journal of Autoimmunity, 11:287-299 (1998).
Warren, K. G., et al., "The Effect of Intrathecal MBP Synthetic Peptides Containing Epitope P-85VVHFFKNIVIP-96 on Free Anti-MBP Levels in Acute Relapsing Multiple Sclerosis", Journal of the Neurological Sciences, vol. 148, No. 1, pp. 67-78 (1997).
Weerth, S., et al., "Encephalitogenic and Neuritogenic T Cell Response to the Myelin-Associated Glycoprotein (MAG) in the Lewis rat", Journal of Neuroimmunology, vol. 95, No. 1-2, pp. 157-164 (1999).
Wucherpfennig, K. W., et al., "Structural Requirements for Binding of an Immunodominant Myelin Basic Protein Peptide to DR2 Isotypes and for its Recognition by Human T Cell Clones", Journal of Experimental Medicine, vol. 179, No. 1, pp. 279-290 (1994).
Zhong, M., et al., "Multiantigen/Multiepitope-Directed Immune-Specific Suppression of 'Complex Autoimmune Encephalomyelitis' by a Novel Protein Product of a Synthetic Gene", Journal of Clinical Investigation, vol. 110, No. 1, pp. 81-90 (2002).
Adorini L, "Immunotherapeutic approaches in multiple sclerosis," Journal of the Neurological Sciences; 223:13-24 (2004).
Ben-Nun et al, "Anatomy of T cell autoimmunity to myelin oligodendrocyte gly7coprotein (MOG): Prime role of MOG44F in selection and control of MOG-reactive T cells in H-2b mice," Eur. J. Immunol. 36:478-493 (2006).
Ben-Nun A, Wekerle H, Cohen IR. "Vaccination against Autoimmune Encephalomyelitis with Lymphocyte-T Line Cells Reactive against Myelin Basic-Protein," Nature. 292:60-61 (1981).

(Continued)

*Primary Examiner* — Gerald R Ewoldt
(74) *Attorney, Agent, or Firm* — Browdy and Neimark, PLLC

(57) ABSTRACT

Synthetic unaltered and altered peptides comprising sequences of at least one immunogenic epitope cluster (IEC) of at least one human autoantigen related to multiple sclerosis (MS) and at least one nonameric core sequence which fits into the MS-relevant HLA-DR/DQ molecule and is flanked by 2-5 amino acids at its N- and C-termini, are provided. The alteration is preferably by substituting 1 to 3 TCR contact residues by Ala. The autoantigen is preferably MOG, MBP, OSP, MOBP and PLP. Polypeptides comprising at least two such peptides of a sole autoantigen or at least one peptide of two different autoantigens, and synthetic genes encoding them, are also provided, as well as pharmaceutical compositions for treatment and diagnostic of MS.

4 Claims, 21 Drawing Sheets

OTHER PUBLICATIONS

Bielekova, B., and R. Martin, "Antigen-specific immunomodulation via altered peptide ligands," J Mol Med 79:552-565 (2001).

Brocke et al, "Treatment of experimental encephalomyelitis with a peptide analogue of myelin basic protein," Nature. 379:343-346 (1996).

Critchfield et al, "T cell deletion in high antigen dose therapy of autoimmune encephalomyelitis," Science 263:1139-1143 (1994).

Dyment et al, "Genetics of multiple sclerosis," Human Molecular Genetics, 6:1693-1698 (1997).

Etzensperger et al, "Dissection of the multiple sclerosis associated DR2 haplotype," J. Autoimmunity, May 29, 2008 [Epub ahead of print].

Evavold et al, "Tickling the TCR: selective T-cell functions stimulated by altered peptide ligands," Immunol Today. 14:602-609 (1993).

Garcia KC, Teyton L, Wilson IA., "Structural basis of T cell recognition," Annu Rev Immunol. 17:369-397 (1999).

Haines et al. "Linkage of the MHC to familial multiple sclerosis suggests genetic heterogeneity," Human Molecular Genetics 7:1229-1234 (1998).

Kappos et al, "Induction of a non-encephalitogenic type 2 T helper-cell autoimmune response in multiple sclerosis after administration of an altered peptide ligand in a placebo-controlled, randomized phase II trial. The Altered Peptide Ligand in Relapsing MS Study Group," Nat Med. 6:1176-82 (2000).

Kaushansky et al, "Activation and control of pathogenic T cells in OSP/claudin-11-induced EAE in SJL/J mice are dominated by their focused recognition of a single epitopic residue (OSP58M)," Int Immunol. in press (2008).

Kaushansky et al, "OSP/claudin-11-induced EAE in mice is mediated by pathogenic T cells primarily governed by OSP192Y residue of major encephalitogenic region OSP179-207," Eur. J. Immunol. 37:2018-2031 (2007).

Kaushansky et al, "Pathogenic T cells in MOBP-induced murine EAE are predominantly focused to recognition of MOBP21F and MOBP27P epitopic residues," Eur J Immunol, 37:3281-3292 (2007).

Kerlero de Rosbo NK, Ben-Nun A., "T-cell responses to myelin antigens in multiple sclerosis; relevance of the predominant autoimmune reactivity to myelin oligodendrocyte glycoprotein," J Autoimmun. 11:287-299 (1998).

Kersh et al, "Structural Basis for T Cell Recognition of Altered Peptide Ligands: A Single T Cell Receptor Can Productively Recognize a Large Continuum of Related Ligands," J. Exp. Med. 184:1259-1268 (1996).

Kieseier et al, "Treatment and treatment trials in multiple sclerosis," Curr Opin Neurol. 20:286-293 (2007).

Nicholson et al, "An altered peptide ligand mediates immune deviation and prevents autoimmune encephalomyelitis," Immunity 3:397-405 (1995).

Oksenberg et al "The genetics of multiple sclerosis: SNJPs to pathways to pathogenesis," Nat Rev Genet, 9:516-526 (2008).

Sawcer et al. "The genetic analysis of multiple sclerosis," Trends Genet. 13(6):234-239 (1997).

Siebold et al, "Crystal structure of HLA-DQ0602 that protects against type 1 diabetes and confers strong susceptibility to narcolepsy," Proc Natl Acad Sci USA, 101:1999-2004 (2004).

Sloan-Lancaster J, Allen PM., "Altered peptide ligand-induced partial T cell activation: molecular mechanisms and role in T cell biology," Annu Rev Immunol. 14:1-27 (1996).

Sospedra M, Martin R., "Immunology of multiple sclerosis," Annual Review of Immunology. 23:683-747 (2005).

Stern et al, "Crystal structure of the human class II MHC protein HLA-DR1 complexed with an influenza virus peptide," Nature. 368:215-221 (1994).

Swanborg RH., "Antigen-Induced Inhibition of Experimental Allergic Encephalomyelitis: II. Studies in Guinea Pigs with the Small Rat Myelin Basic Protein," J. Immunol. 111: 1067-1070 (1973).

Vandenbark et al, "TCR peptide therapy in human autoimmune diseases," Neurochem Res. 26:713-730 (2001).

Vergelli et al, "Modifications of peptide ligands enhancing T cell responsiveness imply large numbers of stimulatory ligands for autoreactive T cells," J Immunol. 158:3746-3752 (1997).

Warren KG et al, "Intravenous synthetic peptide MBP8298 delayed disease progression in an HLA Class II-defined cohort of patients with progressive multiple sclerosis: results of a 24-month double-blind placebo-controlled clinical trial and 5 years of follow-up treatment" Eur. J. Neurology 13:887-895 (2006).

Windhagen et al, "Modulation of cytokine patterns of human autoreactive T cell clones by a single amino acid substitution of their peptide ligand," Immunity 2:373-380 (1995).

* cited by examiner shMOG gene

| Epitope cluster | MOG amino acid sequence encoded |
|---|---|
| a | 37 — 58<br>VGWYRPPFSRVVHLYRNGKDQD |
| b | 65 — 95<br>YRGRTELLKDAIGEGKVTLRIRNVRFSDEGG |
| c | 7 — 32<br>GPRHPIRALVGDEVELRCRISPGKNA |
| d | 202 — 218<br>LHRRLAGQFLEELRNPF | shMBP gene

| Epitope cluster | MBP amino acid sequence encoded |
|---|---|
| a | 82                          103<br>DENPVVHFFKNIVTPRTPPPSQ |
| b | 136                     156<br>SAHKGFKGVDAQGTLSKIFKL |
| c | 148                      170<br>GTLSKIFKLGGRDSRSGSPMARR |
| d | 7                           29<br>SQRHGSKYLATASTMDHARHGFL |
| e | 25                         45<br>RHGFLPRHRDTGILDSIGRFF | shOSP gene

EcoRI — SpeI — a — b — c — d — NsiI — e — f — PstI — * — HindIII

| Epitope cluster | OSP amino acid sequence encoded |
|---|---|
| a | 48 – 77<br>SKGLWADCVMATGLYHCKPLVDILILPGYV |
| b | 38 – 64<br>PTCRKLDELGSKGLWADCVMATGLYHC |
| c | 94 – 112<br>AILLLLTVLPCIRMGQEPG |
| d | 187 – 206<br>NRFYYTAGSSSPTHAKSAHV |
| e | 17 – 38<br>WIGVIVTTSTNDWVVTCGYTIP |
| f | 124 – 150<br>VLLILLALCALVATIWFPVCAHRETTI |

Fig. 3 shMOBP gene

EcoRI — NheI — PstI — [ a | b | c | d ] — XhoI — * — HindIII

| Epitope cluster | MOBP amino acid sequence encoded |
|---|---|
| a | 13 KNQKYSEHFSIHCCPPFTFLNSKKEI 38 |
| b | 54 QKEEDWTCCACQKTRTSRRAKSPQRPK 80 |
| c | 156 KQQPRSSPLRGPGASRGGS 174 |
| d | 72 RAKSPQRPKQQPAAPPAV 89 |

Fig. 4

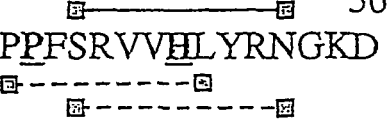
34                              56
GMEVGWYRPPFSRVVHLYRNGKD
34                                      56
GMEVGWYRPPFSRVVHLYRNGKD
67                                              114
GRTELLKDAIGEGKVTLRIRNVRFSDEGGFTSFFRDHSYQEEAAMELK
67                                              114
GRTELLKDAIGEGKVTLRIRNVRFSDEGGFTSFFRDHSYQEEAAMELK
³FRVIGPRHPIRALVGDEVELPSRIS ²⁷
205      215
RLAGQFLEELR
Fig. 10

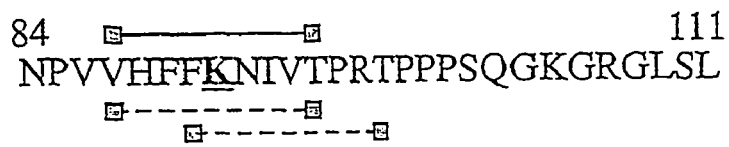
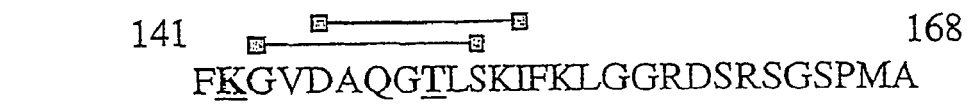
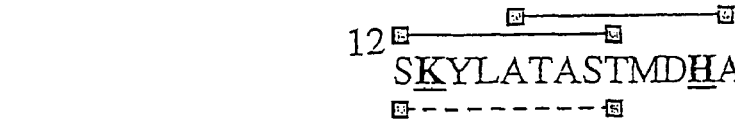
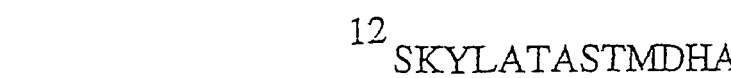
Fig. 11

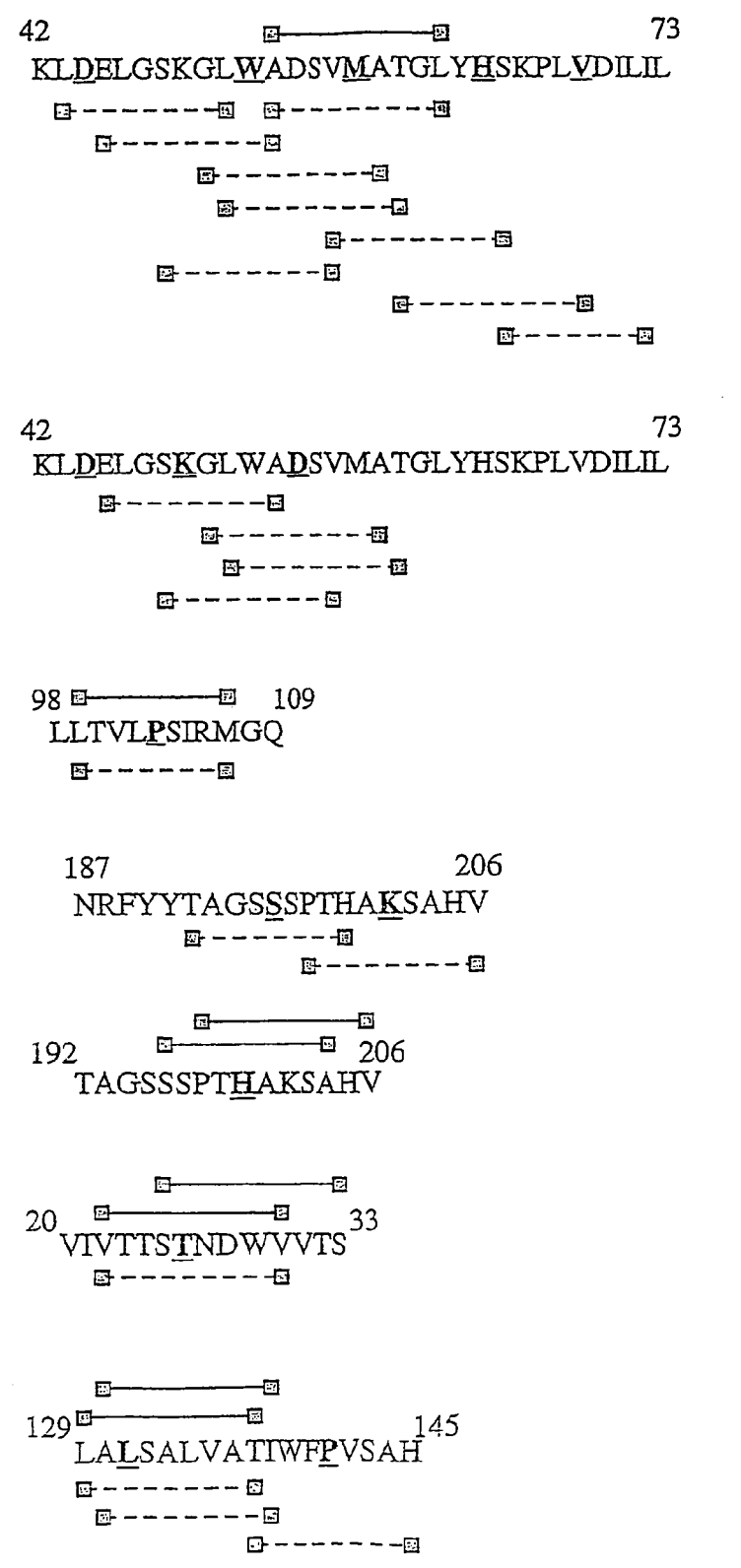

42                                          73
KLDELGSKGLWADSVMATGLYHSKPLVDILIL 42                                          73
KLDELGSKGLWADSVMATGLYHSKPLVDILIL 98         109
LLTVLPSIRMGQ 187                  206
NRFYYTAGSSSPTHAKSAHV 192              206
TAGSSSPTHAKSAHV 20              33
VIVTTSTNDWVVTS 129            145
LALSALVATIWFPVSAH

Fig. 12

```
              15                        33
              QKYSEHFSIHSSPPFTFLN
                 ▫------▫
                      ▫------▫

▫---------▫
              55   ▫----------▫       ▫----------▫            90
              KEEDWISSASQKTRTSRRAKSPQRPKQQPAAPPAVV
                      ▫-------▫

156     ▫--------▫ 172
              KQQPRSSPLRGPGASRG
                  ▫-------▫
                   ▫--------▫
```

Fig. 13

```
103                                                           150
   YKTTISGKGLSATVTGGQKGRGSRGQHQAHSLERVSHSLGKWLGHPDK 103                                                           150
   YKTTISGKGLSATVTGGQKGRGSRGQHQAHSLERVSHSLGKWLGHPDK 103                                                           150
   YKTTISGKGLSATVTGGQKGRGSRGQHQAHSLERVSHSLGKWLGHPDK 177                                203
   FNTWTTSQSIAFPSKTSASIGSLSADA 177                                203
   FNTWTTSQSIAFPSKTSASIGSLSADA 177                                203
   FNTWTTSQSIAFPSKTSASIGSLSADA 218                        240
   VSGSNLLSISKTAEFQMTFHLFI 218                        240
   VSGSNLLSISKTAEFQMTFHLFI 38          52
   ALTGTEKLIETYFSK 264         276
   FAVLKLMGRGTKF
```

Fig. 14 shMOG-AL gene

| Epitope cluster | MOG amino acid sequence encoded |
|---|---|
| A | $^{37}$VGWYRPAFSRVVALYRNGKDQD$^{58}$ |
| B | $^{37}$VGWYRPPFSAVVHLYRNGK$^{55}$ |
| C | $^{65}$YRGRTELLADAIGEGKATLRIANVRFSDEGG$^{95}$ |
| D | $^{77}$GEGKVALRIRAVRFSDEGGF$^{96}$ |
| E | $^{7}$GPRHPIAALVGDEVELASRISPGKNA$^{32}$ |
| F | $^{202}$LHRRLAGQALEELRNPF$^{218}$ | shMBP-AL gene (EcoRI) (NheI) (BamHI) [A] [B] [C] [D] [E] [F] (XbaI) [G] [H] (SpeI) ✻ (HindIII)

| Epitope cluster | MBP amino acid sequence encoded |
|---|---|
| A | 82 DENPVVHFFAANIVTPRTPPPSQ 103 |
| B | 83 ENPVVAFFKNIATPRTPPPSQ 103 |
| C | 136 SAHKGFKGVAAQ shOSP-AL gene

| Epitope cluster | OSP amino acid sequence encoded |
|---|---|
| A | 48 SKGLAADCVAATGLYACKPLADILILPGYV 77 |
| B | 38 PTCRKLAELGSKGLAADCVAATGLYAC 64 |
| C | 39 TSRKLAELGSAGLWAACVMATGLYHC 64 |
| D | 94 AILLLLTVLASIRMGQEPG 112 |
| E | 187 NRFYYTAGSASPTHAASAHV 206 |
| E' | 192 TAGSSSPTAAKSAHV 206 |
| F | 17 WIGVIVTTSANDWVVTSGYTIP 38 |
| G | 124 VLLILLAACALVATIWFAVCAHRETTI 150 | shMOBP-AL gene

| Epitope cluster | MOBP amino acid sequence encoded |
|---|---|
| A | 13 — KNQKYSAHFSIHCCPPATFLNSKKEI — 38 |
| B | 55 — KEEDWACCASQATRTSARAKSPQRPK — 80 |
| C | 156 — KQQPRSSPLAGPGASRGGS — 174 |
| D | 72 — RAKSPQRPAQQPAAPPAV — 89 | shPLP-AL gene

EcoRI — XhoI — NheI — A | A' | B | C | D | E | F | G | H | I | J — BamHI — K | L — BclI — ✻ — NotI — HindIII

| Epitope cluster | PLP amino acid sequence encoded |
|---|---|
| A | 102 DYKTTISGAGLSATVTGGQKG 122 |
| A' | 102 DYKTTISGKGASATVTGGQKG 122 |
| B | 120 QKGRGSRGQAQAHSAERVCHCLGKALGHPDK 150 |
| C | 173 VYIYFNTWTASQSIAFPSATSASIGSLS 200 |
| D | 190 SKTSASIGSASADARMYGV 208 |
| E | 175 IYFNTATTSQSAAFPSKASASIGS 198 |
| F | 185 SAAFPSKASASIASLSADARMY 206 |
| G | 183 SQSIAFASKTSASIASLSAD 202 |
| H | 213 AFPGKVCGSALLSICKTAEFQM 234 |
| I | 225 SISKTAEFQATFHLFLAAF 243 |
| J | 213 AFPGKACGSNALSICKTAEFQMT 235 |
| K | 261 TYNFAVLKLAGRGTKF 276 |
| L | 35 GHEALTGTEALIETYFSKNYQDY 57 |

Fig. 19

SYNTHETIC PEPTIDES AND DNA SEQUENCES FOR TREATMENT OF MULTIPLE SCLEROSIS

FIELD OF THE INVENTION

The present invention relates to synthetic peptides and polypeptides and synthetic human genes useful for the treatment of multiple sclerosis as well as for diagnostic purposes. Abbreviations: AL: altered ligand; APL: altered peptide ligand; CNS: central nervous system; EAE: experimental autoimmune encephalomyelitis; IEC: immunogenic epitopic cluster; MAG: myelin-associated glycoprotein; MBP: myelin basic protein; MOBP: myelin-oligodendrocytic basic protein; MOG: myelin oligodendrocyte glycoprotein; MS: multiple sclerosis; OSP: oligodendrocyte-specific protein;. PBL: peripheral blood lymphocytes; PLP: proteolipid protein; PNS: peripheral nervous system; TCR: T-cell receptor

BACKGROUND TO THE INVENTION

Autoimmune diseases result from the immune system's failure to maintain self-tolerance to antigen(s) in the affected organ. Over 40 systemic and organ-specific autoimmune diseases have been observed. Among the organ-specific autoimmune diseases are multiple sclerosis, myasthenia gravis, thyroiditis, insulin-dependent diabetes mellitus, rheumatoid arthritis and others. In spite of major and significant advances in molecular and cellular immunology in the last two decades, the molecular basis for self-tolerance and the mechanisms regulating it are still a major challenge in immunology, and autoimmune diseases remain a major medical problem. The immune-specific approaches to therapy of the disease, expected to be the most effective, have not yet yielded an effective therapy for any of the autoimmune diseases.

Accordingly, many other approaches have been investigated, some of which resulted in a limited success in decreasing the progression of the disease, such as the use of β-interferon and Copolymer 1 for treatment of multiple sclerosis, yet none of them cure the disease. Apparently, the major difficulty in devising immune specific approaches to therapy lies in the complexity of the autoimmune diseases, particularly with regard to the multiplicity of target antigens and because of the possibility that the primary target antigen(s) may be different in different patients, the difficulty in determining which of the possible target antigens is the primary target antigen for each patient, and against which of the possible epitopes on that protein the pathogenic autoimmune response is primarily directed. This is further complicated by the likely "spread of autoimmunity" as disease develops.

By way of example, multiple sclerosis (MS), an inflammatory disease of the central nervous system (CNS) characterized by neurological impairment of varying extent, results from demyelination, which is believed to result from an autoimmune response against myelin. A number of CNS myelin proteins have been postulated to be potential primary target antigens in MS on the basis of their ability to induce experimental autoimmune encephalomyelitis (EAE), a well-accepted animal model for MS, and detection of autoreactivity to these antigens in MS patients (reviewed in Kerlero de Rosbo and Ben-Nun, 1998, 1999; Kaye et al., 2000; Stevens et al., 1999; Zhong et al., 2000). Among these, myelin basic protein (MBP), proteolipid protein (PLP), and myelin oligodendrocyte glycoprotein (MOG), the major proteins of CNS myelin, have been extensively studied (reviewed in Kerlero de Rosbo and Ben-Nun, 1998, 1999).

Activated CD4+ T cells specific for MBP or PLP are sufficient to cause EAE upon their transfer into naive syngeneic recipients, and potentially pathogenic T cells reactive against MBP or PLP have been demonstrated in MS (reviewed in Tuohy, 1994); however, comparable T cell responses to MBP or PLP were also detected in healthy individuals (reviewed in Tuohy, 1994). Thus, although specific responses to these myelin antigens are likely to be of importance in the course of the disease, they may not represent the primordial pathogenic response in MS. Consequently, in the search for antigenic specificities associated with MS, other myelin-specific, and also more recently non myelin-specific CNS antigens, have been investigated for their encephalitogenicity and/or for the presence of autoreactivity to these antigens in MS. Thus, low levels of T cell response to myelin-associated glycoprotein (MAG) and S100b, found in CNS and PNS tissues, have been observed both in MS patients and control individuals and reactivity to non nervous system-specific antigens such as heat shock proteins, transaldolase, and, to a lesser extent, 2',3'-cyclic nucleotide 3'-phosphodiesterase, has been reported in MS (reviewed in Kerlero de Rosbo and Ben-Nun, 1998). However, none of these antigens have so far been demonstrated to be encephalitogenic, albeit T cells specific for MAG and S100b can cause CNS and PNS inflammation upon passive transfer into syngeneic mice with no clinical manifestations.

In view of the restricted localization of MS lesions to the CNS white matter, it is more likely that a primary target antigen in MS is CNS myelin-specific. Myelin proteins such as MOG, myelin-oligodendrocytic basic protein (MOBP) and oligodendrocyte-specific protein (OSP) are believed to be specific components of CNS myelin (Gardinier et al., 1992; Yamamoto et al., 1994; Bronstein et al., 1997). Our studies on the reactivity to MOG by PBL (peripheral blood lymphocytes) from patients with MS in the context of their reactivity to MBP, PLP and MAG have shown that a high proportion (50%) of MS patients react predominantly to MOG (Kerlero de Rosbo et al., 1997). Most importantly, reactivity to MOG by PBL from control individuals occurs far less frequently (Kerlero de Rosbo et al., 1997). These data, together with the demonstration of the encephalitogenic potential of MOG, strongly suggests that autoimmune reactivity to this CNS myelin-specific antigen plays an important role in the pathogenesis of MS.

Another important point emerged from our investigation of the reactivity by MS PBL to the different myelin antigens, MBP, PLP, MAG and MOG, concomitantly: 40% of the MS patients tested showed no reactivity to any of these myelin antigens. Among the several explanations which could account for this observation, one likely possibility is the involvement of autoimmune reactivity to myelin-specific antigen(s) other than MBP, PLP or MOG. In this context, we have studied the autoreactivity to MOBP, a recently uncovered CNS myelin-specific protein, which is apparently relatively abundant in CNS myelin. Our data yielded from two separate studies of the proliferative response to MOBP by PBL from MS patients and controls indicated that, out of the twenty-two patients tested overall, eleven reacted to one or several MOBP peptides whilst only four out of twenty controls tested overall reacted (Kaye et al., 2000). The demonstration by us and another laboratory that MOBP is also encephalitogenic, provides unequivocal evidence that the autoimmune reactivity observed in MS patients is potentially pathogenic and may play an important role in the pathogenesis of MS. We (Zhong et al., 2000) and another laboratory (Stevens et al., 1999) also recently demonstrated the strong encephalitogenic activity of another CNS myelin-specific protein, OSP, indicating that OSP may also be a potential target antigen for autoimmune demyelinating diseases such as MS.

A potential primary target antigen in MS could be defined as a CNS antigen which has an encephalitogenic potential, i.e. can cause EAE, and against which autoimmune reactivity can be detected in MS patients. In this context, MBP, PLP, MOG and now also MOBP can be considered potential primary target antigens, as autoreactivity against one of these antigens may play an important role in the initiation/progression of MS. In view of its high encephalitogenicity, the potential role of autoimmune responses to OSP in the pathogenesis of MS should also be considered. In contrast, autoimmune responses to other nonencephalitogenic CNS components, myelin-specific or non myelin-specific, which can be detected in MS, are more likely to represent secondary events resulting from "autoimmune spread" as a result of inflammation within CNS with ongoing disease. The multiplicity of potential primary target antigens in MS points to the complexity of the disease with regard to possible pathogenic processes involved, possible etiology of the disease, and most importantly, it imposes major difficulties in devising immune-specific therapeutic approaches to MS.

Thus, the major problems that must be addressed by immune-specific therapies for a given autoimmune disease include the multiplicity of potential primary target antigens with the possibility that the primary target antigens differ in different patients, and the recently acknowledged "spreading of autoimmunity" as disease develops. This phenomenon is described as the observation of variation in the active immunogenic epitopes with the progression of the disease. This results in the evolution of the primary T cell response focused on a particular self-antigen, towards the recruitment of T cells to multiple antigenic determinants on this or other potential target autoantigens within the affected organ (Tuohy et al., 1998; Kumar, 1998).

PCT International Publication WO 01/31037 of the present applicants discloses synthetic human target autoantigen genes comprising sequences coding for at least two immunogenic epitope clusters (hereinafter EEC) of autoantigen(s) related to a specific autoimmune disease, wherein said at least two IECs may be derived from a sole autoantigen or from at least two different autoantigens related to said autoimmune disease, and polypeptides encoded thereby, that can be used for the treatment and diagnosis of autoimmune diseases such as multiple sclerosis (MS), insulin-dependent diabetes mellitus (IDDM), rheumatoid arthritis (RA) and others. Several synthetic human genes have been disclosed in said WO 01/31037, each gene comprising sequences coding for at least two IECs of autoantigen(s) related to a specific autoimmune disease such as MS, IDDM or RA, said synthetic gene being selected from:(i) a synthetic human target autoantigen gene (designated shTAG) comprising nucleotide sequences coding for at least two IECs of a sole autoantigen related to said autoimmune disease; and (ii) a synthetic human multitarget autoantigen gene (designated shMultiTAG) comprising nucleotide sequences coding for at least one IEC of at least two different autoantigens related to said autoimmune disease. WO 01/31037 further disclosed several synthetic polypeptides, each polypeptide comprising amino acid sequences of at least two IECs of autoantigens related to a specific autoimmune disease such as MS, IDDM or RA, said synthetic polypeptide being selected from: (i) a synthetic human polypeptide (designated shPEP) comprising amino acid sequences of at least two IECs of a sole autoantigen related to said autoimmune disease; and (ii) a synthetic human multitarget polypeptide (designated shMultiPEP) comprising amino acid sequences of at least one IEC of at least two different autoantigens related to said autoimmune disease.

In MS, the multiplicity of potentially pathogenic autoreactivities against the myelin components, MBP, PLP, MOG, MOBP, and OSP, which have been detected in different patients, suggest that the primary target antigen(s) and/or the major epitope(s) against which the dominant pathogenic autoreactivities are directed, may differ in different patients. Because neoreactivities are also likely to emerge, disease progression may be associated with multiple potentially pathogenic T cell autoreactivities. This imposes major difficulties for devising immune-specific approaches for therapy of MS.

Thus, effective immune-specific therapy would have to be tailored for each patient according to the antigenic and epitope specificities of the potentially pathogenic autoimmune T-cells detected in that patient, including novel T-cell specificities elicited as a result of "autoimmune spread" as disease progresses. An alternative and more generally applicable approach would ideally be, if all or most of relevant potentially pathogenic autoreactivities could be targeted concomitantly. This would allow immunomodulation of MS, irrespective of the antigenic primacy or dominance of the pathogenic autoimmune response in individual patients.

Several studies in EAE strongly suggest that neutralizing T cells specific for one epitope may not be a sufficiently effective therapeutic approach for disease associated with multiple pathogenic autoreactivities. Thus, in chronic EAE induced in SJL/J mice with whole PLP, tolerization with the major encephalitogenic peptide, PLP139-151, abrogated the primary acute phase, but not subsequent relapses related to autoimmune spread. The clinical severity of EAE induced in (PL/J×SJL/J) $F_1$ mice with a combination of MBP and MOG could be significantly reduced by tolerogenic administration of a combination of the immunodominant encephalitogenic epitopes within MBP Ac1-11 and MOG41-60 (Leadbetter et al., 1998). In contrast, MBPAc1-11, which suppresses MBP-induced EAE in these $F_1$ mice, had no effect on MOG-induced EAE and a marginal therapeutic effect on EAE induced by the MBP/MOG combination (Leadbetter et al., 1998), an observation most likely related to its specific suppressive effect on MBP-reactive T cells. Highly relevant to treatment of disease with multiple autoreactivities is the strong therapeutic effect on EAE of MP4, a chimeric fusion protein, comprising the whole long isoform of MBP (21.5 kDa MBP) and the hydrophilic domains of PLP (ΔPLP) (Elliott et al., 1996).

Tolerogenic administration of MP4 fully abrogated EAE actively induced with PLP139-151, as well as EAE adoptively transferred with a combination of encephalitogenic MBP- and PLP-specific T cells in SJL/J mice. In contrast, neither 21.5 kDa MBP nor ΔPLP injected individually had any such dramatic effect on passive EAE mediated by the combined T cell populations (Elliott et al., 1996). Taken together, these studies suggest that targeting the majority of relevant T cells may be required for optimal efficacy of immune-specific therapy in disease associated with pathogenic T cell reactivities against more than one antigen/epitope.

In summary, the state of the art has convincingly demonstrated that, while EAE resulting from autoreactivity to a single autoantigen can be effectively suppressed by neutralization of the relevant T-cells via tolerogenic administration of the relevant epitope, a single epitope is not effective in suppressing EAE associated with multiple pathogenic autoreactivities. In contrast, targeting all relevant T-cells concomitantly can result in full abrogation of disease.

SUMMARY OF THE INVENTION

In one aspect, the present invention provides a synthetic peptide comprising amino acid sequences of at least one IEC of at least one human autoantigen related to MS, said synthetic peptide being selected from:

(i) an unaltered synthetic peptide comprising at least one nonameric core sequence which fits into the MS-relevant HLA-DR/DQ molecule and is flanked by 2-5 amino acids at its N- and C-termini, the resulting IEC being capable of stimulating human T cells, wherein the peptides are those of SEQ ID Nos: 10 and 22-47; and (ii) an altered synthetic peptide comprising at least one nonameric core sequence which fits into the MS-relevant HLA-DR/DQ molecule and is flanked by 2-5 amino acids at its N-and C-termini, in which sequence 1 to 3 T-cell receptor (TCR) contact amino acid residues are substituted by a suitable amino acid such as Ala, the resulting IEC altered in the TCR residue being capable of immunomodulating the potentially pathogenic T-cell response against the epitope without risk of exacerbation, excluding altered peptides derived from the MBP 83-99 and PLP 139-151 sequences.

The human autoantigen related to MS is preferably MOG, MBP, OSP, MOBP, PLP, and MAG.

Examples of unaltered peptides according to the invention are the MOG peptides of SEQ ID NOs: 22-25 (FIG. 1), the MBP peptides of SEQ ID NOs: 26-30 (FIG. 2), the OSP peptides of SEQ ID NOs: 10, 31-35 (FIG. 3), the MOBP peptides of SEQ ID NOs: 36-39 (FIG. 4), and PLP peptides of SEQ ID NOs: 40-47 (FIG. 5).

Examples of altered peptides according to the invention are the MOG-AL peptides of SEQ ID NOs: 48-53 (FIG. 15), the MBP-AL peptides of SEQ ID NOs: 54-61 (FIG. 16), the OSP-AL peptides of SEQ ID NOs: 62-69 (FIG. 17), the MOBP-AL peptides of SEQ ID NOs: 70-73 (FIG. 18), and the PLP-AL peptides of SEQ ID NOs: 74-86 (FIG. 19).

In another aspect, the present invention provides a synthetic gene comprising nucleotide sequences coding for at least two IECs of a sole autoantigen related to MS or coding for at least one IEC of at least two different autoantigens related to MS and analogs thereof, wherein said IECs have amino acid sequences selected from the sequences of the unaltered and/or altered peptides of the invention, particularly those of SEQ ID NOs: 10 and 22-86.

In a further aspect, the present invention polypeptides that are the protein products of the synthetic genes of the invention and comprise amino acid sequences of at least two IECs of a sole autoantigen related to MS or at least one IEC of at least two different autoantigens related to MS and analogs thereof, wherein said IECs have amino acid sequences selected from the sequences of the unaltered and/or altered peptides of the invention, particularly those of SEQ ID NOs: 10 and 22-86.

In still another aspect, the present invention provides pharmaceutical compositions comprising a mixture of at least two of the unaltered or altered peptides of the invention, or at least one polypeptide or a synthetic gene of the invention for treatment or diagnostic of MS.

BRIEF DESCRIPTION OF THE FIGURES

FIG. 3 depicts a scheme of the herein designated shOSP gene in which the sequences of epitope clusters a-f are SEQ ID NO:32, 31, 33, 16, 34 and 35, respectively.

FIG. 4 depicts a scheme of the herein designated shMOBP gene in which the sequences of epitope clusters a-d are SEQ ID NO:36, 37, 39 and 38, respectively.

FIG. 10 shows the MOG peptides of SEQ ID NOs: 1-4 with the location of the nonameric core sequences predicted to bind and fit into the MS-associated HLA-DR (broken line below the sequence) and HLA-DQ (full line above the sequence) molecules, within the selected MS-related epitope clusters of MOG. Bolded and underlined amino acids represent the TCR contact residues selected to be substituted.

FIG. 11 shows the MBP peptides of SEQ ID NOs: 5-7 with the location of the nonameric core sequences predicted to bind and fit into the MS-associated HLA-DR (broken line below the sequence) and HLA-DQ (full line above the sequence) molecules, within the selected MS-related epitope clusters of MBP. Bolded and underlined amino acids represent the TCR contact residues selected to be substituted.

FIG. 12 shows the OSP peptides of SEQ ID NOs: 8-13 with the location of the nonameric core sequences predicted to bind and fit into the MS-associated HLA-DR (broken line below the sequence) and HLA-DQ (full line above the sequence) molecules, within the selected MS-related epitope clusters of OSP. Bolded and underlined amino acids represent the TCR contact residues selected to be substituted.

FIG. 13 shows the MOBP peptides of SEQ ID NOs: 14-16 with the location of the nonameric core sequences predicted to bind and fit into the MS-associated HLA-DR (broken line below the sequence) and HLA-DQ (full line above the sequence) molecules, within the selected MS-related epitope clusters of MOBP. Bolded and underlined amino acids represent the TCR contact residues selected to be substituted.

FIG. 14 shows the PLP peptides of SEQ ID NOs: 17-21 with the location of the nonameric core sequences predicted to bind and fit into the MS-associated HLA-DR (broken line below the sequence) and HLA-DQ (full line above the sequence) molecules, within the selected MS-related epitope clusters of PLP. Bolded and underlined amino acids represent the TCR contact residues selected to be substituted.

FIG. 16 depicts a scheme of the herein designated shMBP-AL gene in which the sequences of epitope clusters A-H are SEQ ID NO:54-61, respectively.

FIG. 19 depicts a scheme of the herein designated shPLP-AL gene in which the sequences of epitope clusters A, $A^1$ and B-L are SEQ ID NO:74-86, respectively.

DETAILED DESCRIPTION OF THE INVENTION

A. Definitions

Figure 1:
FIG. 1 depicts a scheme of the herein designated shMOG gene in which the sequences of epitope clusters a-d are SEQ ID NO:22-25, respectively.

Within the context of the specification the following definitions will be used: "Autoantigen" refers to the self-molecules (proteins) recognized as potential target antigens in an autoimmune disease. "Epitope" refers to an antigenic determinant of the autoantigen. "Immunogenic epitopic clusters (IEC's)" is used herein to refer to an epitope or collection of epitopes within a region of an autoantigen. The cluster may include one or more flanking, overlapping epitopes or such epitopes in tandem with one another. "Immunogenic (epitopic) cluster coding region" is used to refer to the nucleotide sequence that encodes for an IEC. "Immunogenic" is used herein to refer to the ability of an epitope to initiate an immune response. "Immunomodulatory" is used to refer to the ability of an IEC to modulate, regulate, control or antagonize an autoantigenic induction of an immune response in an appropriate animal model.

B. The Autoantigens for MS

For MS, several autoantigens including MBP, PLP, MAG, MOG, MOBP and OSP have been proposed as being potential targets for the primary autoimmune attack, by an assessment of peripheral blood lymphocytes (PBLs) of MS patients (Kerlero de Rosbo and Ben-Nun, 1998; Kaye et al., 2000) and/or by their ability to invoke a disease-related immunogenic response in the relevant animal model (Kerlero de Rosbo and Ben-Nun, 1999; Kaye et al., 2000; Stevens et al., 1999; Zhong et al., 2000).

C. The Immunogenic Epitopic Clusters (IECs) of the Autoantigens for MS

C1. Unaltered Peptides

The selection of the IECs of the identified potential target autoantigens related to MS is based on experimental identification of the epitopes most frequently recognized in patients, as assayed by reactivity to overlapping peptides of the relevant autoantigen, and/or on determination of the preferred binding mode of regions of the molecule to HLA associated with MS as predicted by computer modeling, preferably confirmed by binding assays and/or experimental data obtained in HLA-transgenic mice. The following Table 1 summarizes IECs which have been experimentally identified or predicted to be potential epitopes for MS, as described in WO 01/31037:

TABLE 1

| Autoimmune disease | Auto-antigen | Location of immunogenic cluster |
|---|---|---|
| Multiple sclerosis | MOG | 34-56, 67-114, 3-27, 205-215 |
|  | MBP | 84-111, 141-168, 12-42 |
|  | OSP | 42-73, 98-110, 187-206, 21-34, 130-146 |
|  | MOBP | 15-33, 55-90, 156-172 |
|  | PLP | 103-150, 177-203, 218-240, 38-52, 264-276 |

In the present invention, computer modeling of the binding mode of the selected epitope clusters to HLA-DR/DQ molecules most prominently associated with MS, was used to predict for each epitope cluster the nonameric core sequences with preferred binding mode to these HLA-DR/DQ and which were seen to fit into the MHC binding site of the HLA-DR structure and/or HLA-DQ model.

The predicted nonameric core sequence in each epitope cluster of each of the potential autoantigens shown in Table 1 above are comprised within the sequences of SEQ ID NOs: 1-21 shown in FIGS. 10-14, as follows:

MOG: 34-56 [SEQ ID NO:1]; 67-114 [SEQ ID NO:2]; 3-27 [SEQ ID NO:3]; 205-215 [SEQ ID NO:4].

MBP: 84-111 [SEQ ID NO:5]; 141-168 [SEQ ID NO:6]; 12-42 [SEQ ID NO:7].

OSP: 42-73 [SEQ ID NO:8]; 98-109 [SEQ ID NO:9]; 187-206[SEQ ID NO:10]; 192-206 [SEQ ID NO:11]; 20-33 [SEQ ID NO:12]; 129-145 [SEQ ID NO:13].

MOBP: 15-33 [SEQ ID NO:14]; 55-90 [SEQ ID NO:15]; 156-172 [SEQ ID NO:16].

PLP: 103-150 [SEQ ID NO:17]; 177-203 [SEQ ID NO:18]; 218-240 [SEQ ID NO:19]; 38-52 [SEQ ID NO:20]; 264-276 [SEQ ID NO:21].

These nonameric core sequences which fit into the MS-relevant HLA-DR/DQ molecule and are flanked by 2-5 amino acids at their N- and C-termini are considered to represent potential epitopes associated with MS. The unaltered peptides of the invention encompassing these predicted epitopes for each target autoantigen have the sequences of SEQ ID NOs: 22-33, 10 and 34-47 as follows:

MOG: 37-58 [SEQ ID NO:22]; 65-95 [SEQ ID NO:23]; 7-32 [SEQ ID NO:24]; 202-218 [SEQ ID NO:25].

MBP: 82-103 [SEQ ID NO:26]; 136-156 [SEQ ID NO:27]; 148-170 [SEQ ID NO:28]; 7-29 [SEQ ID NO:29]; 25-45 [SEQ ID NO:30].

OSP: 38-64 [SEQ ID NO:31]; 48-77 [SEQ ID NO:32]; 94-112 [SEQ ID NO:33]; 187-206 [SEQ ID NO:10]; 17-38 [SEQ ID NO:34]; 124-150 [SEQ ID NO:35].

MOBP: 13-38 [SEQ ID NO:36]; 54-80 [SEQ ID NO:37]; 72-89 [SEQ ID NO:38]; 156-174 [SEQ ID NO:39].

LP: 102-122 [SEQ ID NO:40]; 120-150 [SEQ ID NO:41]; 173-200 [SEQ ID NO:42]; 190-208 [SEQ ID NO:43]; 185-206 [SEQ ID NO:44]; 213-243 [SEQ ID NO:45]; 35-57 [SEQ ID NO:46]; 261-276 [SEQ ID NO:47].

In some of the peptides above, serine (S) residues were replaced by cysteine (C) residues.

C2. The Altered Peptide Ligands (APLs) for MS

Also encompassed by the present invention are immune-specific approaches directed to the potential protective and/or curative effect of analogs of immunodominant encephalitogenic epitopes where TCR contact residues have been manipulated, and which do not stimulate T cell clonal proliferation, i.e. "altered peptide ligands" (APLs).

The specificity of TCR recognition is conferred by only some residues of the peptide presented by MHC class II molecules (Sette et al., 1987; Gautam et al., 1992). To define these TCR contact residues, peptide analogs of specific antigens have been generated in a variety of antigen systems by introducing single amino acid substitutions, and tested for their capacity to stimulate activation events in the T cells specific for the relevant antigenic peptide. Data resulting from such analysis have demonstrated that some of the interactions with the TCR are more critical than others. Thus, the "primary TCR contact site" is defined as the amino acid focused on most intently by all T cells in a population specific for the same antigen, and this amino acid appeared to be the most critical residue of the determinant to the TCR binding. Secondary residues are defined as the other TCR contact sites, which are unique to each TCR in the population, and are assumed to play a lesser role in the overall interaction between TCR and ligand (Evavold et al., 1994; Sloan-Lancaster and Allen, 1996).

Analogs of immunogenic peptides in which the TCR contact sites have been manipulated have been termed "altered peptide ligands" (APLs). These peptides do not stimulate T cell clonal proliferation, but they do bind to the MHC molecules with similar affinities as the unaltered immunogenic peptide, inducing some but not all TCR-mediated effector functions.

The ability of APLs to induce different signaling events has been shown to result in several possible processes of peripheral T cell modulation, anergy and/or induction of Th2-type cytokine secretion and/or antagonistic inhibition of proliferation to the stimulatory peptide and/or inhibition of Th1-type cytokine secretion. Such attributes make APLs very attractive for the design of potential therapeutic approaches to autoimmune diseases.

Epitope-directed, altered peptide ligand (APL)-mediated, downregulation of pathogenic T-cell autoreactivities has been proven by several laboratories to be an effective strategy for immune-specific modulation of EAE. In EAE induced with MBP or PLP, the crucial contact residues involved in the interaction of the TCR wih the encephalitogenic epitope have been identified. APLs whereby these crucial TCR contact residues were altered by substitution with Ala or other amino acids were shown to be highly effective in inhibiting EAE induced with the relevant native MBP or PLP peptide. Similar observations were made with our designed MOG APLs as described hereinafter.

In MS, the human MBP 83-99 region (ENPVVH-FFKNIVTPRTP) (comprised within SEQ ID NO: 26) is one of the major immunodominant MBP epitopes recognized in the context of DR2, the MHC class II haplotype most associated with MS. The TCR contact residues for this epitope have been defined with F-89 apparently representing a primary TCR contact residue, while H-88 and K-91 apparently serve as secondary TCR contact residues (Wucherpfenning et al., 1994; Windhagen et al., 1995; Singh et al., 1999; Kozovska et al., 1998). In EAE, an APL of human MBP 87-99, substituted with Ala at K-91, blocked the disease, apparently via induction of cytokine shift from Th1 to Th2 in the relevant T-cells (Gaur et al., 1997).

An in vitro analysis of the effect of MBP 83-99 APLs on DR2- and DR4-restricted MBP-specific T-cell clones isolated from MS patients revealed that, although the CDR3 motifs of the T-cell clones were diverse, the TCR contact residues within MBP 83-99 were highly conserved, with F-90 and K-91 being critical TCR contact points for both DR2- and DR-4-restricted T-cell clones (Kozovska et al., 1998). Although APLs with Ala substitutions at F-90 or K-91 abolished the positive signalling event in the majority of DR2- and DR4-restricted T-cell clones tested, not all clones could be inhibited by either of these APLs; APLs doubly substituted at these positions, however, abolished responses by all T-cell clones tested (Kozovska et al., 1998). In a further study, deviation of cytokine profile from Th0 to Th2 by T-cell clones in the presence of MBP 83-99 APLs substituted with Ala at the secondary TCR contact residue H-88 was described (Singh et al., 1999).

Data from in vitro analyses of the effect of MBP83-99 APLs on MS patient-derived T-cell clones, together with in vivo analyses with similar APLs in EAE, have led to clinical trials in MS patients. The results of two such phase II clinical trials with subcutaneously injected APLs containing substitutions at the same positions, i.e. positions 83, 84, 89 and 91, were recently reported (Kappos et al., 2000; Bielekova et al., 2000). These two early phase clinical trials, however, were halted prematurely because of adverse allergic reactions (indicating an overly active Th2 response) and, in one case, of exacerbation of MS (*Nature Medicine* 2000 October 6(10): 1167-1182).

It is now well accepted that MBP is not the only potential primary target antigen in MS and that multiple autoreactivities, implicated in the initiation and/or perpetuation of the disease, can occur. In both studies above, it is suggested that therapeutic benefits could be obtained through "bystander" suppression effect (Bielekova et al., 2000; Kappos et al., 2000), whereby targeting of one myelin epitope may induce the production of anti-inflammatory Th2 cytokines, via immune deviation of the pathogenic T-cells and/or induction of Th2-secreting APL-specific T-cells. Recent studies in EAE suggest, however, that targeting the deleterious T-cell reactivity against a single epitope is unlikely to be sufficiently effective in treating a disease associated with multiple autoreactivities.

In the present invention, computer modeling of the binding mode of the selected epitope clusters to HLA-DR/DQ molecules most prominently associated with MS was used to predict for each epitope cluster the nonameric core sequences with preferred binding mode to the HLA-DR/DQ, and which were seen to fit into the MHC binding site of the HLA-DR structure and/or HLA-DQ model.

The predicted nonameric core sequences in each epitope cluster of each of the potential primary target antigens MOG, MBP, OSP, MOBP, and PLP are comprised within the peptides of SEQ ID NOs: 1-21, and are shown in FIGS. 10-14 (broken line below the sequence for the MS-associated HLA-DR, and full line above the sequence for the MS-associated HLA-DQ).

The nonameric core sequences which fit into the MS-relevant HLA-DR/DQ molecule and are flanked by 2-5 amino acids at their N- and C-termini were considered to represent potential epitopes associated with MS. The peptides encompassing these predicted epitopes for each target autoantigen MOG, MBP, OSP, MOBP, and PLP are represented by SEQ ID NOs: 22-33, 10 and 34-47.

For each of the peptides of SEQ ID NOs: 22-33, 10 and 34-47, the TCR contact residues were predicted according to the predicted core nonameric sequence binding to the MS-relevant HLA-DR/DQ molecules. For each autoantigen, the peptides encompassing predicted epitopes were modified in their TCR contact residues by replacement of one or more of said TCR contact residues by alanine (Ala), but substitutions by other suitable amino acids is also encompassed by the invention.

The selection of the TCR contact residues to be substituted took into consideration the overlapping potential epitopes within the clusters, so that autoreactivity against as many overlapping epitopes would be antagonized without interfering with their MHC binding residues or turning some epitopes to super-agonists.

Examples of altered peptides of the invention are represented by the SEQ ID NOs: 48-86, that correspond to the peptides of SEQ ID NOs: 22-33, 10 and 34-47, respectively, but in which one or more TCR contact amino acid residues have been replaced by Ala.

Figure 15:
FIG. 15 depicts a scheme of the herein designated shMOG-AL gene in which the sequences of epitope clusters A-F are SEQ ID NO:48-53, respectively.
Figure 17:
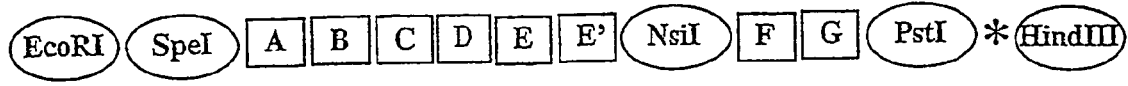
FIG. 17 depicts a scheme of the herein designated shOSP-AL gene in which the sequences of epitope clusters A-G are SEQ ID NO:62-69, respectively.
Figure 18:
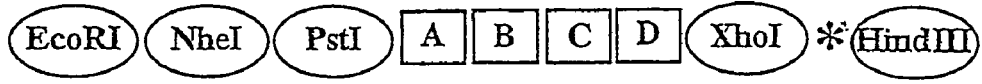
FIG. 18 depicts a scheme of the herein designated shMOBP-AL gene in which the sequences of epitope clusters A-D are SEQ ID NO:70-73, respectively.

The resulting altered peptides of the invention derived from the autoantigens associated with MS are as follows:

MOG-AL peptides A-F (SEQ ID NOs: 48-53, respectively) in FIG. 15 and SEQ ID NOs: 232-233;

MBP-AL peptides A-H (SEQ ID NOs: 54-61, respectively) in FIG. 16;

OSP-AL peptides A-E, E', F,G (SEQ ID NOs: 62-69, respectively) in FIG. 17;

MOBP-AL peptides A-D (SEQ ID NOs: 70-73, respectively) in FIG. 18;

PLP-AL peptides A, A',B-L (SEQ ID NOs: 74-86, respectively) in FIG. 19.

The underlined in these sequences in FIGS. 18-19 are alanine (A) substitutions of the residues representing predicted TCR contact residues within the core sequence predicted to bind to MS-associated HLA class II.

Epitopes appropriately altered in their TCR contact residues, when appropriately administered, are expected to immunomodulate the potentially pathogenic T-cell response against the epitope with minimal risk of exacerbating the pathogenic T-cell response.

For the design of the APLs, for each selected epitope cluster of each autoantigen, computer modeling was used with the purpose to:

(i) identify the nonameric sequence(s) with preferred binding mode to HLA-DR/DQ molecules most prominently associated with MS. Briefly, the crystal structure of the DR molecule (DRA*0101/DRB1*15011), deposited in the Protein Data Bank (PDB code 1bx2), was used to characterize the binding preferences of this MHC molecule. These were represented through a 9×20 matrix in which every entry is a number quantifying the preference of a given amino acid (20 possibilities) to be placed in a given position along the bound peptide (9 possibilities). The structure of the DQ molecule (DQA1*0102/DQB1*0602) is not known, and was modeled according to related structures (PDB codesliak, 2seb), using the MSI modeling software package (MSI Inc., San-Diego, Calif.), in particular the Homology and Discover modules. A 9×20 binding preference matrix was also constructed for this molecule. The binding matrices were used in a computer program in which a 9 amino-acid moving window is applied to the sequence of each epitope cluster of each autoantigen and a binding score is calculated for each 9 amino-acid sequence. This score is estimated as the sum of the binding preferences from the appropriate 9×20 matrix. One of our MHC structures is modeled (DQA1*0102/DQB1*0602) and hence less reliable than an experimental structure. Therefore, in order not to miss possible epitopes, the binding preference matrices must not be too strict. Sequences with binding scores above average were modeled in analogy to MHC class II-bound peptides in known structures (DR, I-A$^k$), and energy-minimized. Of these, sequences which were seen to fit into the MHC binding site were taken as representing possible HLA-binding epitopes.

(ii) Identify crucial TCR contact residues. Studies on crystal structures of peptide-NFC class II complexes have shown that the amino acids at positions 1, 4, 6 and 9 of the nonameric core interacting with the MHC groove are the MHC-binding residues. Amino acids at the other positions, i.e. positions 2, 3, 5, 7 and 8, are directed towards the TCR. It has been experimentally demonstrated that, of these non MHC-binding residues, amino acids at positions 2 and 5 are often the most important TCR contact residues, with position 5 often representing the primary TCR contact residue within the core nonameric sequence. Accordingly, the non MHC-binding residues, preferably at position 5 and/or 2, of the predicted nonameric sequence with preferred binding mode to HLA-DR or -DQ were substituted with Ala. However, substitution of these residues with other amino acids is also envisaged.

FIGS. 10-14 show the nonameric sequences within the selected epitope clusters of each autoantigen, with binding score above average which were also found to fit into the MHC binding site of HLA-DR structure or of HLA-DQ models. Nonameric sequences indicated by broken lines (below sequence) were taken as representing HLA-DR binding epitopes; nonameric sequences indicated by full lines (above sequence) were taken as representing HLA-DQ binding epitopes. As can be seen in these figures, some regions within a selected epitope cluster may contain overlapping HLA-DR and/or HLA-DQ binding epitopes. Hence, alteration of one potential TCR contact residue for one epitope may not antagonize the autoimmune T-cell reactivity against another overlapping epitope. Alternatively, it may interfere with the MHC binding of another overlapping epitope, thus preventing the possibility to antagonize the potential pathogenic T-cell reactivity against this epitope(s). Another possibility may be that alteration of a TCR contact residue of one epitope may affect the overlapping epitope, turning it into a super-agonist rather than an antagonist. These possibilities have been taken into consideration in the selection of the TCR contact residues to be altered for each epitope cluster. Thus, for a region containing overlapping HLA-DR and/or HLA-DQ epitopes, several TCR contact residues may need to be altered, necessitating replicate sequences with substitutions at different positions (for example, see SEQ ID NOs: 48-86). The bolded and underlined amino acids in each epitope cluster shown in FIGS. 10-14, are the TCR contact residues determined to be substituted according to the above criteria.

The present invention thus provides a synthetic peptide comprising amino acid sequences of at least one IEC of at least one human autoantigen related to MS, said synthetic peptide being selected from:

(i) an unaltered synthetic peptide comprising at least one nonameric core sequence which fits into the MS-relevant HLA-DR/DQ molecule and is flanked by 2-5 amino acids at its N- and C-termini, the resulting IEC being capable of stimulating human T cells, wherein the peptides are those of SEQ ID NOs: 10 and 22-47; and (ii) an altered synthetic peptide comprising at least one nonameric core sequence which fits into the MS-relevant HLA-DR/DQ molecule and is flanked by 2-5 amino acids at its N-and C-termini, in which sequence one to three T-cell receptor (TCR) contact amino acid residues are substituted by a suitable amino acid such as Ala, the resulting IEC altered in the TCR residue being capable of immunomodulating the potentially pathogenic T-cell response against the epitope without risk of exacerbation, excluding altered peptides derived from the MBP 83-99 and PLP 139-151 sequences.

Altered peptides derived from the MBP 83-99 sequence are disclosed for example in U.S. Pat. No. 6,251,396 (altered MBP 83-99), U.S. Pat. No. 6,329,499 (altered MBP 86-99) and U.S. Pat. No. 6,369,033 (altered MBP 87-99). Altered PLP 139-151 peptides are disclosed by Hafler, 1996 and Young, 2002.

The IEC is derived from at least one human autoantigen related to MS such as MOG, MBP, OSP, MOBP, PLP, and MAG.

Examples of altered synthetic peptides of the invention include: (i) a peptide containing MOG epitope(s) in which one to three TCR contact residues are substituted by Ala such as the peptides of SEQ ID NOs: 48-53; (ii) a peptide containing MBP epitope(s) in which 1-3 TCR contact residues are substituted by Ala such as the peptides of SEQ ID NOs: 54-61; (iii) a peptide containing OSP epitope(s) in which 1-4 TCR contact residues are substituted by Ala such as the peptides of SEQ ID NOs: 62-69; (iv) a peptide containing MOBP epitope(s) in which 1-3 TCR contact residues are substituted by Ala such as the peptides of SEQ ID NOs: 70-73; and (v) a peptide containing PLP epitope(s) in which 1-3 TCR contact residues are substituted by Ala such as the peptides of SEQ ID NOs: 74-86.

D. The Synthetic Genes for MS

The present invention further provides a synthetic gene comprising nucleotide sequences coding for at least two IECs of a sole autoantigen related to MS or coding for at least one IEC of at least two different autoantigens related to MS and analogs thereof, wherein said IECs have amino acid sequences selected from the sequences of the unaltered and/or altered peptides of the invention, for example the peptides of SEQ ID NOs: 10 and 22-86.

The synthetic genes comprising nucleotide sequences coding for at least two IECs of a sole autoantigen related to MS are herein in the specification and claims identified by a designation including the letters "sh" (standing for "synthetic human") followed by the abbreviation of the autoantigen: shMOG, shMP, shOSP, shMOBP, and shPLP genes (FIGS. 1-5). When the IECs have amino acid sequences of the altered peptides, the letters "AL"(the abbreviation for "altered ligand") follow the abbreviation of the autoantigen: shMOG-AL, shMBP-AL, shOSP-AL, shMOBP-AL, and shPLP-AL genes (FIGS. 15-19).

In one embodiment, the synthetic gene comprises nucleotide sequences coding for at least two IECs of a sole autoantigen related to MS, wherein said IECs have amino acid sequences selected from the sequences of the unaltered peptides of the invention of SEQ ID NOs: 10 and 22-47. Examples are the shMOG (SEQ ID NO:102), shMBP (SEQ ID NO:114), shOSP (SEQ ID NO:128), shMOBP (SEQ ID NO:138), and shPLP (SEQ ID NO:154) genes comprising also restriction endonuclease sites as depicted in FIGS. 1-5, respectively.

In another embodiment, the synthetic gene comprises nucleotide sequences coding for at least two IECs of a sole autoantigen related to MS, wherein said IECs have amino acid sequences selected from the sequences of the altered peptides of the invention, for example of SEQ ID NOs: 48-86. Examples are the shMOG-AL (SEQ ID NO:87), shMBP-AL (SEQ ID NO:88), shOSP-AL (SEQ ID NO:89), shMOBP-AL (SEQ ID NO:90), and shPLP-AL (SEQ ID NO:91) genes comprising also restriction endonuclease sites as depicted in FIGS. 15-19, respectively. For each autoantigen, the amino acid sequences representing epitope clusters with altered TCR contact residues (A, B, C . . . ) were aligned with or without addition of a linker comprised of glycine and serine (GS).

In a further embodiment, the synthetic gene is a multitarget autoantigen gene comprising nucleotide sequences coding for at least one IEC of at least two, preferably 3 or 4, more preferably 5 or more different autoantigens related to MS, and analogs thereof, wherein said IECs have amino acid sequences selected from the sequences of the unaltered and/or altered peptides of the invention.

The synthetic multitarget autoantigen genes comprising nucleotide sequences coding for at least one IEC of at least two different autoantigens related to MS, are herein in the specification and claims identified by a designation including an initial capital Y followed by the abbreviation MS for multiple sclerosis, the letter P and either a small letter "e", when the IECs have amino acid sequences of the unaltered peptides of the invention, for example of SEQ ID NOs: 10 and 22-47, or the letters "AL", when the IECs have amino acid sequences of the altered peptides of the invention, for example of SEQ ID NOs: 48-86. The synthetic multitarget autoantigen genes preferably comprise a high number of preferred IECs of the selected autoantigens, preferably of MOG, MBP, OSP, MOBP and PLP.

Figure 6:
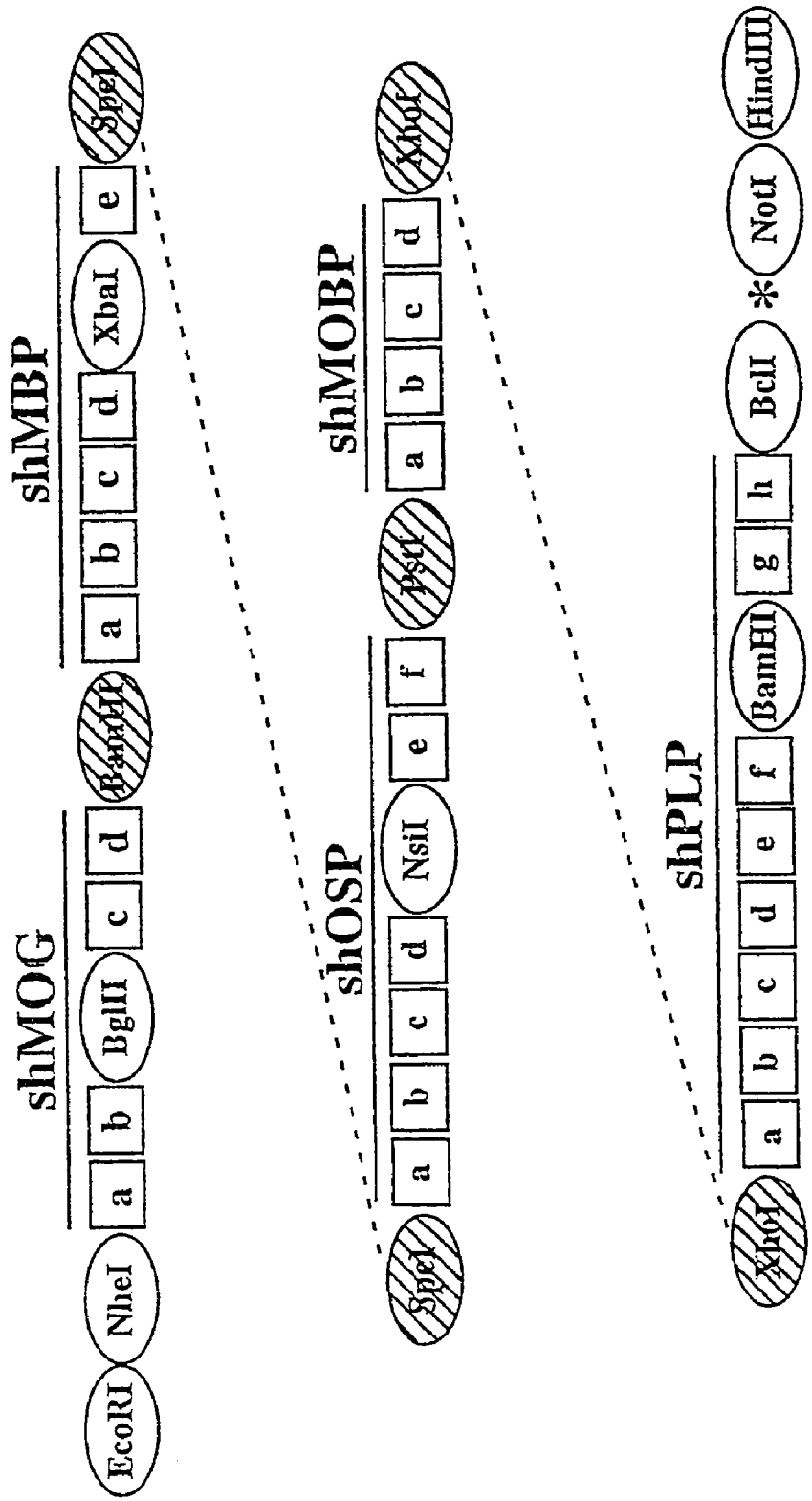
FIG. 6 depicts a scheme of the herein designated Y-MSPe gene.
Figure 7:
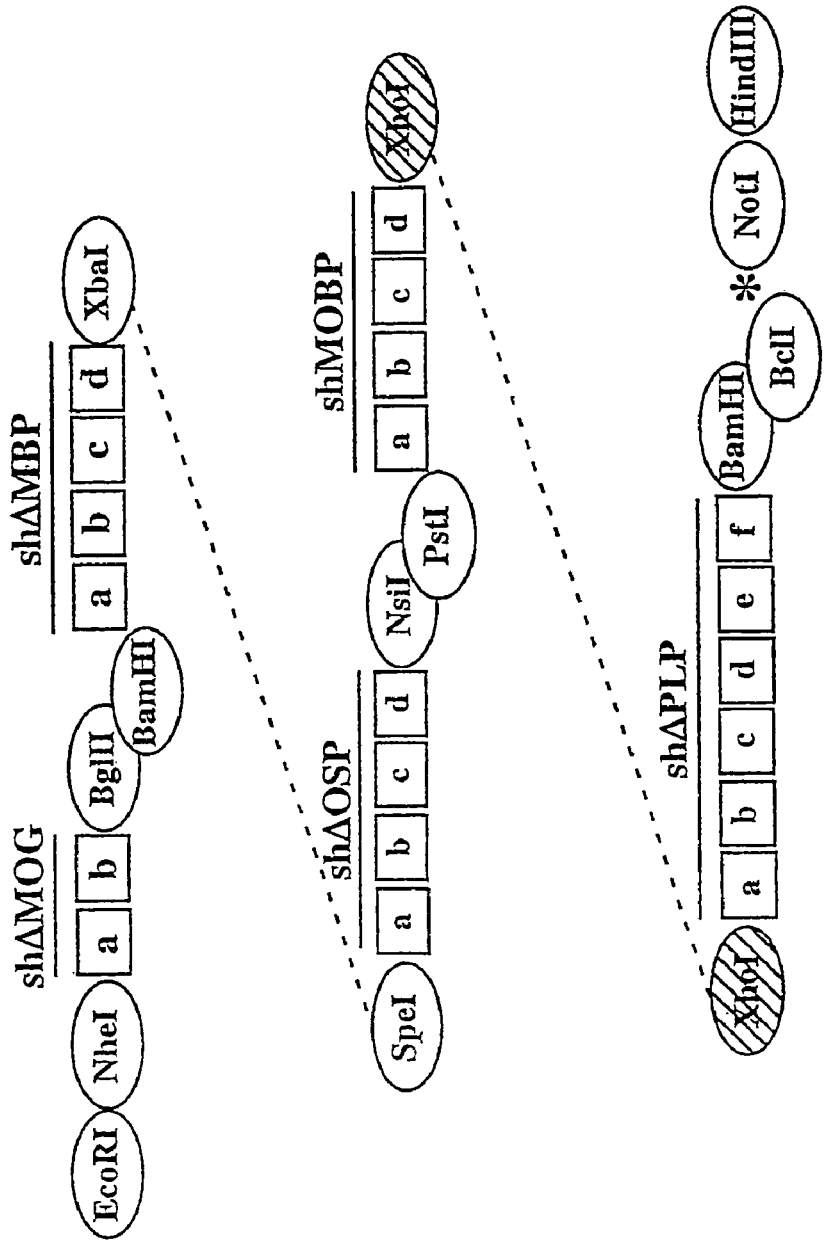
FIG. 7 depicts a scheme of the herein designated ΔY-MSPe gene.

Examples of multitarget autoantigen genes wherein the IECs have amino acid sequences of the unaltered peptides of the invention of SEQ ID NOs: 10 and 22-47, are the genes herein designated Y-MSPe (SEQ ID NO: 225) and ΔY-MSPe (SEQ ID NO: 227), represented by the constructs of FIGS. 6 and 7, respectively.

Figure 20:
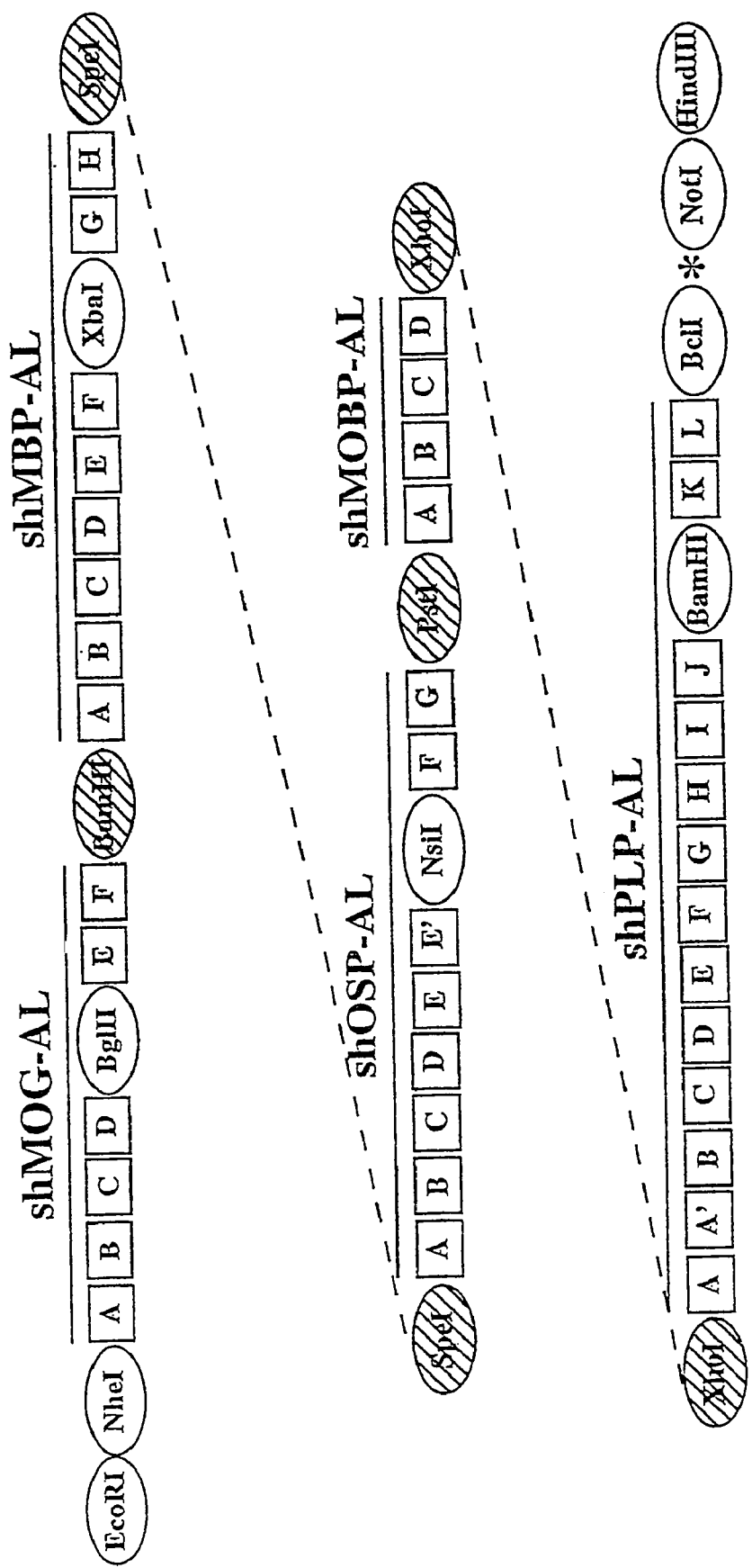
FIG. 20 depicts a scheme of the herein designated Y-MSP-AL gene.
Figure 21:
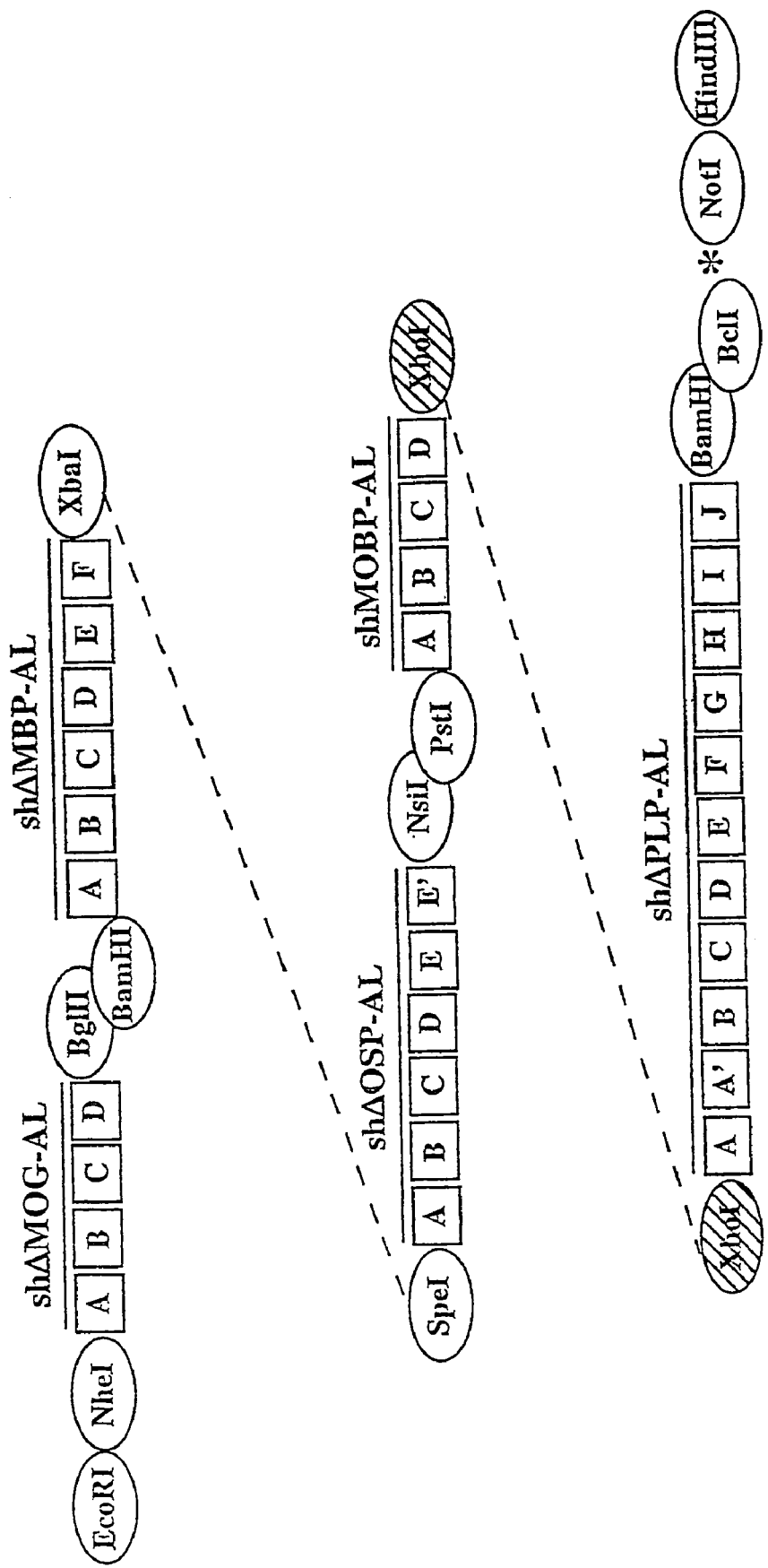
FIG. 21 depicts a scheme of the herein designated ΔY-MSP-AL gene.

Examples of multitarget autoantigen genes wherein the IECs have amino acid sequences of the altered peptides of the invention of SEQ ID NOs: 48-86, are the genes herein designated Y-MSP-AL (SEQ ID NO: 92) and ΔY-MSP-AL (SEQ ID NO: 93), represented by the constructs of FIGS. 20 and 21, respectively.

Synthetic genes and multitarget autoantigen genes wherein the IECs have amino acid sequences of the altered peptides of the invention constitute a preferred embodiment of the invention and include:

(i) a synthetic gene comprising nucleotide sequences coding for at least two, preferably all the six MOG amino acid sequences of the SEQ ID NOs: 48-53, each of them carrying 1-3 alanine substitutions, more preferably the shMOG-AL gene of SEQ ID NO: 87 depicted by the construct of FIG. 15;

(ii) a synthetic gene comprising nucleotide sequences coding for at least two, preferably all the eight MBP amino acid sequences of the SEQ ID NOs: 54-60, each of them carrying 1-3 alanine substitutions, more preferably the shMBP-AL gene of SEQ ID NO: 88 depicted by the construct of FIG. 16;

(iii) a synthetic gene comprising nucleotide sequences coding for at least two, preferably all the eight OSP amino acid sequences of the SEQ ID NOs: 61-69, each of them carrying 1-3 alanine substitutions, more preferably the shOSP-AL gene of SEQ ID NO: 89 depicted by the construct of FIG. 17;

(iv) a synthetic gene comprising nucleotide sequences coding for at least two, preferably all the four of the MOBP amino acid sequences of the SEQ ID NOs: 70-73, each of them carrying 1-3 alanine substitutions, more preferably the shMOBP-AL gene of SEQ ID NO: 90 depicted by the construct of FIG. 18;

(v) a synthetic gene comprising nucleotide sequences coding for at least two, preferably all the 13 of the PLP amino acid sequences of the SEQ ID NOs: 74-86, each of them carrying 1-3 alanine substitutions, more preferably the shPLP-AL gene of SEQ ID NO: 91 depicted by the construct of FIG. 19;

(vi) a synthetic multitarget autoantigen gene comprising the nucleotide sequences of at least two of the synthetic genes of (i)-(v) above, preferably comprising all said sequences, more preferably the Y-MSP-AL gene of SEQ ID NO: 92 depicted by the construct of FIG. 20; and (vii) a synthetic multitarget autoantigen gene being the truncated form of (vi), comprising the nucleotide sequences of at least two synthetic genes selected from the group consisting of: (a) a gene comprising nucleotide sequences coding for the MOG-AL amino acid sequences of the SEQ ID NOs: 48-51; (b) a gene comprising nucleotide sequences coding for the MBP-AL amino acid sequences of the SEQ ID NOs: 54-59; (c) a gene comprising nucleotide sequences coding for the OSP-AL amino acid sequences of the SEQ ID NOs: 62-67; (d) a gene comprising nucleotide sequences coding for the MOBP-AL amino acid sequences of the SEQ ID NOs: 70-73; and (e) a gene comprising nucleotide sequences coding for the PLP-AL amino acid sequences of the SEQ ID NOs: 74-84; preferably the ΔY-MSP-AL gene of SEQ ID NO: 93 depicted by the construct of FIG. 21.

E. Preparation of the Synthetic Genes of the Invention

With a knowledge of the autoantigens and immunogenic epitopic clusters associated with MS, the skilled person may prepare the synthetic genes encoding the IECs of the appropriate autoantigens by standard recombinant techniques. The synthetic genes may contain the coding sequences for the IECs in any particular order, for example, the coding regions for all the clusters from each autoantigen may be grouped together or, alternatively, IECs from different autoantigens may be organized randomly along the synthetic genes. Preferably, the former arrangement prevails and each cluster coding region may be separated from the next by 3, 6, 9 etc. nucleotides or possibly by a restriction site as shown in FIGS. 1-7 and FIGS. 15-21. Any spacing sequences may be inserted in between the coding regions provided that the single open reading frame for the totality of cluster coding regions is retained. In a preferred embodiment, the synthetic gene codes for at least one, preferably 2-3, immunogenic epitopic clusters specific for each of at least two autoantigens, though it may be more preferable to include 4 or 5 or possibly more clusters from each autoantigen. For the constructs of FIGS. 15-19, for each autoantigen, the amino acid sequences representing epitope clusters with altered TCR contact residues (A, B, C . . . ) were aligned with or without addition of a linker comprised of glycine and serine (GS).

General Method for Construction, Amplification and Cloning the Synthetic Genes Synthetic genes coding for the IECs of autoantigens related to MS are obtained stepwise. A synthetic gene for each autoantigen encoding the selected IECs arranged tandemly is prepared by PCR overlap extension using overlapping synthetic oligonucleotides encoding the IECs. Briefly, 60-70 nucleotide long oligonucleotides representing codons of the amino acid residues of the selected IECs are synthesized. The oligonucleotides overlap at their 5' and/or 3' ends by 18 nucleotides which are complementary to their neighboring oligonucleotides. Specific restriction endonuclease sites are included in the first and the last oligonucleotide to facilitate cloning, as well as to enable in frame ligation to neighboring synthetic genes (see below for the construction of the Y-MSPe and Y-MSP-AL genes).

The DNA sequence corresponding to the aligned, linked clusters was modified where necessary, to include alterations not resulting in amino acid changes to neutralize possibly problematic restriction endonuclease sites (RES), to minimize formation of DNA secondary structures or to "bacterize" codons, as well as alterations leading to substitution of cysteine for serine in order to increase the solubility of the expressed protein. DNA sequences corresponding to RES were added to enable cloning and expression, as well as to allow in frame ligation to neighbouring mini-genes.

A template for the synthetic gene is generated by mixing the relevant oligonucleotides (each 75 pmol) in Taq DNA polymerase buffer (40 μl final volume) containing dNTPs (RO181; MBI Fermentas AB, Vilnius, Lithuania) at a final concentration of 0.2 mM each and a mixture of 0.2 U Vent DNA polymerase and 0.2 U Taq DNA polymerase (AB-0192; Advanced Biotechnologies, Surrey, UK). After denaturation (94° C., 1 min) and annealing of the oligonucleotides through their complementary ends (55° C., 2 min), PCR overlap extension is carried out at 72° C. for 5 min, and the resulting template (4 μl) is amplified by PCR at standard conditions for 30 cycles, using the relevant oligonucleotides as 5' and 3' reverse primers. The amplified PCR product of the expected size is eluted from agarose gel and directly cloned into a T vector (pGEM-T, A3600; Promega Corp., Madison, Wis., USA). The constructed synthetic gene is cleaved out from the pGEM-T/synthetic gene plasmid and subcloned into the bacterial expression vector pRSET (V351-20; Invitrogen, San Diego, Calif., USA) via NheI and BglII, 3' to its 6xHis tag, using standard molecular biology techniques. DNA sequence analysis is performed using the pRSET-specific primers to confirm the synthetic gene DNA sequence as an open reading frame with the ATG of the pRSET expression vector.

Other available technologies of molecular biology can be used by a person skilled in the art to prepare the synthetic genes of the invention.

EXAMPLE 1

Construction of the shMOG Gene

The shMOG gene (FIG. 1) was constructed using for template generation the primers designated MOG.p1 (SEQ ID NO: 94), MOG.p2 (reverse=rev), (SEQ ID NO: 95), MOG.p3 (SEQ ID NO: 96), MOG.p4 (rev) (SEQ ID NO: 97), MOG.p5 (SEQ ID NO: 98), MOG.p6 (rev) (SEQ ID NO: 99), and for amplification the 5' and 3' reverse primers MOG.p1a (SEQ ID NO: 100), and MOG.p6a (rev) (SEQ ID NO: 101). The shMOG DNA sequence and derived amino acid sequence are represented by SEQ ID NO: 102 and SEQ ID NO: 103, respectively.

EXAMPLE 2

Construction of the shMBP Gene

The shMBP gene (FIG. 2) was constructed using for template generation the following primers: MBP.p1 (SEQ ID NO: 104), MBP.p2(rev), (SEQ ID NO: 105), MBP.p3 (SEQ ID NO: 106), MBP.p4(rev) (SEQ ID NO: 107), MBP.p5 (SEQ ID NO: 108), MBP.p6(rev) (SEQ ID NO: 109), MBP.p7 (SEQ ID NO: 110), MBP.p8(rev) (SEQ ID NO: 111), and for amplification the 5' and 3' reverse primers MBP.p1a (SEQ ID NO: 112), and MBP.p8a(rev) (SEQ ID NO: 113). The shMBP DNA sequence and derived amino acid sequence are represented by SEQ ID NO: 114 and SEQ ID NO: 115, respectively.

EXAMPLE 3

Construction of the shOSP Gene

The shOSP gene (FIG. 3) was constructed using for template generation the following primers: OSP.p1 (SEQ ID NO: 116), OSP.p2 (rev) (SEQ ID NO: 117), OSP.p3 (SEQ ID NO: 118), OSP.p4 (rev) (SEQ ID NO: 119), OSP.p5 (SEQ ID NO: 120), OSP.p6 (rev) (SEQ ID NO: 121), OSP.p7 (SEQ ID NO: 122), OSP.p8 (rev) (SEQ ID NO: 123), OSP.p9 (SEQ ID NO: 124), OSP.p10 (rev) (SEQ ID NO: 125), and for amplification the 5' and 3' reverse primers OSP.p1a (SEQ ID NO: 126), and OSP.p10a (rev) (SEQ ID NO: 127). The shOSP DNA sequence and derived amino acid sequence are represented by SEQ ID NO: 128 and SEQ ID NO: 129, respectively.

EXAMPLE 4

Construction of the shMOBP Gene

The shMOBP gene (FIG. 4) was constructed using for template generation the following primers: MOBP.p1 (SEQ ID NO: 130), MOBP.p2 (rev) (SEQ ID NO: 131), MOBP.p3 (SEQ ID NO: 132), MOBP.p4 (rev) (SEQ ID NO: 133), MOBP.p5 (SEQ ID NO: 134), MOBP.p6 (rev) (SEQ ID NO: 135), and for amplification the 5' and 3' reverse primers MOBP.p1a (SEQ ID NO: 136), and MOBP.p6a (rev) (SEQ ID NO: 137). The shMOBP DNA sequence and derived amino acid sequence are represented by SEQ ID NO: 138 and SEQ ID NO: 139, respectively.

EXAMPLE 5

Construction of the shPLP Gene

The shPLP gene (FIG. 5) was constructed using for template generation the following primers: PLP.p1 (SEQ ID NO: 140), PLP.p2 (rev) (SEQ ID NO: 141), PLP.p3 (SEQ ID NO: 142), PLP.p4 (rev) (SEQ ID NO: 143), PLP.p5 (SEQ ID NO: 144), PLP.p6 (rev) (SEQ ID NO: 145), PLP.p7 (SEQ ID NO: 146), PLP.p8 (rev) (SEQ ID NO: 147), PLP.p9 (SEQ ID NO: 148), PLP.p10 (rev) (SEQ ID NO: 149), PLP.p11 (SEQ ID NO: 150), PLP.p12 (rev) (SEQ ID NO: 151), and for amplification the 5' and 3' reverse primers PLP.p1a (SEQ ID NO: 152), and PLP.p12a (rev) (SEQ ID NO: 153). The shPLP DNA sequence and derived amino acid sequence are represented by SEQ ID NO: 154 and SEQ ID NO: 155, respectively.

EXAMPLE 6

Construction of the shMOG-AL Gene

The shMOG-AL gene (FIG. 15) was constructed using for template generation the following primers: MOG.AL.p1 (SEQ ID NO: 156), MOG.AL.p2 (rev) (SEQ ID NO: 157), MOG.AL.p3 (SEQ ID NO: 158), MOG.AL.p4 (rev) (SEQ ID NO: 159), MOG.AL.p5 (SEQ ID NO: 160), MOG.AL.p6 (rev) (SEQ ID NO: 161), MOG.AL.p7 (SEQ ID NO: 162), MOG.AL.p8 (rev) (SEQ ID NO: 163), and for amplification the 5' and 3' reverse primers MOG.AL.p1a (SEQ ID NO: 164), and MOG.AL.p8a (rev) (SEQ ID NO: 165). The shMOG-AL DNA sequence and derived amino acid sequence are represented by SEQ ID NO: 87 and SEQ ID NO: 166, respectively.

EXAMPLE 7

Construction of the shMBP-AL Gene

The shMBP-AL gene (FIG. 16) was constructed using for template generation the following primers: MBP.AL.p1 (SEQ ID NO: 167), MBP.AL.p2 (rev) (SEQ ID NO: 168), MBP.AL.p3 (SEQ ID NO: 169), MBP.AL.p4 (rev) (SEQ ID NO: 170), MBP.AL.p5 (SEQ ID NO: 171), MBP.AL.p6 (rev) (SEQ ID NO: 172), MBP.AL.p7 (SEQ ID NO: 173), MBP.AL.p8 (rev) (SEQ ID NO: 174), MBP.AL.p9 (SEQ ID NO: 175), MBP.AL.p10 (rev) (SEQ ID NO: 176), and for amplification the 5' and 3' reverse primers MBP.AL.p1a (SEQ ID NO: 177), and MBP.AL.p10a (rev) (SEQ ID NO: 178). The shMBP-AL DNA sequence and derived amino acid sequence are represented by SEQ ID NO: 88 and SEQ ID NO: 179, respectively.

EXAMPLE 8

Construction of the shOSP-AL Gene

The shOSP-AL gene (FIG. 17) was constructed using for template generation the following primers: OSP.AL.p1 (SEQ ID NO: 180), OSP.AL.p2 (rev) (SEQ ID NO: 181), OSP.AL.p3 (SEQ ID NO: 182), OSP.AL.p4 (rev) (SEQ ID NO: 183), OSP.AL.p5 (SEQ ID NO: 184), OSP.AL.p6 (rev) (SEQ ID NO: 185), OSP.AL.p7 (SEQ ID NO: 186), OSP.AL.p8 (rev) (SEQ ID NO: 187), OSP.AL.p9 (SEQ ID NO: 188), OSP.AL.p10 (rev) (SEQ ID NO: 189), OSP.AL.p11 (SEQ ID NO: 190), OSP.AL.p12 (rev) (SEQ ID NO: 191), and for amplification the 5' and 3' reverse primers OSP.AL.p1a (SEQ ID NO: 192), and OSP.AL.p12a (rev) (SEQ ID NO: 193). The shOSP-AL DNA sequence and derived amino acid sequence are represented by SEQ ID NO: 89 and SEQ ID NO: 194, respectively.

EXAMPLE 9

Construction of the shMOBP-AL Gene

The shMOBP-AL gene (FIG. 18) was constructed using for template generation the following primers: MOBP.AL.p1 (SEQ ID NO: 195), MOBP.AL.p2 (rev) (SEQ ID NO: 196), MOBP.AL.p3 (SEQ ID NO: 197), MOBP.AL.p4 (rev) (SEQ ID NO: 198), MOBP.AL.p5 (SEQ ID NO: 199), MOBP.AL.p6 (rev) (SEQ ID NO: 200), and for amplification the 5' and 3' reverse primers MOBP.AL.p1a (SEQ ID NO: 201), and MOBP.AL.p6a (rev) (SEQ ID NO: 202). The shMOBP-AL DNA sequence and derived amino acid sequence are represented by SEQ ID NO: 90 and SEQ ID NO: 203, respectively.

EXAMPLE 10

Construction of the shPLP-AL Gene

The shPLP-AL gene (FIG. 19) was constructed using for template generation the following primers: PLP.AL.p1 (SEQ ID NO: 204), PLP.AL.p2 (rev) (SEQ ID NO: 205), PLP.AL.p3 (SEQ ID NO: 206), PLP.AL.p4 (rev) (SEQ ID NO: 207), PLP.AL.p5 (SEQ ID NO: 208), PLP.AL.p6 (rev) (SEQ ID NO: 209), PLP.AL.p7 (SEQ ID NO: 210), PLP.AL.p8 (rev) (SEQ ID NO: 211), LP.AL.p9 (SEQ ID NO: 212), PLP.AL.p10 (rev) (SEQ ID NO: 213), PLP.AL.p11 (SEQ ID NO: 214), PLP.AL.p12 (rev) (SEQ ID NO: 215), PLP.AL.p13 (SEQ ID NO: 216), PLP.AL.p14 (rev) (SEQ ID NO: 217), PLP.AL.p15 (SEQ ID NO: 218), PLP.AL.p16 (rev) (SEQ ID NO: 219), PLP.AL.p17 (SEQ ID NO: 220), PLP.AL.p18 (rev) (SEQ ID NO: 221), and for amplification the 5' and 3' reverse primers PLP.AL.p1a (SEQ ID NO: 222), and PLP.AL.p18a (rev) (SEQ ID NO: 223). The shPLP-AL DNA sequence and derived amino acid sequence are represented by SEQ ID NO: 91 and SEQ ID NO: 224, respectively.

EXAMPLE 11

Construction of the Y-MSPe Gene

A synthetic multitarget autoantigen gene of the invention encoding randomly organized EECs of several autoantigens is prepared by ligating together the resulting synthetic genes for each autoantigen in one open reading frame to form the desired multiple gene.

Briefly, for construction of the Y-MSPe gene, the shMOG, shMBP, shOSP, shMOBP and shPLP genes of Examples 1-5 above are ligated sequentially via specific endonuclease restriction sites which have been incorporated to allow their ligation in one open reading frame as shown in the construct depicted in FIG. 6. To this end, the pGEM-T/shMOG is cleaved at the BamHI and HindIII sites, the shMBP gene is excised from pGEM-T/shMBP with BamHI and SpeI, the shOSP gene is excised from pGEM-T/shOSP with SpeI and PstI, the shMOBP gene is excised from pGEM-T/shMOBP with PstI and XhoI, and the shPLP gene is excised from pGEM-T/shPLP with XhoI and HindIII. The DNA fragments of the right sizes are eluted from agarose gel, cleaned and sequential ligations are carried out to link the shMBP gene to the shMOG gene via their BamHI sites, the shOSP gene to the shMBP gene via their SpeI sites, the shMOBP gene to the shOSP gene via their PstI sites, and the shPLP gene to the shMOBP gene via their XhoI sites and to the pGEM-T/shMOG via their HindIII sites, as depicted in FIG. 6. The resulting ligated DNA fragment comprising the five synthetic genes representing Y-MSPe is then subcloned into the pRSET bacterial expression vector (Invitrogen), 3' to its 6xHis tag, via the NheI and HindIII restriction sites. DNA sequence analysis is performed using the pRSET-specific primers to confirm the Y-MSPe DNA sequence as an open reading frame with the ATG of the pRSET expression vector. The Y-MSPe DNA sequence and derived amino acid sequence are represented by SEQ ID NO: 225 and SEQ ID NO: 226, respectively.

EXAMPLE 12

Construction of the ΔY -MSPe Gene

For construction of the ΔY-MSPe gene, the MS-related truncated Y-MSPe gene coding only for preferred epitopes likely to be more frequently recognized in disease on each of the autoantigens selected, is prepared as follows: the pGEM-T/shPLP is cleaved at BamHI and BclI and the small BamHI/BclI fragment is removed by gel electrophoresis. The pGEM-T/shPLP is then religated via the compatible BamHI/BclI sites to generate the pGEM-T/shΔPLP. The XhoI/HindIII DNA fragment comprising the shΔPLP gene is excised out from the pGEM-T/shΔPLP and ligated into the pRSET/Y-MSPe digested with XhoI and HindIII to replace the shPLP gene. The resulting plasmid (pRSET/Y-MSPe with shPLP) is then digested with NheI and HindIII and the excised DNA fragment (Y-MSPe with shΔPLP) is sequentially cleaved and religated via the compatible restriction sites BglII and BamHI, followed by XbaI and SpeI, followed by NsiI and PstI, as depicted in FIG. 7. The resulting DNA fragment comprising the shΔ symthetic genes is cloned back into the pRSET vector via the NheI and HindIII sites. The resulting plasmid is the pRSET/ΔY-MSPe (ΔY-MSPe). DNA sequence analysis is performed using the pRSET-specific primers to confirm the ΔY-MSPe DNA sequence as an open reading frame with the ATG of the pRSET expression vector. The ΔY-MSPe DNA sequence and derived amino acid sequence are represented by SEQ ID NO: 227 and SEQ ID NO: 228, respectively.

EXAMPLE 12

Construction of the Y-MSP-AL and ΔY-MSP-AL Genes

The Y-MSP-AL and ΔY-MSP-AL genes are constructed in exactly the same manner as described in Examples 10-11 above, according to the schemes depicted in FIGS. 20 and 21, respectively.

The Y-MSP-AL DNA sequence and derived amino acid sequence are represented by SEQ ID NO: 92 and SEQ ID NO: 229, respectively.

The ΔY-MSP-AL DNA sequence and derived amino acid sequence are represented by SEQ ID NO: 93 and SEQ ID NO: 230, respectively.

F. The Polypeptides of the Invention and Their Preparation

The invention further provides a synthetic polypeptide comprising amino acid sequences of at least two IECs of a sole autoantigen related to MS or at least one IEC of at least two different autoantigens related to MS and analogs thereof, wherein said amino acid sequences are selected from the sequences of the unaltered and/or altered peptides of the invention.

In one embodiment, the polypeptide comprises the unaltered amino acid sequences of at least two IECs of a sole autoantigen related to MS consisting of the polypeptides shMOG (SEQ ID NO:103), shMBP (SEQ ID NO:115), shOSP (SEQ ID NO:129), shMOBP (SEQ ID NO:139), and shPLP (SEQ ID NO:155).

In another embodiment, the polypeptide comprises the unaltered amino acid sequences of at least one IEC of at least two different autoantigens related to MS, preferably the polypeptides Y-MSPe (SEQ ID NO:226) and ΔY-MSPe (SEQ ID NO:228).

In a preferred embodiment, the polypeptides comprise the sequences of the altered peptides of the invention and include, for example:

(i) a polypeptide comprising at least two, preferably all the six MOG-AL amino acid sequences of the SEQ ID NOs: 48-53, each of them carrying 1-3 alanine substitutions, preferably containing all the six sequences, more preferably the polypeptide of the amino acid sequence of SEQ ID NO: 166;

(ii) a polypeptide comprising at least two, preferably all the eight MBP-AL amino acid sequences of the SEQ ID NOs: 54-61, each of them carrying 1-3 alanine substitutions, preferably containing all the eight sequences, more preferably the polypeptide of the amino acid sequence of SEQ ID NO: 179;

(iii) a polypeptide comprising at least two, preferably all the eight OSP-AL amino acid sequences of the SEQ ID NOs: 62-69, each of them carrying 1-4 alanine substitutions, preferably containing all the eight sequences, more preferably the polypeptide of the amino acid sequence of SEQ ID NO: 194;

(iv) a polypeptide comprising at least two, preferably all the four of the MOBP-AL amino acid sequences of the SEQ ID NOs: 70-73, each of them carrying 1-3 alanine substitutions, preferably comprising the four sequences, more preferably the polypeptide of the amino acid sequence of SEQ ID NO: 203;

(v) a polypeptide comprising at least two, preferably all the 13 of the PLP-AL amino acid sequences of the SEQ ID NOs: 74-86, each of them carrying 1-3 alanine substitutions, more preferably the polypeptide of the amino acid sequence of SEQ ID NO: 224;

(vi) a polypeptide comprising: (a) at least two, preferably all the six MOG-AL amino acid sequences of the SEQ ID NOs: 48-53; (b) at least two, preferably all the eight MBP-AL amino acid sequences of the SEQ ID NOs: 54-61; (c) at least two, preferably all the eight OSP-AL amino acid sequences of the SEQ ID NOs: 62-69; (d) at least two, preferably all the four of the MOBP-AL amino acid sequences of the SEQ ID NOs: 70-73; and (e) at least two, preferably all the 13 of the PLP-AL amino acid sequences of the SEQ ID NOs: 74-86, each of the amino acid sequences carrying 1-3 alanine substitutions, preferably comprising all said sequences (a)-(e), more preferably the polypeptide of the amino acid sequence of SEQ ID NO: 229; and (vii) a polypeptide being the truncated form of (vi), comprising: (a) the MOG amino acid sequences of the SEQ ID NOs: 48-51; (b) the MBP amino acid sequences of the SEQ ID NOs: 54-59; (c) the OSP amino acid sequences of the SEQ ID NOs: 62-67; (d) the MOBP amino acid sequences of the SEQ ID NOs: 70-73; and (e) the PLP amino acid sequences of the SEQ ID NOs: 74-84; each of the amino acid sequences carrying 1-3 alanine substitutions, preferably the polypeptide of the amino acid sequence of SEQ ID NO: 230.

For the preparation of the polypeptides, the synthetic genes of the present invention can be incorporated into expression vector that may be, for example, plasmid or virus vectors provided with an origin of replication, optionally a promoter for the expression of the said synthetic gene and optionally a regulator of the promoter. The recombinant expression vector may then be used to transform or transfect suitable host cells such as bacterial cells, e.g. *E. coli* cells, or eukaryotic cells such as yeast, insect or preferably, mammalian cells, to provide for expression of a polypeptide of the invention. This process may comprise culturing a host cell transformed with an expression vector as described above under conditions to provide for expression of the polypeptide. The expressed polypeptide is then recovered by extraction from the host cells by a variety of techniques known in the art, including enzymatic, chemical and/or osmotic lysis and physical disruption, and isolated by protein purification methods known in the art, such as metal chelate chromatography, HPLC, antibody-affinity chromatography etc.

EXAMPLE 13

Expression of the Protein Products of the Synthetic Genes

The synthetic gene of any one of Examples 1-12 above is cleaved out from the pGEM-T/synthetic gene plasmid and subcloned into the bacterial expression vector pRSET (V351-20; Invitrogen, San Diego, Calif., USA) via suitable restriction sites such as NheI and BglII or NheI and HindIII, 3' to its 6xIis tag, using standard molecular biology techniques. DNA sequence analysis is performed using the pRSET-specific primers to confirm the synthetic gene DNA sequence as an open reading frame with the ATG of the pRSET expression vector.

The pRSET/synthetic gene is then transformed into *Escherichia coli* host (BL21-DE3), and protein expression is induced by isopropyl β-D-thio-galactopyranoside (IPTG) (RO392; MBI Fermentas AB). After expression is observed, the expressed protein product is isolated under denaturing conditions (8 M urea) by metal chelate affinity chromatography on $Ni^{2+}$ nitriloacetic acid (NTA) agarose (30230; Qiagen Inc., Valencia, Calif., USA) according to the manufacturer's protocol. Fractions containing the isolated protein, as evidenced by SDS-PAGE, are pooled and subjected to reducing conditions with β-mercaptoethanol. The protein is diluted to 50-100 μg/ml in 8 M urea and allowed to refold by dialysis against gradually decreasing concentrations of urea (8-0 M). Any aggregated protein is removed by centrifugation.

The synthetic gene may also be expressed in a mammalian expression vector as described in WO 01/31037. Thus, the synthetic gene DNA is cleaved out from the pGEM-T/synthetic gene plasmid with EcoRI and NotI and subcloned into the mammalian expression vector pCDNA 3.1. The pCDNA 3.1/synthetic gene is transfected into mammalian cells, e.g. NIH3T3 mouse fibroblasts, CHO or any other suitable mammalian cells, and the expressed protein product is isolated and examined by standard molecular biology techniques.

G. Pharmaceutical Compositions

The present invention further provides pharmaceutical compositions for multiepitope-directed immunomodulation of MS comprising a pharmaceutically acceptable carrier and a mixture of two or more unaltered and/or altered peptides of the invention, or a synthetic gene of the invention or a polypeptide which is a protein product of a synthetic gene of the invention.

The synthetic genes and their protein products may be useful for concomitant immunomodulation of potentially pathogenic autoreactivities against different or multiple epitopes of a single or several target antigens in MS, via DNA vaccination or via tolerogenic administration of the protein product of the synthetic gene.

Thus, the present invention further relates to a pharmaceutical composition for multiepitope-directed immunomodulation of MS comprising a pharmaceutically acceptable carrier and an agent selected from:

(i) a mixture of at least two synthetic peptides, each peptide comprising amino acid sequences of at least one immunogenic epitope cluster (IEC) of at least one human autoantigen related to multiple sclerosis (MS), said peptide being selected from an unaltered synthetic peptide comprising at least one nonameric core sequence which fits into the MS-relevant HLA-DR/DQ molecule and is flanked by 2-5 amino acids at its N- and C-termini, the resulting IEC being capable of stimulating human T cells;

(ii) a mixture of at least two synthetic peptides, each peptide comprising amino acid sequences of at least one immunogenic epitope cluster (IEC) of at least one human autoantigen related to multiple sclerosis (MS), said peptide being selected from an altered synthetic peptide comprising at least one nonameric core sequence which fits into the MS-relevant HLA-DR/DQ molecule and is flanked by 2-5 amino acids at its N- and C-termini, in which sequence one to three T-cell receptor (TCR) contact amino acid residues are substituted by a suitable amino acid such as Ala, the resulting IEC altered in the TCR residue being capable of immunomodulating the potentially pathogenic T-cell response against the epitope without risk of exacerbation;

(iii) a synthetic gene of the invention; and (iv) a polypeptide of the invention.

The formulation of the pharmaceutical composition of the invention comprising a mixture of peptides will depend upon the route of administration but typically they can be formulated for topical, parenteral, intramuscular, intravenous, intraperitoneal, intranasal inhalation, lung inhalation, or intradermal administration. The polypeptide may be administered in an injectable form by mixing with a pharmaceutically acceptable vehicle for an injectable formulation.

The pharmaceutically acceptable carrier or diluent may be, for example, sterile isotonic saline solutions, or other isotonic solutions such as phosphate-buffered saline. Additional ingredients of the formulations include suitable binder(s), lubricant(s), suspending agent(s), coating agent(s), solubilising agent(s).

Typically, the physician will determine the actual dosage, which will be most suitable for an individual patient, and it will vary with the age, weight and response of the particular patient.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

The compositions as well as the polypeptides alone can also be injected parenterally, for example intracavernosally, intravenously, intramuscularly or subcutaneously. In this case, the compositions will comprise a suitable carrier or diluent. For parenteral administration, the compositions are best used in the form of a sterile aqueous solution, which may contain other substances, for example enough salts or monosaccharides to make the solution isotonic with blood.

The present invention also provides pharmaceutical compositions for the treatment of MS comprising at least one synthetic gene of the invention to be administered via "naked DNA" vaccination or together with a suitable gene delivery vehicle. The gene delivery vehicle may be a non-viral vehicle such as cationic liposomes or a cationic lipid vehicle, or a viral vehicle such as adenovirus vector, an adeno-associated viral (AAV) vector, a herpes viral vector, a retroviral vector, a lentiviral vector or a baculoviral vector. The gene can be, for example, integrated in a retroviral expression vector.

When injected in a soluble tolerogenic route (s.c., i.v. or i.p.) or administered by oral or nasal application, the composition of the invention is expected to downregulate the potentially pathogenic autoimmune responses in MS. Alternatively, when administered as a naked DNA constructed into an appropriate mamalian expression vector, the synthetic gene of the invention can be effective in vaccinating against the disease.

H. Diagnostic Compositions

The unaltered and altered peptides as well as the polypeptides comprising sequences of the unaltered and altered peptides of the invention can also be used for diagnosis and/or for monitoring the progression of MS by measuring the levels of immunoactivation of T-cells specific for the autoantigen(s) associated with the disease. T-cell responses to the peptides or polypeptides are likely to be higher in patients than in control individuals, and measurement of such responses by blood cells or serum can be used as a diagnostic/monitoring tool.

The levels of T-cell autoreactivity to the peptides or polypeptides are measured by incubating PBLs isolated from peripheral blood in the presence of the relevant peptides or polypeptides, and monitoring the activation of the reactive T-cells by detection of T-cell proliferation, cytokine release and expression of cytokine receptors and other activation-associated cell surface markers. Such assays of T-cell activation are well known to those of skill in the art.

EXAMPLE 14

MOG APLs Substituted at Crucial TCR Contact Residues 41 and 44 Suppress EAE Induced with MOG 37-52

The altered peptides of the invention were tested for their biological activity in relevance to MS, using EAE as a model system.

Figure 8:
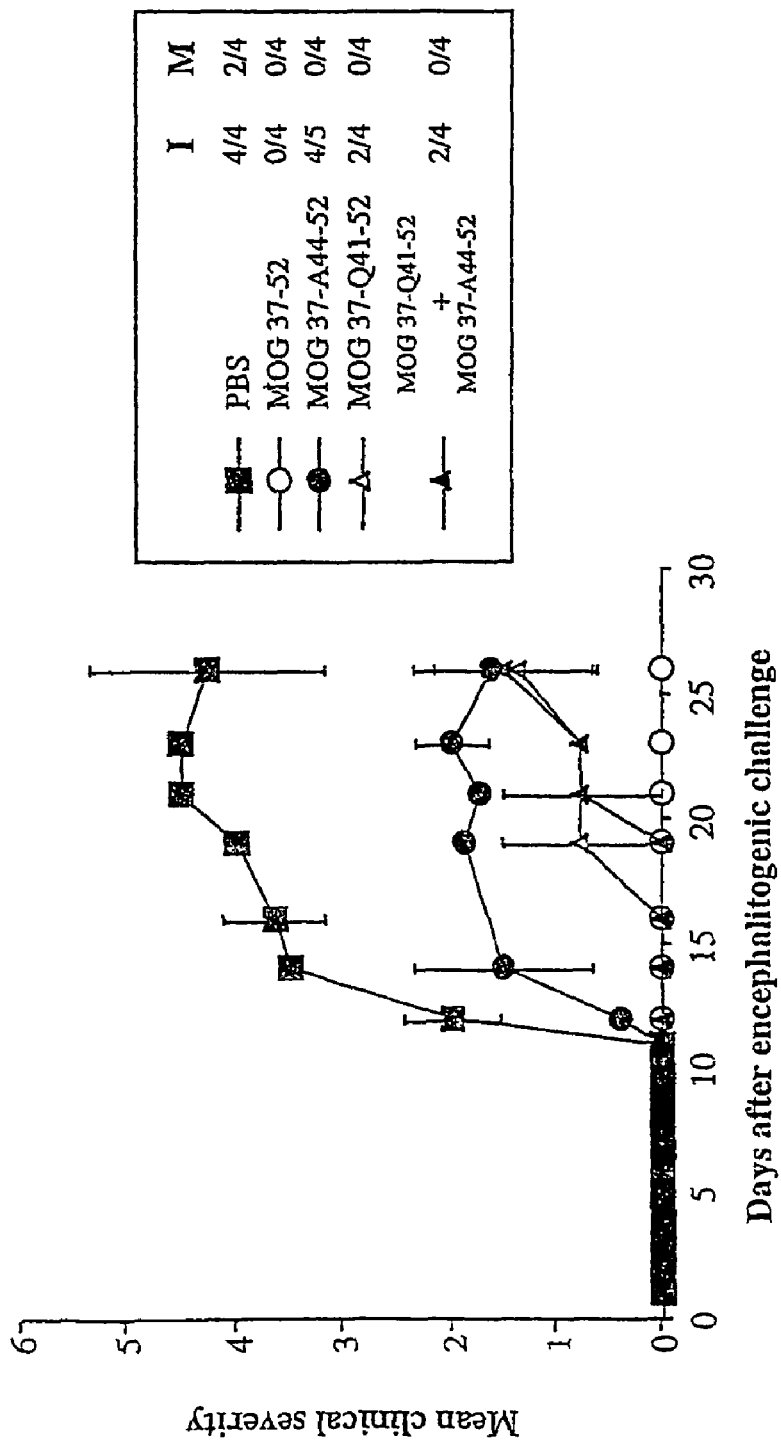
FIG. 8 shows that MOG altered peptide ligands (APLs) substituted at crucial T-cell receptor (TCR) contact residues 41 and 44 suppress EAE induced with peptide MOG 37-52. I and M indicate incidence of disease and mortality in the group, respectively.

For EAE induction, female 2-3 months old C3H.SW mice (Jackson Laboratory, Bar harbor, Maine, USA) were immunized with MOG 37-52 (150 µg emulsified with CFA supplemented with 300 µg *Mycobacterium tuberculosis*). On days 5, 7, 9 and 12 after encephalitogenic challenge, the mice were injected intravenously (i.v.) with an aqueous solution of MOG 37-52 (SEQ ID NO: 231), MOG 37-A44-52 (SEQ ID NO: 232), or MOG 37-Q41-52 (SEQ ID NO: 233), (400 µg in PBS), or with a combination of MOG 37-A44-52+MOG 37-Q41-52, or with PBS alone. Mice were followed and scored daily for clinical effects on a scale of 0-6. The results in FIG. 8 show that treatment with MOG 37-A44-52 and/or MOG 37-Q41-52 led to a marked decrease in severity and incidence of EAE induced with the native MOG 37-52, an observation associated with a markedly reduced response ex vivo to MOG 37-52 by lymph node cells isolated from treated mice.

For EAE induced in $H-2^b$ haplotype mice (C3H.SW, C57BL) by MOG 35-55 (SEQ ID NO: 234), we have defined residues 41 and 44 as crucial TCR contact residues for the interaction between the encephalitogenic nonameric core sequence MOG 40-48, found by molecular modelling studies to represent the preferred binding mode for MOG 35-55 to $IA^b$, and the TCR of $H-2^b$ MOG-specific T-cells. APLs with non-conservative substitutions at either or both of these residues elicited T-cell responses which were not encephalitogenic (not shown). In vitro, these APLs inhibited the proliferation of T-cell clones to MOG 37-52, the minimal optimal stimulatory peptide. Pilot studies of the cytokine profile of APL-specific T-cell lines suggested that the APL wherein F44 is substituted by A44 (MOG 37-A44-52) elicits Th2 T-cells (not shown), an observation commensurate with the non-encephalitogenicity of this APL, and which could play a role in immunomodulation of MOG-induced EAE. MOG35-55-specific T-cell line was raised from MOG35-55-immunized C3H.SW mice as described (Mendel et al., 1996). Cytokine assays were performed by ELISA according to PharMingen standard protocols.

Possible mechanisms by which the relevant APLs may inhibit MOG 37-52-reactive T-cell clones in vitro were tested by analyzing their effect on TCR signaling, as well as on cytokine secretion by the clones. The results indicated that MOG 37-A44-52 alone induces partial TCR signaling in the T-cell clones, suggesting that it may exert its effect via partial agonist as well as antagonist activities, which could result in anergy of the T-cells (not shown).

EXAMPLE 15

Inhibition of EAE Associated with Multiple Pathogenic Autoreactivities Requires Multiepitope-directed Immunomodulation Y-MSPb, the purified protein product of the synthetic Y-MSPb gene, disclosed in WO 01-31037, designed to encode tandemly arranged disease-relevant epitopes clusters of the encephalitogenic proteins MBP, PLP, MOG, and MOBP, was tested for its immunomodulatory effect on EAE associated with multiple pathogenic autoreactivities, upon tolerogenic administration, in the same way as described for Y-MSPa in WO 01-31037.

Figure 9A:
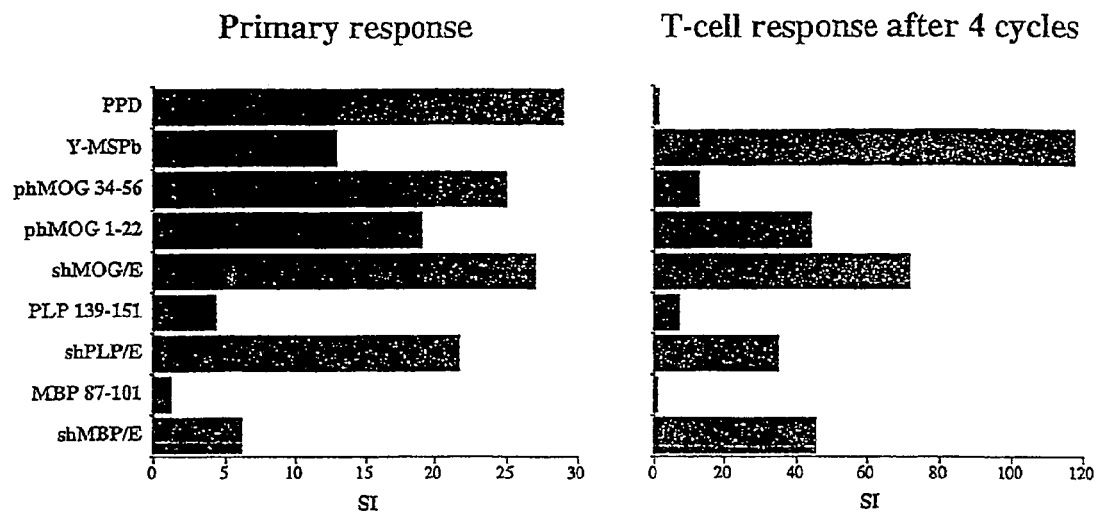
FIGS. 9A-9B show that inhibition of EAE associated with multiple pathogenic autoreactivities requires multi-epitope-directed immunomodulation. 9A. Multiantigen/epitope reactivity of Y-MSPb-reactive line T cells. 9B. EAE associated with multiple pathogenic autoreactivities induced by Y-MSPb-reactive line T-cells ($2 \times 10^{-6}$ cells, i.v., on day 0) is fully abrogated by tolerogenic administration of Y-MSPb in PBS given daily intraperitoneally (i.p.) from the day of T-cell transfer. (SI=stimulation index).

Line T-cells were selected in vitro with Y-MSPb from lymph node cells (LNCs) of (C3H.SW×SJL/J)F$_1$ mice immunized with Y-MSPb (containing encephalitogenic epitopes of MOG, MBP, PLP and MOBP) in CFA, and were analyzed after primary response (left panel) and after four cycles of selection (right panel) for their proliferative response to Y-MSPb, phMOG 34-56, phMOG 1-22, shMOG/E, PLP 139-151, shPLP/E, MBP 87-101 and shMBP/E (10 µ/ml). The proliferative response to purified protein derivative (PPD) (5 µ/ml) was analyzed as a measure of specificity. The results are shown in FIG. 9A. The line T cells are directed against each of the myelin autoantigens.

Figure 9B:
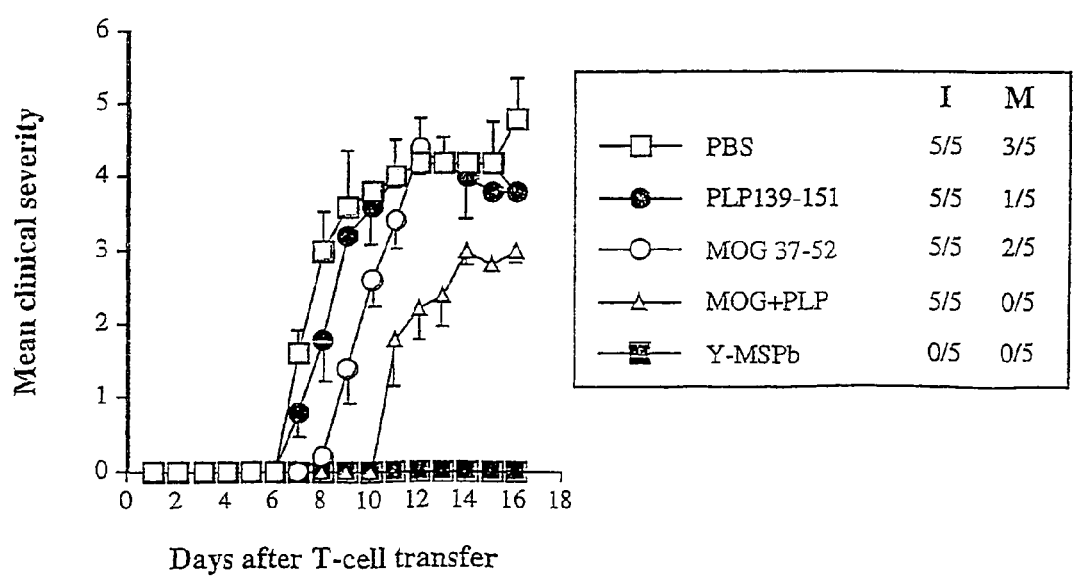

FIG. 9B shows that EAE associated with multiple pathogenic autoreactivities induced by Y-MSPb-reactive line T-cells (2×10$^{-6}$ cells, i.v., on day 0) is fully abrogated by tolerogenic administration of Y-MSPb in PBS given daily intraperitoneally (i.p.) from the day of T-cell transfer. Targeting the T-cells reacting against only one of the epitopes, MOG 37-52 or PLP139-151, recognized by the multireactive Y-MSPb-elicited line T-cells, has no significant effect on disease incidence or severity, while dual targeting with a combination of MOG 37-52 and PLP139-151 (indicated as MOG+PLP) has only a marginal effect on disease severity.

The development of EAE associated with multiple autoreactivities and induced by transfer of T-cells reactive with defined epitopes of MBP, PLP, MOG and MOBP (FIG. 9A) could also be totally suppressed by daily i.v. administration of the purified protein product of the Y-MSPb gene (FIG. 9B). The relevant PLP or MOG peptides administered singly according to the same regimen had no effect on disease development, while a combination of MOG+PLP only marginally decreased disease severity (FIG. 9B). These data strongly emphasize the necessity to neutralize as many as possible of the relevant multiple autoreactivities for effective immunomodulation of autoimmune diseases associated with a multiplicity of potential primary target antigens. In view of eventual extrapolation to therapeutic approaches for MS, concomitant multiepitope-directed immunomodulation via non-stimulatory, non-encephalitogenic APLs is likely to be a more effective, safer approach.

In the same way, the multitarget autoantigen genes of the invention Y-MSPe, ΔY-MSPe, and preferably the Y-MSP-AL and ΔY-MSP-AL genes can be tested, and their ability to immunomodulate potentially pathogenic autoreactivities against multiple epitopes of several antigens associated with MS, can be shown.

REFERENCES

Bielekova, B., Goodwin, B., Richert, N., Cortese, I., Kondo, T., Afshar, G., Gran, B., Eaton, J., Antel, J., Frank, J. A., McFarland, H. F. and Martin, R. 2000. Encephalitogenic potential of the myelin basic protein peptide (amino acids 83-99) in multiple sclerosis: Results of a phase II clinical trial with an altered peptide ligand. Nature Med. 6: 1167-1175.

Bronstein, J. M., Micevych, P. E. and Chen, K. (1997) Oligodendrocyte-specific protein (OSP) is a major component of CNS myelin. J. Neurosci. Res. 50, 713-20.

Elliott, E. A. et al. 1996. Treatment of experimental encephalomyelitis with a novel chimeric fusion protein of myelin basic protein and proteolipid protein. J. Clin. Invest. 98:1602-1612.

Evavold, B. D., Sloan-Lancaster, J. and Allen, P. M. 1994. Tickling the TCR: selective T cell functions stimulated by altered peptide ligands. Immunol. Today 14: 602-609.

Gardinier, M. V., Amiguet, P., Linington, C., and Matthieu, J.-M. (1992). Myelin/oligodendrocyte glycoprotein is a unique member of the immunoglobulin superfamily. J. Neurosci. Res. 33, 177-187.

Gaur, A., Boehme, S. A., Chalmers, D., Crowe, P. D., Pahuja, A., Ling, N., Brocke, S., Steiman, L. and Conlon, P. J. 1997. Amelioration of relapsing experimental autoimmune encephalomyelitis with altered myelin basic protein peptides involves different cellular mechanisms. J. Neuroimmunol. 74: 149-158.

Gautam, A. M., Pearson, C. I., Smilek, D. E., Steinman, L. and McDevitt, H. O. 1992. A polyalanine peptide with only five native myelin residues induces autoimmune encephalomyelitis. J. Exp. Med. 176: 605-609.

Hafler B P. 1996. A single amino acid substitution in the autoantigenic peptide alters the cytokine profile inducing protective T cells. J. Undergrad. Sci. 3: 63-69.

Kappos, L., Comi, G., Panitch, H., Oger, J., Antel, J., Conlon, P., Steinman, L. 2000. Induction of a non-encephalitogenic type 2 T helper-cell autoimmune response in multiple sclerosis after administration of an altered peptide ligand in a placebo-controlled, randomized phase II trial. Nature Med. 6: 1176-1182.

Kaye, J., N. Kerlero de Rosbo, I. Mendel, S. Flechter, M. Hoffman, I. Yust, and A. Ben-Nun. 2000. The central nervous system-specific myelin oligodendrocytic basic protein (MOBP) is encephalitogenic and a potential target antigen in multiple sclerosis. J. Neuroimmunol. 102: 189-198.

Kerlero de Rosbo, N., Hoffman, M., Mendel, I., Yust, I., Kaye, J., Bakimer, R., Flechter, S., Abramsky, O., Milo, R., Karni, A., and Ben-Nun, A. (1997). Predominance of the autoimmune response to myelin oligodendrocyte glycoprotein (MOG) in multiple sclerosis: reactivity to the extracellular domain of MOG is directed against three main regions. Eur. J. Immunol. 27, 3059-3069.

Kerlero de Rosbo, N. and Ben-Nun, A. (1998) T-cell responses to myelin antigens in multiple sclerosis. Relevance of the predominant autoimmune reactivity to myelin oligodeglycoprotein. J. Autoimmun. 11, 287-299.

Kerlero de Rosbo, N. and Ben-Nun, A. (1999) Experimental autoimmune encephalomyelitis induced by various antigens of the central nervous system. Overview and relevance to multiple sclerosis. In Shoenfeld, Y. (Ed.) The decade of autoimmunity 1987-1997. Elsevier Science, Amsterdam, pp 169-177.

Kozovska, M., Zang, Y. C. Q., Aebischer, I., Lnu, S., Rivera, V. M., Crowe, P. D., Boehme, S. A. and Zhang, J. Z. 1998. T cell recognition motifs of an immunodominant peptide of myelin basic protein in patients with multiple sclerosis: structural requirements and clinical implications. Eur. J. Immunol. 28: 1894-1901.

Kumar, V. (1998) Determinant spreading during experimental autoimmune encephalomyelitis: is it potentiating, protecting or participating in the disease? Immunol. Rev. 164, 73-80.

Leadbetter, E. A. et al. 1998. Experimental autoimmune encephalomyelitis induced with a combination of myelin basic protein and myelin oligodendrocyte glycoprotein is ameliorated by administration of a single myelin basic protein peptide. J. Immunol. 161:504-512

Sette, A. Buus, S., Colon, S., Smith, J. A., Miles, C. and Grey, H. M. 1987. Structural characteristics of an antigen required for its interaction with Ia and recognition by T cells. Nature 328: 395-399.

Singh, R. A. K., Zang, Y. C. Q., Shrivastava, A., Hong, J., Wang, G. T., Li, S., Tejada-Simon, M., Rivera, V. M. and Zhang, J. Z. 1999. Th1 and Th2 deviation of myelin-autoreactive T cells by altered peptide ligands is associated with reciprocal regulation of Lck, Fyn, and ZAP-70. J. Immunol. 163: 6393-6402.

Sloan-Lancaster, J. and Allen, P. M. 1996. Altered peptide ligand-induced partial T cell activation: Molecular mechanisms and role in T cell biology. Annu. Rev. Immunol. 14: 1-27.

Stevens, D. B., Chen, K., Seitz, R. S., Sercarz, E. E. and Bronstein, J. M. (1999) Oligodendrocyte-specific protein peptides induce experimental autoimmune encephalomyelitis in SJL/J mice. J. Immunol. 162, 7501-7509.

Tuohy, V. K. 1994. Peptide determinants of myelin proteolipid protein (PLP) in autoimmune disease: A review. Neurochem. Res. 19, 935-944.

Tuohy, V. K., Yu, M., Yin, L., Kawczak, J. A., Johnson, J. M., Mathisen, P. M., Weinstock-Guttman, B. and Kinkel, R. P. (1998) The epitope spreading cascade during progression of experimental autoimmune encephalomyelitis and multiple sclerosis. Immunol. Rev. 164, 93-100.

Windhagen, A., Scholtz, C., Hollsberg, P., Fukaura, H., Sette, A. and Hafler, D. A. 1995. Modulation of cytokine patterns of human autoreactive T cell clones by a single amino acid substitution of their peptide ligand. Immunity 2: 373-380.

Wucherpfenning, K. W., Sette, A., Southwood, S., Oseroff, C., Matsui, M., Strominger, J. L. and Hafler, D. A. 1994. Structural requirements for binding of an immunodominant myelin basic protein peptide to DR2 isotypes and for its recognition by human T cell clones. J. Exp. Med. 179: 279-290.

Yamamoto, Y., Mizuno, R., Nishimura, T., Ogawa, Y., Yoshikawa, H., Fujimura, H., Adachi, E., Kishimoto, T., Yanagihara, T., and Sakoda, S. (1994). Cloning and expression of myelin-associated oligodendrocytic basic protein. J. Biol. Chem. 269, 31725-31730.

Young D A et al. 2000. IL-4, IL-10, IL-13 and TGF-beta from an altered peptide ligand-specific Th2 cell clone down-regulate adoptive transfer od experimental autoimmune encephalomyelitis. J. Immunol. 164(7): 3563-72.

Zhong, M.-C., L. Cohen, A. Meshorer, N. Kerlero de Rosbo, and A. Ben-Nun. 2000. T-cells specific for soluble recombinant oligodendrocyte-specific protein induce severe experimental autoimmune encephalomyelitis in H-$2^b$ and H-$2^s$ mice. J. Neuroimmunol. 105: 39-45.

SEQUENCE LISTING

```
<160> NUMBER OF SEQ ID NOS: 234

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide - MOG 43-56 - containing the
      nonameric core sequence with preferred binding mode to the
      HLA-DR/DQ molecule.
<220> FEATURE:
<221> NAME/KEY: DOMAIN
<222> LOCATION: (1)..(23)
<223> OTHER INFORMATION:

<400> SEQUENCE: 1

Gly Met Glu Val Gly Trp Tyr Arg Pro Pro Phe Ser Arg Val Val His
1               5                   10                  15

Leu Tyr Arg Asn Gly Lys Asp
            20

<210> SEQ ID NO 2
<211> LENGTH: 48
<212> TYPE: PRT
<213> ORGANISM: Artificial Sequence
<220> FEATURE:
<223> OTHER INFORMATION: Synthetic peptide - MOG 67-114 - containing the
      nonameric core sequence with preferred binding mode to th
      e HLA-DR/DQ molecule
<220> FEATURE:
<221> NAME/KEY: DOMAIN
<222> LOCATION: (1)..(48)
<223> OTHER INFORMATION:

<400> SEQUENCE: 2

Gly Arg Thr Glu Leu Leu Lys Asp Ala Ile Gly Glu Gly Lys Val Thr
1               5                   10                  15

Leu Arg Ile Arg Asn Val Arg Phe Ser Asp Glu Gly Gly Phe Thr Ser
            20                  25                  30

Phe Phe Arg Asp His Ser Tyr Gln Glu Glu Ala Ala Met Glu Leu Lys
        35                  40                  45

<210> SEQ ID NO 3
<211> LENGTH: 25
<212> TYPE: PRT
<213> ORGANISM: Artificial Sequence
<220> FEATURE:
<223> OTHER INFORMATION: Synthetic peptide - MOG 3-27 - containing the
      nonameric core sequence with preferred binding mode to the
      HLA-DR/DQ molecule
<220> FEATURE:
<221> NAME/KEY: DOMAIN
<222> LOCATION: (1)..(25)
<223> OTHER INFORMATION:
```

```
<400> SEQUENCE: 3

Phe Arg Val Ile Gly Pro Arg His Pro Ile Arg Ala Leu Val Gly Asp
1               5                   10                  15

Glu Val Glu Leu Pro Ser Arg Ile Ser
            20                  25

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide - MOG 205-215 - containing
      the nonameric core sequence with preferred binding mode to the
      HLA-DR/DQ molecule
<220> FEATURE:
<221> NAME/KEY: DOMAIN
<222> LOCATION: (1)..(11)
<223> OTHER INFORMATION:

<400> SEQUENCE: 4

Arg Leu Ala Gly Gln Phe Leu Glu Glu Leu Arg
1               5                   10

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide - MBP 84-111 - containing
      the nonameric core sequence with preferred binding mode to the
      HLA-DR/DQ molecule
<220> FEATURE:
<221> NAME/KEY: DOMAIN
<222> LOCATION: (1)..(28)
<223> OTHER INFORMATION:

<400> SEQUENCE: 5

Asn Pro Val Val His Phe Phe Lys Asn Ile Val Thr Pro Arg Thr Pro
1               5                   10                  15

Pro Pro Ser Gln Gly Lys Gly Arg Gly Leu Ser Leu
            20                  25

<210> SEQ ID NO 6
<211> LENGTH: 28
<212> TYPE: PRT
<213> ORGANISM: Artificial Sequence
<220> FEATURE:
<223> OTHER INFORMATION: Synthetic peptide - MBP 141-168 - containing
      the nonameric core sequence with preferred binding mode to the
      HLA-DR/DQ molecule
<220> FEATURE:
<221> NAME/KEY: DOMAIN
<222> LOCATION: (1)..(28)
<223> OTHER INFORMATION:

<400> SEQUENCE: 6

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala
            20                  25

<210> SEQ ID NO 7
<211> LENGTH: 31
<212> TYPE: PRT
<213> ORGANISM: Artificial Sequence
<220> FEATURE:
<223> OTHER INFORMATION: Synthetic peptide - MBP 12-42 - containing
      the nonameric core sequence with preferred binding mode to the
      HLA-DR/DQ molecule
```

```
<220> FEATURE:
<221> NAME/KEY: DOMAIN
<222> LOCATION: (1)..(31)
<223> OTHER INFORMATION:

<400> SEQUENCE: 7

Ser Lys Tyr Leu Ala Thr Ala Ser Thr Met Asp His Ala Arg His Gly
1               5                   10                  15

Phe Leu Pro Arg His Arg Asp Thr Gly Ile Leu Asp Ser Ile Gly
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic peptide - OSP 42-73 - containing
      the nonameric core seq uence with preferred binding mode to the HL
      A-DR/DQ molecule
<220> FEATURE:
<221> NAME/KEY: DOMAIN
<222> LOCATION: (1)..(32)
<223> OTHER INFORMATION:

<400> SEQUENCE: 8

Lys Leu Asp Glu Leu Gly Ser Lys Gly Leu Trp Ala Asp Ser Val Met
1               5                   10                  15

Ala Thr Gly Leu Tyr His Ser Lys Pro Leu Val Asp Ile Leu Ile Leu
            20                  25                  30

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide - OSP 98-109 - containing
      the nonameric core sequence with preferred binding mode to the
      HLA-DR/DQ molecule
<220> FEATURE:
<221> NAME/KEY: DOMAIN
<222> LOCATION: (1)..(12)
<223> OTHER INFORMATION:

<400> SEQUENCE: 9

Leu Leu Thr Val Leu Pro Ser Ile Arg Met Gly Gln
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide - OSP 187-206 - containing
      the nonameric core sequence with preferred binding mode to the
      HLA-DR/DQ molecule
<220> FEATURE:
<221> NAME/KEY: DOMAIN
<222> LOCATION: (1)..(20)
<223> OTHER INFORMATION:

<400> SEQUENCE: 10

Asn Arg Phe Tyr Tyr Thr Ala Gly Ser Ser Pro Thr His Ala Lys
1               5                   10                  15

Ser Ala His Val
            20

<210> SEQ ID NO 11
<211> LENGTH: 15
<212> TYPE: PRT
```

```
<213> ORGANISM: Artificial Sequence
<220> FEATURE:
<223> OTHER INFORMATION: Synthetic peptide - OSP 192-206 - containing
      the nonameric core sequence with preferred binding mode to the
      HLA-DR/DQ molecule
<220> FEATURE:
<221> NAME/KEY: DOMAIN
<222> LOCATION: (1)..(15)
<223> OTHER INFORMATION:

<400> SEQUENCE: 11

Thr Ala Gly Ser Ser Ser Pro Thr His Ala Lys Ser Ala His Val
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic peptide - OSP 20-33 - containing
      the nonameric core seq uence with preferred binding mode to the HL
      A-DR/DQ molecule.
<220> FEATURE:
<221> NAME/KEY: DOMAIN
<222> LOCATION: (1)..(14)
<223> OTHER INFORMATION:

<400> SEQUENCE: 12

Val Ile Val Thr Thr Ser Thr Asn Asp Trp Val Val Thr Ser
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide - OSP 129-145 - containing
      the nonameric core sequence with preferred binding mode to the
      HLA-DR/DQ molecule.
<220> FEATURE:
<221> NAME/KEY: DOMAIN
<222> LOCATION: (1)..(17)
<223> OTHER INFORMATION:

<400> SEQUENCE: 13

Leu Ala Leu Ser Ala Leu Val Ala Thr Ile Trp Phe Pro Val Ser Ala
1               5                   10                  15

His

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide - MOBP 15-33 - containing
      the nonameric core sequence with preferred binding mode to the
      HLA-DR/DQ molecule.
<220> FEATURE:
<221> NAME/KEY: DOMAIN
<222> LOCATION: (1)..(19)
<223> OTHER INFORMATION:

<400> SEQUENCE: 14

Gln Lys Tyr Ser Glu His Phe Ser Ile His Ser Ser Pro Pro Phe Thr
1               5                   10                  15

Phe Leu Asn

<210> SEQ ID NO 15
<211> LENGTH: 36
<212> TYPE: PRT
```

-continued

```
<213> ORGANISM: Artificial Sequence
<220> FEATURE:
<223> OTHER INFORMATION: Synthetic peptide - MOBP 55-90 - containing
      the nonameric core sequence with preferred binding mode to the
      HLA-DR/DQ molecule.
<220> FEATURE:
<221> NAME/KEY: DOMAIN
<222> LOCATION: (1)..(36)
<223> OTHER INFORMATION:

<400> SEQUENCE: 15

Lys Glu Glu Asp Trp Ile Ser Ser Ala Ser Gln Lys Thr Arg Thr Ser
1               5                   10                  15

Arg Arg Ala Lys Ser Pro Gln Arg Pro Lys Gln Pro Ala Ala Pro
            20                  25                  30

Pro Ala Val Val
        35

<210> SEQ ID NO 16
<211> LENGTH: 17
<212> TYPE: PRT
<213> ORGANISM: Artificial Sequence
<220> FEATURE:
<223> OTHER INFORMATION: Synthetic peptide - MOBP 156-172 - containing
      the nonameric core sequence with preferred binding mode to the
      HLA-DR/DQ molecule.
<220> FEATURE:
<221> NAME/KEY: DOMAIN
<222> LOCATION: (1)..(17)
<223> OTHER INFORMATION:

<400> SEQUENCE: 16

Lys Gln Gln Pro Arg Ser Ser Pro Leu Arg Gly Pro Gly Ala Ser Arg
1               5                   10                  15

Gly

<210> SEQ ID NO 17
<211> LENGTH: 48
<212> TYPE: PRT
<213> ORGANISM: Artificial Sequence
<220> FEATURE:
<223> OTHER INFORMATION: Synthetic peptide - PLP 103-150 - containing
      the nonameric core sequence with preferred binding mode to the
      HLA-DR/DQ molecule.
<220> FEATURE:
<221> NAME/KEY: DOMAIN
<222> LOCATION: (1)..(48)
<223> OTHER INFORMATION:

<400> SEQUENCE: 17

Tyr Lys Thr Thr Ile Ser Gly Lys Gly Leu Ser Ala Thr Val Thr Gly
1               5                   10                  15

Gly Gln Lys Gly Arg Gly Ser Arg Gly Gln His Gln Ala His Ser Leu
            20                  25                  30

Glu Arg Val Ser His Ser Leu Gly Lys Trp Leu Gly His Pro Asp Lys
        35                  40                  45

<210> SEQ ID NO 18
<211> LENGTH: 27
<212> TYPE: PRT
<213> ORGANISM: Artificial Sequence
<220> FEATURE:
<223> OTHER INFORMATION: Synthetic peptide - PLP 177-203 - containing
      the nonameric core sequence with preferred binding mode to the
      HLA-DR/DQ molecule.
<220> FEATURE:
<221> NAME/KEY: DOMAIN
<222> LOCATION: (1)..(27)
<223> OTHER INFORMATION:
```

```
<400> SEQUENCE: 18

Phe Asn Thr Trp Thr Thr Ser Gln Ser Ile Ala Phe Pro Ser Lys Thr
1               5                   10                  15

Ser Ala Ser Ile Gly Ser Leu Ser Ala Asp Ala
            20                  25

<210> SEQ ID NO 19
<211> LENGTH: 23
<212> TYPE: PRT
<213> ORGANISM: Artificial Sequence
<220> FEATURE:
<223> OTHER INFORMATION: Synthetic peptide - PLP 218-240 - containing
      the nonameric core sequence with preferred binding mode to the
      HLA-DR/DQ molecule.
<220> FEATURE:
<221> NAME/KEY: DOMAIN
<222> LOCATION: (1)..(23)
<223> OTHER INFORMATION:

<400> SEQUENCE: 19

Val Ser Gly Ser Asn Leu Leu Ser Ile Ser Lys Thr Ala Glu Phe Gln
1               5                   10                  15

Met Thr Phe His Leu Phe Ile
            20

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide - 38-52 -containing the
      nonameric core sequence with preferred binding mode to the
      HLA-DR/DQ molecule.
<220> FEATURE:
<221> NAME/KEY: DOMAIN
<222> LOCATION: (1)..(15)
<223> OTHER INFORMATION:

<400> SEQUENCE: 20

Ala Leu Thr Gly Thr Glu Lys Leu Ile Glu Thr Tyr Phe Ser Lys
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide - PLP 264-276 - containing
      the nonameric core sequence with preferred binding mode to the
      HLA-DR/DQ molecule.
<220> FEATURE:
<221> NAME/KEY: DOMAIN
<222> LOCATION: (1)..(12)
<223> OTHER INFORMATION:

<400> SEQUENCE: 21

Phe Ala Val Leu Lys Met Gly Arg Gly Thr Lys Phe
1               5                   10

<210> SEQ ID NO 22
<211> LENGTH: 22
<212> TYPE: PRT
<213> ORGANISM: Artificial Sequence
<220> FEATURE:
<223> OTHER INFORMATION: Synthetic peptide - MOG 37-58 - containing
      the nonameric core seq uence which fits into the MS-relevant
      HLA-DR/DQ molecule and are flanked by 2-5 amino acids at their
      N- and C-termini.
<220> FEATURE:
```

```
<221> NAME/KEY: DOMAIN
<222> LOCATION: (1)..(22)
<223> OTHER INFORMATION:

<400> SEQUENCE: 22

Val Gly Trp Tyr Arg Pro Pro Phe Ser Arg Val Val His Leu Tyr Arg
1               5                   10                  15

Asn Gly Lys Asp Gln Asp
            20

<210> SEQ ID NO 23
<211> LENGTH: 31
<212> TYPE: PRT
<213> ORGANISM: Artificial Sequence
<220> FEATURE:
<223> OTHER INFORMATION: Synthetic peptide - MOG 65-95 - containing
      the nonameric core seq uence which fits into the MS-relevant
      HLA-DR/DQ molecule and are flanked by 2-5 amino acids at their
      N- and C-termini.
<220> FEATURE:
<221> NAME/KEY: DOMAIN
<222> LOCATION: (1)..(31)
<223> OTHER INFORMATION:

<400> SEQUENCE: 23

Tyr Arg Gly Arg Thr Glu Leu Leu Lys Asp Ala Ile Gly Glu Gly Lys
1               5                   10                  15

Val Thr Leu Arg Ile Arg Asn Val Arg Phe Ser Asp Glu Gly Gly
            20                  25                  30

<210> SEQ ID NO 24
<211> LENGTH: 26
<212> TYPE: PRT
<213> ORGANISM: Artificial Sequence
<220> FEATURE:
<223> OTHER INFORMATION: Synthetic peptide - MOG 7-32 - containing
      the nonameric core sequ ence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(26)
<223> OTHER INFORMATION:

<400> SEQUENCE: 24

Gly Pro Arg His Pro Ile Arg Ala Leu Val Gly Asp Glu Val Glu Leu
1               5                   10                  15

Arg Cys Arg Ile Ser Pro Gly Lys Asn Ala
            20                  25

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide - MOG 202-218 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(17)
<223> OTHER INFORMATION:

<400> SEQUENCE: 25

Leu His Arg Arg Leu Ala Gly Gln Phe Leu Glu Glu Leu Arg Asn Pro
1               5                   10                  15

Phe
```

<210> SEQ ID NO 26
<211> LENGTH: 22
<212> TYPE: PRT
<213> ORGANISM: Artificial Sequence
<220> FEATURE:
<223> OTHER INFORMATION: Synthetic peptide - MBP 82-103 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(22)
<223> OTHER INFORMATION:

<400> SEQUENCE: 26

Asp Glu Asn Pro Val Val His Phe Phe Lys Asn Ile Val Thr Pro Arg
1               5                   10                  15

Thr Pro Pro Pro Ser Gln
            20

<210> SEQ ID NO 27
<211> LENGTH: 21
<212> TYPE: PRT
<213> ORGANISM: Artificial Sequence
<220> FEATURE:
<223> OTHER INFORMATION: Synthetic peptide - MBP 136-156 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(21)
<223> OTHER INFORMATION:

<400> SEQUENCE: 27

Ser Ala His Lys Gly Phe Lys Gly Val Asp Ala Gln Gly Thr Leu Ser
1               5                   10                  15

Lys Ile Phe Lys Leu
            20

<210> SEQ ID NO 28
<211> LENGTH: 23
<212> TYPE: PRT
<213> ORGANISM: Artificial Sequence
<220> FEATURE:
<223> OTHER INFORMATION: Synthetic peptide - MBP 148-170 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(23)
<223> OTHER INFORMATION:

<400> SEQUENCE: 28

Gly Thr Leu Ser Lys Ile Phe Lys Leu Gly Gly Arg Asp Ser Arg Ser
1               5                   10                  15

Gly Ser Pro Met Ala Arg Arg
            20

<210> SEQ ID NO 29
<211> LENGTH: 23
<212> TYPE: PRT
<213> ORGANISM: Artificial Sequence
<220> FEATURE:
<223> OTHER INFORMATION: Synthetic peptide - MBP 7-29 - containing the
      nonameric core sequence which fits into the MS-relevant HLA-DR/DQ
      molecule and are flanked by 2-5 amino acids at their N- and
      C-termini
<220> FEATURE:

```
<221> NAME/KEY: DOMAIN
<222> LOCATION: (1)..(23)
<223> OTHER INFORMATION:

<400> SEQUENCE: 29

Ser Gln Arg His Gly Ser Lys Tyr Leu Ala Thr Ala Ser Thr Met Asp
1               5                   10                  15

His Ala Arg His Gly Phe Leu
            20

<210> SEQ ID NO 30
<211> LENGTH: 21
<212> TYPE: PRT
<213> ORGANISM: Artificial Sequence
<220> FEATURE:
<223> OTHER INFORMATION: Synthetic peptide - MBP 25-45 - containing the
      nonameric core sequence which fits into the MS-relevant HLA-DR/DQ
      molecule and are flanked by 2-5 amino acids at their N- and
      C-termini
<220> FEATURE:
<221> NAME/KEY: DOMAIN
<222> LOCATION: (1)..(21)
<223> OTHER INFORMATION:

<400> SEQUENCE: 30

Arg His Gly Phe Leu Pro Arg His Arg Asp Thr Gly Ile Leu Asp Ser
1               5                   10                  15

Ile Gly Arg Phe Phe
            20

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide - OSP 38-64 - containing the
      nonameric core sequence which fits into the MS-relevant
      HLA-DR/DQ molecule and are flanked by 2-5 amino acids at their N-
      and C-termini
<220> FEATURE:
<221> NAME/KEY: DOMAIN
<222> LOCATION: (1)..(30)
<223> OTHER INFORMATION:

<400> SEQUENCE: 31

Ser Lys Gly Leu Trp Ala Asp Cys Val Met Ala Thr Gly Leu Tyr His
1               5                   10                  15

Cys Lys Pro Leu Val Asp Ile Leu Ile Leu Pro Gly Tyr Val
            20                  25                  30

<210> SEQ ID NO 32
<211> LENGTH: 27
<212> TYPE: PRT
<213> ORGANISM: Artificial Sequence
<220> FEATURE:
<223> OTHER INFORMATION: Synthetic peptide - OSP 48-77 - containing the
      nonameric core sequence which fits into the MS-relevant HLA-DR/DQ
      molecule and are flanked by 2-5 amino acids at their N- and
      C-termini
<220> FEATURE:
<221> NAME/KEY: DOMAIN
<222> LOCATION: (1)..(27)
<223> OTHER INFORMATION:

<400> SEQUENCE: 32

Pro Thr Cys Arg Lys Leu Asp Glu Leu Gly Ser Lys Gly Leu Trp Ala
1               5                   10                  15

Asp Cys Val Met Ala Thr Gly Leu Tyr His Cys
            20                  25
```

```
<210> SEQ ID NO 33
<211> LENGTH: 19
<212> TYPE: PRT
<213> ORGANISM: Artificial Sequence
<220> FEATURE:
<223> OTHER INFORMATION: Synthetic peptide - OSP 94-112 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(19)
<223> OTHER INFORMATION:

<400> SEQUENCE: 33

Ala Ile Leu Leu Leu Leu Thr Val Leu Pro Cys Ile Arg Met Gly Gln
1               5                   10                  15

Glu Pro Gly

<210> SEQ ID NO 34
<211> LENGTH: 22
<212> TYPE: PRT
<213> ORGANISM: Artificial Sequence
<220> FEATURE:
<223> OTHER INFORMATION: Synthetic peptide - OSP 17-38 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(22)
<223> OTHER INFORMATION:

<400> SEQUENCE: 34

Trp Ile Gly Val Ile Val Thr Thr Ser Thr Asn Asp Trp Val Val Thr
1               5                   10                  15

Cys Gly Tyr Thr Ile Pro
            20

<210> SEQ ID NO 35
<211> LENGTH: 27
<212> TYPE: PRT
<213> ORGANISM: Artificial Sequence
<220> FEATURE:
<223> OTHER INFORMATION: Synthetic peptide - OSP 124-150 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(27)
<223> OTHER INFORMATION:

<400> SEQUENCE: 35

Val Leu Leu Ile Leu Leu Ala Leu Cys Ala Leu Val Ala Thr Ile Trp
1               5                   10                  15

Phe Pro Val Cys Ala His Arg Glu Thr Thr Ile
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic peptide - MOBP 13-38 - containing
      the nonameric core sequence which fits into the MS-relevant
      HLA-DR/DQ molecule and are flanked by 2-5 amino acids at their
      N- and C-termini
<220> FEATURE:
```

```
<221> NAME/KEY: DOMAIN
<222> LOCATION: (1)..(26)
<223> OTHER INFORMATION:

<400> SEQUENCE: 36

Lys Asn Gln Lys Tyr Ser Glu His Phe Ser Ile His Cys Cys Pro Pro
1               5                   10                  15

Phe Thr Phe Leu Asn Ser Lys Lys Glu Ile
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic peptide - MOBP 54-80 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(27)
<223> OTHER INFORMATION:

<400> SEQUENCE: 37

Gln Lys Glu Glu Asp Trp Thr Cys Cys Ala Cys Gln Lys Thr Arg Thr
1               5                   10                  15

Ser Arg Arg Ala Lys Ser Pro Gln Arg Pro Lys
            20                  25

<210> SEQ ID NO 38
<211> LENGTH: 18
<212> TYPE: PRT
<213> ORGANISM: Artificial Sequence
<220> FEATURE:
<223> OTHER INFORMATION: Synthetic peptide - MOBP 72-89 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(18)
<223> OTHER INFORMATION:

<400> SEQUENCE: 38

Arg Ala Lys Ser Pro Gln Arg Pro Lys Gln Gln Pro Ala Ala Pro Pro
1               5                   10                  15

Ala Val

<210> SEQ ID NO 39
<211> LENGTH: 19
<212> TYPE: PRT
<213> ORGANISM: Artificial Sequence
<220> FEATURE:
<223> OTHER INFORMATION: Synthetic peptide - MOBP 156-174 - containing
      the nonameric coresequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(19)
<223> OTHER INFORMATION:

<400> SEQUENCE: 39

Lys Gln Gln Pro Arg Ser Ser Pro Leu Arg Gly Pro Gly Ala Ser Arg
1               5                   10                  15

Gly Gly Ser
```

```
<210> SEQ ID NO 40
<211> LENGTH: 21
<212> TYPE: PRT
<213> ORGANISM: Artificial Sequence
<220> FEATURE:
<223> OTHER INFORMATION: Synthetic peptide - PLP 102-122 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(21)
<223> OTHER INFORMATION:

<400> SEQUENCE: 40

Asp Tyr Lys Thr Thr Ile Cys Gly Lys Gly Leu Ser Ala Thr Val Thr
1               5                   10                  15

Gly Gly Gln Lys Gly
            20

<210> SEQ ID NO 41
<211> LENGTH: 31
<212> TYPE: PRT
<213> ORGANISM: Artificial Sequence
<220> FEATURE:
<223> OTHER INFORMATION: Synthetic peptide - PLP 120-150 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(31)
<223> OTHER INFORMATION:

<400> SEQUENCE: 41

Gln Lys Gly Arg Gly Ser Arg Gly Gln His Gln Ala His Ser Leu Glu
1               5                   10                  15

Arg Val Cys His Cys Leu Gly Lys Trp Leu Gly His Pro Asp Lys
            20                  25                  30

<210> SEQ ID NO 42
<211> LENGTH: 28
<212> TYPE: PRT
<213> ORGANISM: Artificial Sequence
<220> FEATURE:
<223> OTHER INFORMATION: Synthetic peptide - PLP 173-200 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(28)
<223> OTHER INFORMATION:

<400> SEQUENCE: 42

Val Tyr Ile Tyr Phe Asn Thr Trp Thr Thr Cys Gln Ser Ile Ala Phe
1               5                   10                  15

Pro Ser Lys Thr Ser Ala Ser Ile Gly Ser Leu Cys
            20                  25

<210> SEQ ID NO 43
<211> LENGTH: 19
<212> TYPE: PRT
<213> ORGANISM: Artificial Sequence
<220> FEATURE:
<223> OTHER INFORMATION: Synthetic peptide - PLP 190-208 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
```

```
<222> LOCATION: (1)..(19)
<223> OTHER INFORMATION:

<400> SEQUENCE: 43

Ser Lys Thr Ser Ala Ser Ile Gly Ser Leu Cys Ala Asp Ala Arg Met
1               5                   10                  15

Tyr Gly Val

<210> SEQ ID NO 44
<211> LENGTH: 22
<212> TYPE: PRT
<213> ORGANISM: Artificial Sequence
<220> FEATURE:
<223> OTHER INFORMATION: Synthetic peptide - PLP 185-206 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(22)
<223> OTHER INFORMATION:

<400> SEQUENCE: 44

Ser Ile Ala Phe Pro Ser Lys Thr Ser Ala Ser Ile Gly Ser Leu Cys
1               5                   10                  15

Ala Asp Ala Arg Met Tyr
            20

<210> SEQ ID NO 45
<211> LENGTH: 31
<212> TYPE: PRT
<213> ORGANISM: Artificial Sequence
<220> FEATURE:
<223> OTHER INFORMATION: Synthetic peptide - PLP 213-243 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(31)
<223> OTHER INFORMATION:

<400> SEQUENCE: 45

Ala Phe Pro Gly Lys Val Cys Gly Ser Asn Leu Leu Ser Ile Cys Lys
1               5                   10                  15

Thr Ala Glu Phe Gln Met Thr Phe His Leu Phe Ile Ala Ala Phe
            20                  25                  30

<210> SEQ ID NO 46
<211> LENGTH: 16
<212> TYPE: PRT
<213> ORGANISM: Artificial Sequence
<220> FEATURE:
<223> OTHER INFORMATION: Synthetic peptide - PLP 35-57 - containing
      the nonameric core  sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(16)
<223> OTHER INFORMATION:

<400> SEQUENCE: 46

Thr Tyr Asn Phe Ala Val Leu Lys Leu Met Gly Arg Gly Thr Lys Phe
1               5                   10                  15

<210> SEQ ID NO 47
<211> LENGTH: 23
<212> TYPE: PRT
```

```
<213> ORGANISM: Artificial Sequence
<220> FEATURE:
<223> OTHER INFORMATION: Synthetic peptide - PLP 261-276 - containing
      the nonameric core sequence which fits into the MS-relevant
      HLA-DR/DQ molecule and are flanked by 2-5 amino acids at their
      N- and C-termini
<220> FEATURE:
<221> NAME/KEY: DOMAIN
<222> LOCATION: (1)..(23)
<223> OTHER INFORMATION:

<400> SEQUENCE: 47

Gly His Glu Ala Leu Thr Gly Thr Glu Lys Leu Ile Glu Thr Tyr Phe
1               5                   10                  15

Ser Lys Asn Tyr Gln Asp Tyr
            20

<210> SEQ ID NO 48
<211> LENGTH: 22
<212> TYPE: PRT
<213> ORGANISM: Artificial Sequence
<220> FEATURE:
<223> OTHER INFORMATION: The peptide of SEQ ID NO: 22 in which the
      residues at positions 7 and 13 were replaced by Ala
<220> FEATURE:
<221> NAME/KEY: DOMAIN
<222> LOCATION: (1)..(22)
<223> OTHER INFORMATION:

<400> SEQUENCE: 48

Val Gly Trp Tyr Arg Pro Ala Phe Ser Arg Val Val Ala Leu Tyr Arg
1               5                   10                  15

Asn Gly Lys Asp Gln Asp
            20

<210> SEQ ID NO 49
<211> LENGTH: 19
<212> TYPE: PRT
<213> ORGANISM: Artificial Sequence
<220> FEATURE:
<223> OTHER INFORMATION: The peptide of SEQ ID NO: 22 in which the
      residue at position 10 was replaced by Ala and the three residues
      at the C-terminus are lacking
<220> FEATURE:
<221> NAME/KEY: DOMAIN
<222> LOCATION: (1)..(19)
<223> OTHER INFORMATION:

<400> SEQUENCE: 49

Val Gly Trp Tyr Arg Pro Pro Phe Ser Ala Val Val His Leu Tyr Arg
1               5                   10                  15

Asn Gly Lys

<210> SEQ ID NO 50
<211> LENGTH: 31
<212> TYPE: PRT
<213> ORGANISM: Artificial Sequence
<220> FEATURE:
<223> OTHER INFORMATION: The peptide of SEQ ID NO: 23 in which the
      residues at positions 9, 17, 22 were replaced by Ala.
<220> FEATURE:
<221> NAME/KEY: DOMAIN
<222> LOCATION: (1)..(31)
<223> OTHER INFORMATION:

<400> SEQUENCE: 50

Tyr Arg Gly Arg Thr Glu Leu Leu Ala Asp Ala Ile Gly Glu Gly Lys
1               5                   10                  15

Ala Thr Leu Arg Ile Ala Asn Val Arg Phe Ser Asp Glu Gly Gly
```

```
<210> SEQ ID NO 51
<211> LENGTH: 20
<212> TYPE: PRT
<213> ORGANISM: Artificial Sequence
<220> FEATURE:
<223> OTHER INFORMATION: The peptide of SEQ ID NO: 23 in which the
      residues at positions 6 and 11 were replaced by Ala, 12 residues
      at the N-terminus are lacking, and having additional Phe at the
      C-terminus
<220> FEATURE:
<221> NAME/KEY: DOMAIN
<222> LOCATION: (1)..(20)
<223> OTHER INFORMATION:

<400> SEQUENCE: 51

Gly Glu Gly Lys Val Ala Leu Arg Ile Arg Ala Val Arg Phe Ser Asp
1               5                   10                  15

Glu Gly Gly Phe
            20

<210> SEQ ID NO 52
<211> LENGTH: 26
<212> TYPE: PRT
<213> ORGANISM: Artificial Sequence
<220> FEATURE:
<223> OTHER INFORMATION: The peptide of SEQ ID NO: 24 in which the
      residues at positions 7 and 17 were replaced by Ala
<220> FEATURE:
<221> NAME/KEY: DOMAIN
<222> LOCATION: (1)..(26)
<223> OTHER INFORMATION:

<400> SEQUENCE: 52

Gly Pro Arg His Pro Ile Ala Ala Leu Val Gly Asp Glu Val Glu Leu
1               5                   10                  15

Ala Cys Arg Ile Ser Pro Gly Lys Asn Ala
            20                  25

<210> SEQ ID NO 53
<211> LENGTH: 17
<212> TYPE: PRT
<213> ORGANISM: Artificial Sequence
<220> FEATURE:
<223> OTHER INFORMATION: The peptide of SEQ ID NO: 25 in which the
      residue at position 9 was replaced by Ala.
<220> FEATURE:
<221> NAME/KEY: DOMAIN
<222> LOCATION: (1)..(17)
<223> OTHER INFORMATION:

<400> SEQUENCE: 53

Leu His Arg Arg Leu Ala Gly Gln Ala Leu Glu Glu Leu Arg Asn Pro
1               5                   10                  15

Phe

<210> SEQ ID NO 54
<211> LENGTH: 22
<212> TYPE: PRT
<213> ORGANISM: Artificial Sequence
<220> FEATURE:
<223> OTHER INFORMATION: The peptide of SEQ ID NO: 26 in which the
      residue at position 10 was replaced by Ala.
<220> FEATURE:
<221> NAME/KEY: DOMAIN
<222> LOCATION: (1)..(22)
<223> OTHER INFORMATION:

<400> SEQUENCE: 54
```

```
Asp Glu Asn Pro Val Val His Phe Phe Ala Asn Ile Val Thr Pro Arg
1               5                   10                  15

Thr Pro Pro Pro Ser Gln
            20
```

<210> SEQ ID NO 55
<211> LENGTH: 21
<212> TYPE: PRT
<213> ORGANISM: Artificial Sequence
<220> FEATURE:
<223> OTHER INFORMATION: The peptide of SEQ ID NO: 26 in which the
      residues at positions 6 and 12 were replaced by Ala, and one
      residue at the N-terminus is lacking.
<220> FEATURE:
<221> NAME/KEY: DOMAIN
<222> LOCATION: (1)..(21)
<223> OTHER INFORMATION:

<400> SEQUENCE: 55

```
Glu Asn Pro Val Val Ala Phe Phe Lys Asn Ile Ala Thr Pro Arg Thr
1               5                   10                  15

Pro Pro Pro Ser Gln
            20
```

<210> SEQ ID NO 56
<211> LENGTH: 21
<212> TYPE: PRT
<213> ORGANISM: Artificial Sequence
<220> FEATURE:
<223> OTHER INFORMATION: The peptide of SEQ ID NO: 27 in which the
      residue at position 10 was replaced by Ala.
<220> FEATURE:
<221> NAME/KEY: DOMAIN
<222> LOCATION: (1)..(21)
<223> OTHER INFORMATION:

<400> SEQUENCE: 56

```
Ser Ala His Lys Gly Phe Lys Gly Val Ala Ala Gln Gly Thr Leu Ser
1               5                   10                  15

Lys Ile Phe Lys Leu
            20
```

<210> SEQ ID NO 57
<211> LENGTH: 23
<212> TYPE: PRT
<213> ORGANISM: Artificial Sequence
<220> FEATURE:
<223> OTHER INFORMATION: The peptide of SEQ ID NO: 28 in which the
      residues at positions 7 and 13 were replaced by Ala.
<220> FEATURE:
<221> NAME/KEY: DOMAIN
<222> LOCATION: (1)..(23)
<223> OTHER INFORMATION:

<400> SEQUENCE: 57

```
Gly Thr Leu Ser Lys Ile Ala Lys Leu Gly Gly Arg Ala Ser Arg Ser
1               5                   10                  15

Gly Ser Pro Met Ala Arg Arg
            20
```

<210> SEQ ID NO 58
<211> LENGTH: 23
<212> TYPE: PRT
<213> ORGANISM: Artificial Sequence
<220> FEATURE:
<223> OTHER INFORMATION: The peptide of SEQ ID NO: 27 in which the
      residues at positions 7 and 14 were replaced by Ala, and having
      additional 2 residues at the C-terminus.

```
<220> FEATURE:
<221> NAME/KEY: DOMAIN
<222> LOCATION: (1)..(23)
<223> OTHER INFORMATION:

<400> SEQUENCE: 58

Ser Ala His Lys Gly Phe Ala Gly Val Asp Ala Gln Gly Ala Leu Ser
1               5                   10                  15

Lys Ile Phe Lys Leu Gly Gly
            20

<210> SEQ ID NO 59
<211> LENGTH: 23
<212> TYPE: PRT
<213> ORGANISM: Artificial Sequence
<220> FEATURE:
<223> OTHER INFORMATION: The peptide of SEQ ID NO: 29 in which the
      residues at positions 7 and 17 were replaced by Ala.
<220> FEATURE:
<221> NAME/KEY: DOMAIN
<222> LOCATION: (1)..(23)
<223> OTHER INFORMATION:

<400> SEQUENCE: 59

Ser Gln Arg His Gly Ser Ala Tyr Leu Ala Thr Ala Ser Thr Met Asp
1               5                   10                  15

Ala Ala Arg His Gly Phe Leu
            20

<210> SEQ ID NO 60
<211> LENGTH: 21
<212> TYPE: PRT
<213> ORGANISM: Artificial Sequence
<220> FEATURE:
<223> OTHER INFORMATION: The peptide of SEQ ID NO: 30 in which the
      residue at position 10 was replaced by Ala.
<220> FEATURE:
<221> NAME/KEY: DOMAIN
<222> LOCATION: (1)..(21)
<223> OTHER INFORMATION:

<400> SEQUENCE: 60

Arg His Gly Phe Leu Pro Arg His Arg Ala Thr Gly Ile Leu Asp Ser
1               5                   10                  15

Ile Gly Arg Phe Phe
            20

<210> SEQ ID NO 61
<211> LENGTH: 19
<212> TYPE: PRT
<213> ORGANISM: Artificial Sequence
<220> FEATURE:
<223> OTHER INFORMATION: The peptide of SEQ ID NO: 30 in which the
      residue at position 7 was replaced by Ala, and 2 residues at the
      N-terminus are lacking
      .
<220> FEATURE:
<221> NAME/KEY: DOMAIN
<222> LOCATION: (1)..(19)
<223> OTHER INFORMATION:

<400> SEQUENCE: 61

Gly Phe Leu Pro Arg His Ala Asp Thr Gly Ile Leu Asp Ser Ile Gly
1               5                   10                  15

Arg Phe Phe

<210> SEQ ID NO 62
<211> LENGTH: 30
```

```
<212> TYPE: PRT
<213> ORGANISM: Artificial Sequence
<220> FEATURE:
<223> OTHER INFORMATION: The peptide of SEQ ID NO: 31 in which the
      residues at positions 5, 10, 16 and 21 were replaced by Ala.
<220> FEATURE:
<221> NAME/KEY: DOMAIN
<222> LOCATION: (1)..(30)
<223> OTHER INFORMATION:

<400> SEQUENCE: 62

Ser Lys Gly Leu Ala Ala Asp Cys Val Ala Ala Thr Gly Leu Tyr Ala
1               5                   10                  15

Cys Lys Pro Leu Ala Asp Ile Leu Ile Leu Pro Gly Tyr Val
            20                  25                  30

<210> SEQ ID NO 63
<211> LENGTH: 27
<212> TYPE: PRT
<213> ORGANISM: Artificial Sequence
<220> FEATURE:
<223> OTHER INFORMATION: The peptide of SEQ ID NO: 32 in which the
      residues at positions 7, 15, 20 and 26 were replaced by Ala.
<220> FEATURE:
<221> NAME/KEY: DOMAIN
<222> LOCATION: (1)..(27)
<223> OTHER INFORMATION:

<400> SEQUENCE: 63

Pro Thr Cys Arg Lys Leu Ala Glu Leu Gly Ser Lys Gly Leu Ala Ala
1               5                   10                  15

Asp Cys Val Ala Ala Thr Gly Leu Tyr Ala Cys
            20                  25

<210> SEQ ID NO 64
<211> LENGTH: 26
<212> TYPE: PRT
<213> ORGANISM: Artificial Sequence
<220> FEATURE:
<223> OTHER INFORMATION: The peptide of SEQ ID NO: 32 in which the
      residues at positions 6, 11 and 16 were replaced by Ala and one
      residue at the N-terminus is lacking.
<220> FEATURE:
<221> NAME/KEY: DOMAIN
<222> LOCATION: (1)..(26)
<223> OTHER INFORMATION:

<400> SEQUENCE: 64

Thr Cys Arg Lys Leu Ala Glu Leu Gly Ser Ala Gly Leu Trp Ala Ala
1               5                   10                  15

Cys Val Met Ala Thr Gly Leu Tyr His Cys
            20                  25

<210> SEQ ID NO 65
<211> LENGTH: 19
<212> TYPE: PRT
<213> ORGANISM: Artificial Sequence
<220> FEATURE:
<223> OTHER INFORMATION: The peptide of SEQ ID NO: 33 in which the
      residues at position 10 was replaced by Ala.
<220> FEATURE:
<221> NAME/KEY: DOMAIN
<222> LOCATION: (1)..(19)
<223> OTHER INFORMATION:

<400> SEQUENCE: 65

Ala Ile Leu Leu Leu Leu Thr Val Leu Ala Cys Ile Arg Met Gly Gln
1               5                   10                  15

Glu Pro Gly
```

```
<210> SEQ ID NO 66
<211> LENGTH: 20
<212> TYPE: PRT
<213> ORGANISM: Artificial Sequence
<220> FEATURE:
<223> OTHER INFORMATION: The peptide of SEQ ID NO: 10 in which the
      residues at positions 10 and 16 were replaced by Ala.
<220> FEATURE:
<221> NAME/KEY: DOMAIN
<222> LOCATION: (1)..(20)
<223> OTHER INFORMATION:

<400> SEQUENCE: 66

Asn Arg Phe Tyr Tyr Thr Ala Gly Ser Ala Ser Pro Thr His Ala Ala
1               5                   10                  15

Ser Ala His Val
            20

<210> SEQ ID NO 67
<211> LENGTH: 15
<212> TYPE: PRT
<213> ORGANISM: Artificial Sequence
<220> FEATURE:
<223> OTHER INFORMATION: The peptide of SEQ ID NO: 10 in which
      the residue at position 9 was replaced by Ala and 5 residues at
      the N-terminus are lacking.
<220> FEATURE:
<221> NAME/KEY: DOMAIN
<222> LOCATION: (1)..(15)
<223> OTHER INFORMATION:

<400> SEQUENCE: 67

Thr Ala Gly Ser Ser Ser Pro Thr Ala Ala Lys Ser Ala His Val
1               5                   10                  15

<210> SEQ ID NO 68
<211> LENGTH: 22
<212> TYPE: PRT
<213> ORGANISM: Artificial Sequence
<220> FEATURE:
<223> OTHER INFORMATION: The peptide of SEQ ID NO: 34 in which the
      residue at position 10 was replaced by Ala.
<220> FEATURE:
<221> NAME/KEY: DOMAIN
<222> LOCATION: (1)..(22)
<223> OTHER INFORMATION:

<400> SEQUENCE: 68

Trp Ile Gly Val Ile Val Thr Thr Ser Ala Asn Asp Trp Val Val Thr
1               5                   10                  15

Cys Gly Tyr Thr Ile Pro
            20

<210> SEQ ID NO 69
<211> LENGTH: 27
<212> TYPE: PRT
<213> ORGANISM: Artificial Sequence
<220> FEATURE:
<223> OTHER INFORMATION: The peptide of SEQ ID NO: 35 in which the
      residues at positions 8 and 18 were replaced by Ala.
<220> FEATURE:
<221> NAME/KEY: DOMAIN
<222> LOCATION: (1)..(27)
<223> OTHER INFORMATION:

<400> SEQUENCE: 69

Val Leu Leu Ile Leu Leu Ala Ala Cys Ala Leu Val Ala Thr Ile Trp
1               5                   10                  15
```

```
Phe Ala Val Cys Ala His Arg Glu Thr Thr Ile
            20                  25
```

```
<210> SEQ ID NO 70
<211> LENGTH: 26
<212> TYPE: PRT
<213> ORGANISM: Artificial Sequence
<220> FEATURE:
<223> OTHER INFORMATION: The peptide of SEQ ID NO: 36 in which the
      residues at positions 7 and 17 were replaced by Ala.
<220> FEATURE:
<221> NAME/KEY: DOMAIN
<222> LOCATION: (1)..(26)
<223> OTHER INFORMATION:

<400> SEQUENCE: 70

Lys Asn Gln Lys Tyr Ser Ala His Phe Ser Ile His Cys Cys Pro Pro
1               5                   10                  15

Ala Thr Phe Leu Asn Ser Lys Lys Glu Ile
            20                  25
```

```
<210> SEQ ID NO 71
<211> LENGTH: 26
<212> TYPE: PRT
<213> ORGANISM: Artificial Sequence
<220> FEATURE:
<223> OTHER INFORMATION: The peptide of SEQ ID NO: 37 in which the
      residues at positions 6, 12 and 17 were replaced by Ala and one
      residue at the N-terminus is lacking.

<400> SEQUENCE: 71

Lys Glu Glu Asp Trp Ala Cys Cys Ala Cys Gln Ala Thr Arg Thr Ser
1               5                   10                  15

Ala Arg Ala Lys Ser Pro Gln Arg Pro Lys
            20                  25
```

```
<210> SEQ ID NO 72
<211> LENGTH: 19
<212> TYPE: PRT
<213> ORGANISM: Artificial Sequence
<220> FEATURE:
<223> OTHER INFORMATION: The peptide of SEQ ID NO: 39 in which the
      residue at position 10 was replaced by Ala.
<220> FEATURE:
<221> NAME/KEY: DOMAIN
<222> LOCATION: (1)..(19)
<223> OTHER INFORMATION:

<400> SEQUENCE: 72

Lys Gln Gln Pro Arg Ser Ser Pro Leu Ala Gly Pro Gly Ala Ser Arg
1               5                   10                  15

Gly Gly Ser
```

```
<210> SEQ ID NO 73
<211> LENGTH: 18
<212> TYPE: PRT
<213> ORGANISM: Artificial Sequence
<220> FEATURE:
<223> OTHER INFORMATION: The peptide of SEQ ID NO: 38 in which the
 residue at position 9
      was replaced by Ala.
<220> FEATURE:
<221> NAME/KEY: DOMAIN
<222> LOCATION: (1)..(18)
<223> OTHER INFORMATION:

<400> SEQUENCE: 73

Arg Ala Lys Ser Pro Gln Arg Pro Ala Gln Gln Pro Ala Ala Pro Pro
1               5                   10                  15
```

Ala Val

<210> SEQ ID NO 74
<211> LENGTH: 21
<212> TYPE: PRT
<213> ORGANISM: Artificial Sequence
<220> FEATURE:
<223> OTHER INFORMATION: The peptide of SEQ ID NO: 40 in which the
      residue at position 9 was replaced by Ala.
<220> FEATURE:
<221> NAME/KEY: DOMAIN
<222> LOCATION: (1)..(21)
<223> OTHER INFORMATION:

<400> SEQUENCE: 74

Asp Tyr Lys Thr Thr Ile Cys Gly Ala Gly Leu Ser Ala Thr Val Thr
1               5                   10                  15

Gly Gly Gln Lys Gly
            20

<210> SEQ ID NO 75
<211> LENGTH: 21
<212> TYPE: PRT
<213> ORGANISM: Artificial Sequence
<220> FEATURE:
<223> OTHER INFORMATION: The peptide of SEQ ID NO: 40 in which the
      residue at position 11 was replaced by Ala.
<220> FEATURE:
<221> NAME/KEY: DOMAIN
<222> LOCATION: (1)..(21)
<223> OTHER INFORMATION:

<400> SEQUENCE: 75

Asp Tyr Lys Thr Thr Ile Cys Gly Lys Gly Ala Ser Ala Thr Val Thr
1               5                   10                  15

Gly Gly Gln Lys Gly
            20

<210> SEQ ID NO 76
<211> LENGTH: 31
<212> TYPE: PRT
<213> ORGANISM: Artificial Sequence
<220> FEATURE:
<223> OTHER INFORMATION: The peptide of SEQ ID NO: 41 in which the
      residues at positions 10, 15 and 25 were replaced by Ala.
<220> FEATURE:
<221> NAME/KEY: DOMAIN
<222> LOCATION: (1)..(31)
<223> OTHER INFORMATION:

<400> SEQUENCE: 76

Gln Lys Gly Arg Gly Ser Arg Gly Gln Ala Gln Ala His Ser Ala Glu
1               5                   10                  15

Arg Val Cys His Cys Leu Gly Lys Ala Leu Gly His Pro Asp Lys
                20                  25                  30

<210> SEQ ID NO 77
<211> LENGTH: 28
<212> TYPE: PRT
<213> ORGANISM: Artificial Sequence
<220> FEATURE:
<223> OTHER INFORMATION: The peptide of SEQ ID NO: 42 in which the
      residues at positions 10 and 19 were replaced by Ala.
<220> FEATURE:
<221> NAME/KEY: DOMAIN
<222> LOCATION: (1)..(28)
<223> OTHER INFORMATION:

<400> SEQUENCE: 77

```
Val Tyr Ile Tyr Phe Asn Thr Trp Thr Ala Cys Gln Ser Ile Ala Phe
1               5                   10                  15

Pro Ser Ala Thr Ser Ala Ser Ile Gly Ser Leu Cys
            20                  25
```

```
<210> SEQ ID NO 78
<211> LENGTH: 19
<212> TYPE: PRT
<213> ORGANISM: Artificial Sequence
<220> FEATURE:
<223> OTHER INFORMATION: The peptide of SEQ ID NO: 43 in which the
      residue at position 10 was replaced by Ala.
<220> FEATURE:
<221> NAME/KEY: DOMAIN
<222> LOCATION: (1)..(19)
<223> OTHER INFORMATION:

<400> SEQUENCE: 78

Ser Lys Thr Ser Ala Ser Ile Gly Ser Ala Cys Ala Asp Ala Arg Met
1               5                   10                  15

Tyr Gly Val
```

```
<210> SEQ ID NO 79
<211> LENGTH: 24
<212> TYPE: PRT
<213> ORGANISM: Artificial Sequence
<220> FEATURE:
<223> OTHER INFORMATION: The peptide of SEQ ID NO: 42 in which the
      residues at positions 6, 12 and 18 were replaced by Ala, 2
      residues at the N-terminus and 2 residues as the C-terminus are
      lacking.
<220> FEATURE:
<221> NAME/KEY: DOMAIN
<222> LOCATION: (1)..(24)
<223> OTHER INFORMATION:

<400> SEQUENCE: 79

Ile Tyr Phe Asn Thr Ala Thr Thr Cys Gln Ser Ala Ala Phe Pro Ser
1               5                   10                  15

Lys Ala Ser Ala Ser Ile Gly Ser
            20
```

```
<210> SEQ ID NO 80
<211> LENGTH: 22
<212> TYPE: PRT
<213> ORGANISM: Artificial Sequence
<220> FEATURE:
<223> OTHER INFORMATION: The peptide of SEQ ID NO: 44 in which the
      residues at positions 2, 8 and 13 were replaced by Ala.
<220> FEATURE:
<221> NAME/KEY: DOMAIN
<222> LOCATION: (1)..(22)
<223> OTHER INFORMATION:

<400> SEQUENCE: 80

Ser Ala Ala Phe Pro Ser Lys Ala Ser Ala Ser Ile Ala Ser Leu Cys
1               5                   10                  15

Ala Asp Ala Arg Met Tyr
            20
```

```
<210> SEQ ID NO 81
<211> LENGTH: 20
<212> TYPE: PRT
<213> ORGANISM: Artificial Sequence
<220> FEATURE:
<223> OTHER INFORMATION: The peptide of SEQ ID NO: 42 in which the
      residues at positions 7 and 15 were replaced by Ala, the Cys at
      position 1 was replaced by Ser, having additional 2 residues at
``` the C-terminus and 10 residues at the N-terminus are lacking.
<220> FEATURE:
<221> NAME/KEY: DOMAIN
<222> LOCATION: (1)..(20)
<223> OTHER INFORMATION:

<400> SEQUENCE: 81

Ser Gln Ser Ile Ala Phe Ala Ser Lys Thr Ser Ala Ser Ile Ala Ser
1               5                   10                  15

Leu Cys Ala Asp
            20

<210> SEQ ID NO 82
<211> LENGTH: 22
<212> TYPE: PRT
<213> ORGANISM: Artificial Sequence
<220> FEATURE:
<223> OTHER INFORMATION: The peptide of SEQ ID NO: 45 in which the
      residue at position 10 was replaced by Ala and 9 residues at the
      C-terminus are lacking.
<220> FEATURE:
<221> NAME/KEY: DOMAIN
<222> LOCATION: (1)..(22)
<223> OTHER INFORMATION:

<400> SEQUENCE: 82

Ala Phe Pro Gly Lys Val Cys Gly Ser Ala Leu Leu Ser Ile Cys Lys
1               5                   10                  15

Thr Ala Glu Phe Gln Met
            20

<210> SEQ ID NO 83
<211> LENGTH: 19
<212> TYPE: PRT
<213> ORGANISM: Artificial Sequence
<220> FEATURE:
<223> OTHER INFORMATION: The peptide of SEQ ID NO: 45 in which the
      residue at position 10 was replaced by Ala and 12 residues at
      the N-terminus are lacking

<400> SEQUENCE: 83

Ser Ile Cys Lys Thr Ala Glu Phe Gln Ala Thr Phe His Leu Phe Ile
1               5                   10                  15

Ala Ala Phe

<210> SEQ ID NO 84
<211> LENGTH: 23
<212> TYPE: PRT
<213> ORGANISM: Artificial Sequence
<220> FEATURE:
<223> OTHER INFORMATION: The peptide of SEQ ID NO: 45 in which the
      residues at positions 6 and 11 were replaced by Ala and 8
      residues at the C-terminus are lacking.
<220> FEATURE:
<221> NAME/KEY: DOMAIN
<222> LOCATION: (1)..(23)
<223> OTHER INFORMATION:

<400> SEQUENCE: 84

Ala Phe Pro Gly Lys Ala Cys Gly Ser Asn Ala Leu Ser Ile Cys Lys
1               5                   10                  15

Thr Ala Glu Phe Gln Met Thr
            20

<210> SEQ ID NO 85
<211> LENGTH: 16
<212> TYPE: PRT
<213> ORGANISM: Artificial Sequence

```
<220> FEATURE:
<223> OTHER INFORMATION: The peptide of SEQ ID NO: 46 in which the
      residue at position 10 was replaced by Ala.
<220> FEATURE:
<221> NAME/KEY: DOMAIN
<222> LOCATION: (1)..(16)
<223> OTHER INFORMATION:

<400> SEQUENCE: 85

Thr Tyr Asn Phe Ala Val Leu Lys Leu Ala Gly Arg Gly Thr Lys Phe
1               5                   10                  15

<210> SEQ ID NO 86
<211> LENGTH: 23
<212> TYPE: PRT
<213> ORGANISM: Artificial Sequence
<220> FEATURE:
<223> OTHER INFORMATION: The peptide of SEQ ID NO: 47 in which the
      residue at position 10 was replaced by Ala.
<220> FEATURE:
<221> NAME/KEY: DOMAIN
<222> LOCATION: (1)..(23)
<223> OTHER INFORMATION:

<400> SEQUENCE: 86

Gly His Glu Ala Leu Thr Gly Thr Glu Ala Leu Ile Glu Thr Tyr Phe
1               5                   10                  15

Ser Lys Asn Tyr Gln Asp Tyr
            20

<210> SEQ ID NO 87
<211> LENGTH: 459
<212> TYPE: DNA
<213> ORGANISM: Artificial Sequence
<220> FEATURE:
<223> OTHER INFORMATION: shMOG-AL synthetic gene comprising nucleotides
      coding for the peptides of SEQ ID NOs: 48-53 and restriction
      sites as depicted in Fig 15.

<400> SEQUENCE: 87
gaattcgcta gcgtggggtg gtatcgtcca gccttctctc gtgtggttgc tctgtaccgc      60
aatggcaagg accaagatgg cagcgtgggg tggtatcgtc cgccattctc tgcggtggtt     120
catctgtaca gaaatggcaa gggctcttat cgtggccgta ctgagctgct ggcagatgct     180
attggtgagg gaaaggcgac tctgaggatc gcgaatgtac gtttctctga tgaaggaggt     240
agcggtgagg gaaaggtggc tctccgtatc cgggctgtac gcttctctga tgaaggaggt     300
ttcagatctg gaccacgaca ccgtatcgcg gctctggtcg gggatgaagt ggaattggca     360
tctcgcatct ctccggggaa gaacgctggc tctctgcatc gacgtcttgc agggcaagcc     420
cttgaagagc tgcgaaatcc gttcggatcc tgaaagctt                            459

<210> SEQ ID NO 88
<211> LENGTH: 585
<212> TYPE: DNA
<213> ORGANISM: Artificial Sequence
<220> FEATURE:
<223> OTHER INFORMATION: shMBP-AL synthetic gene comprising nucleotides
      coding for the peptides of SEQ ID NOs: 54-60 and restriction
      sites as depicted in Fig 16.

<400> SEQUENCE: 88
gaattcgcta gcggatccga tgaaaacccg gtagtccact tcttcgcgaa cattgtgacg      60
cctcgcactc caccgccgtc tcagggctct gaaaacccag tagtcgcctt cttcaagaac     120
attgcgacgc cacgcacacc accgccgtcg cagggatcgg ctcacaaggg attcaaggga     180
```

```
gtcgctgccc agggcacgct ttccaaaatt tttaagctgg ggtccggcac gctttctaaa    240
attgctaagc tgggaggacg cgcgagccgc tctggatcgc cgatggctcg tcgcgggtcc    300
tctgctcaca agggattcgc gggagtcgat gcccagggcg cgctttccaa aatttttaag    360
ctgggaggat ctcagcggca cggatctgcg tacctggcca ctgcaagcac gatggacgca    420
gcccggcatg gcttcctttc tagacggcat ggcttccttc cacggcaccg tgccacgggc    480
atccttgact ccatcgggcg ctttctttggt tccggcttcc tgccacgtca cgcagacacg    540
ggcatccttg actccatcgg gcgcttcttt actagttgaa agctt                     585
```

<210> SEQ ID NO 89
<211> LENGTH: 624
<212> TYPE: DNA
<213> ORGANISM: Artificial Sequence
<220> FEATURE:
<223> OTHER INFORMATION: shOSP-AL synthetic gene comprising nucleotides coding for the peptides of SEQ ID NOs: 61-69 and restriction sites as depicted in Fig 17.

<400> SEQUENCE: 89

```
gaattcacta gttccaaggg gctggcggcc gactgcgtcg cggccacggg gctgtacgcc     60
tgcaagccgc tggcggacat ccttatcctg ccgggctacg tgggttctcc gacctgccgc    120
aagctggctg agctgggctc caaggggctg gcggccgact cgtcgcggc cacggggctg     180 tacgcctgcg gtagcacctc ccgcaagctg gctgagcttg gctctgcggg gctgtgggcc    240
gcctgcgtca tggccacggg gttgtaccac tgcggatctg ccattttact gctgcttact    300
gttcttgcct ccatccggat gggccaggag ccgggtagca accgtttcta ctacactgcg    360
ggctctgcct ccccgactca tgcggcgagt gcccacgtag gtagcactgc gggctctagc    420
tccccgactg ctgcgaagag tgcccacgta atgcattgga tcggggtcat cgtgaccacc    480
tccgccaatg actgggtggt gacctccggc tacaccatcc caggcagcgt tttgcttatt    540
ctgcttgctg cctgcgccct tgttgccacc atctggttcg ctgtgtgcgc ccaccgtgag    600
accaccatcc tgcagtgaaa gctt                                            624
```

<210> SEQ ID NO 90
<211> LENGTH: 315
<212> TYPE: DNA
<213> ORGANISM: Artificial Sequence
<220> FEATURE:
<223> OTHER INFORMATION: shMOBP-AL synthetic gene comprising nucleotides coding for the peptides of SEQ ID NOs: 70-73 and restriction sites as depicted in Fig 18.

<400> SEQUENCE: 90

```
gaattcgcta gcctgcagaa aaaccagaaa tactccgcac acttcagcat tcactgctgc     60
ccgccggcca ccttcctcaa ttccaagaag gagataggca gcaagaaaga ggaggactgg    120
gcctgctgtg cctctcaggc gacccgcacc agcgcccgtg ccaagtctcc gcagcggccg    180
aagggttcga agcaacagcc gcgcagcagc ccgcttgcag ggccaggagc cagccgtggg    240
gggtcccgtg ccaagtcccc tcagaggccg gcgcaacagc cagcagcgcc gccagcggtg    300
ctcgagtgaa agctt                                                     315
```

<210> SEQ ID NO 91
<211> LENGTH: 960
<212> TYPE: DNA
<213> ORGANISM: Artificial Sequence
<220> FEATURE:
<223> OTHER INFORMATION: shPLP-AL synthetic gene comprising nucleotides coding for the peptides of SEQ ID NOs: 74-86 and restriction sites as depicted in Fig 19.

<400> SEQUENCE: 91

| | | | | | |
|---|---|---|---|---|---|
| gaattcgcta | gcctcgagga | ctacaagacc | accatctccg | gcgcgggcct | gagcgcaacg | 60 |
| gtaactgggg | gccagaaggg | aagcgactac | aagaccacca | tctccggcaa | gggcgcgagc | 120 |
| gcaacggtaa | ctgggggcca | gaagggaagc | cagaaggggc | gtggttctcg | tggccaagct | 180 |
| caagctcatt | ctgcggagcg | tgtgtgtcat | tgtttgggaa | aagcgcttgg | acatccggac | 240 |
| aagggcagcg | tgtacattta | cttcaacacc | tggaccgcct | cccagtctat | tgccttcccg | 300 |
| agcgcgacct | ctgccagcat | tggcagcctg | tctggcagca | agacctctgc | cagcattggc | 360 |
| agcgcctctg | ctgatgcccg | tatgtatggt | gttgggagca | tttacttcaa | caccgcgacc | 420 |
| acctctcagt | ctgctgcctt | cccgagcaag | gcctctgcca | gcattgggag | ctctgctgcc | 480 |
| ttcccgagca | aggcctctgc | cagcatagcc | agcctgtctg | ctgatgcccg | aatgtatgga | 540 |
| tctcagtcta | ttgccttcgc | cagcaagacc | tctgccagca | ttgccagcct | ttctgctgat | 600 |
| ggtagcgctt | ccctggcaa | ggtttgtggc | tctgcccttc | tgtctatctg | caaaacagct | 660 |
| gagttccaaa | tggggtctat | ctctaaaact | gctgagttcc | aagcgacctt | ccacctgttt | 720 |
| attgctgcat | ttggaagcgc | tttcccggtc | aaggcttgtg | gctccaacgc | tctgtccatc | 780 |
| tgcaaaactg | ctgagttcca | aatgaccgga | tccacttaca | actttgccgt | ccttaaactg | 840 |
| gcgggccgtg | gcaccaagtt | cggctccgga | catgaagccc | tgactggcac | tgaagcgcta | 900 |
| attgagacct | atttctccaa | aaactaccaa | gactattgat | catgagcggc | gcaagctta | 960 |

<210> SEQ ID NO 92
<211> LENGTH: 2841
<212> TYPE: DNA
<213> ORGANISM: Artificial Sequence
<220> FEATURE:
<223> OTHER INFORMATION: Y-MSP-AL -synthetic gene comprising the nucleotide sequences of SEQ ID NOs: 87-91 and restriction sites as depicted in Fig 20.

<400> SEQUENCE: 92

| | | | | | |
|---|---|---|---|---|---|
| gaattcgcta | gcgtggggtg | gtatcgtcca | gccttctctc | gtgtggttgc | tctgtaccgc | 60 |
| aatggcaagg | accaagatgg | cagcgtgggg | tggtatcgtc | cgccattctc | tgcggtggtt | 120 |
| catctgtaca | gaaatggcaa | gggctcttat | cgtggccgta | ctgagctgct | ggcagatgct | 180 |
| attggtgagg | gaaaggcgac | tctgaggatc | gcgaatgtac | gtttctctga | tgaaggaggt | 240 |
| agcggtgagg | gaaaggtggc | tctccgtatc | cgggctgtac | gcttctctga | tgaaggaggt | 300 |
| ttcagatctg | gaccacgaca | ccgtatcgcg | gctctggtcg | gggatgaagt | ggaattggca | 360 |
| tctcgcatct | ctccggggaa | gaacgctggc | tctctgcatc | gacgtcttgc | agggcaagcc | 420 |
| cttgaagagc | tgcgaaatcc | gttcggatcc | gatgaaaacc | cggtagtcca | cttcttcgcg | 480 |
| aacattgtga | cgcctcgcac | tccaccgccg | tctcagggct | ctgaaaaccc | agtagtcgcc | 540 |
| ttcttcaaga | acattgcgac | gccacgcaca | ccaccgccgt | cgcagggatc | ggctcacaag | 600 |
| ggattcaagg | gagtcgctgc | ccagggcacg | ctttccaaaa | tttttaagct | ggggtccggc | 660 |
| acgctttcta | aaattgctaa | gctgggagga | cgcgcgagcc | gctctggatc | gccgatggct | 720 |
| cgtcgcgggt | cctctgctca | caagggattc | gcggagtcg | atgcccaggg | cgcgcttttcc | 780 |
| aaaatttttta | agctgggagg | atctcagcgg | cacggatctg | cgtacctggc | cactgcaagc | 840 |
| acgatggacg | cagcccggca | tggcttcctt | tctagacggc | atggcttcct | tccacggcac | 900 |
| cgtgccacgg | gcatccttga | ctccatcggg | cgcttctttg | gttccggctt | cctgccacgt | 960 |

```
cacgcagaca cgggcatcct tgactccatc gggcgcttct ttactagttc caaggggctg    1020
gcggccgact gcgtcgcggc cacggggctg tacgcctgca agccgctggc ggacatcctt    1080
atcctgccgg gctacgtggg ttctccgacc tgccgcaagc tggctgagct gggctccaag    1140
gggctggcgc ccgactgcgt cgcggccacg ggctgtacg cctgcggtag cacctcccgc     1200
aagctggctg agcttggctc tgcggggctg tgggccgcct gcgtcatggc cacggggttg    1260
taccactgcg gatctgccat tttactgctg cttactgttc ttgcctccat ccggatgggc    1320
caggagccgg gtagcaaccg tttctactac actgcgggct ctgcctcccc gactcatgcg    1380
gcgagtgccc acgtaggtag cactgcgggc tctagctccc cgactgctgc gaagagtgcc    1440
cacgtaatgc attggatcgg ggtcatcgtg accacctccg ccaatgactg ggtggtgacc    1500
tccggctaca ccatcccagg cagcgttttg cttattctgc ttgctgcctg cgcccttgtt    1560
gccaccatct ggttcgctgt gtgcgcccac cgtgagacca ccatcctgca gaaaaaccag    1620
aaatactccg cacacttcag cattcactgc tgcccgccgg ccaccttcct caattccaag    1680
aaggagatag gcagcaagaa agaggaggac tgggcctgct gtgcctctca ggcgacccgc    1740
accagcgccc gtgccaagtc tccgcagcgg ccgaagggtt cgaagcaaca gccgcgcagc    1800
agcccgcttg cagggccagg agccagccgt gggggtccc gtgccaagtc ccctcagagg     1860
ccggcgcaac agccagcagc gccgccagcg gtgctcgagg actacaagac caccatctcc    1920
ggcgcgggcc tgagcgcaac ggtaactggg ggccagaagg gaagcgacta caagaccacc    1980
atctccggca agggcgcgag cgcaacggta actgggggcc agaagggaag ccagaagggg    2040
cgtggttctc gtggccaagc tcaagctcat tctgcggagc gtgtgtgtca ttgtttggga    2100
aaagcgcttg gacatccgga caagggcagc gtgtacattt acttcaacac ctggaccgcc    2160
tcccagtcta ttgccttccc gagcgcgacc tctgccagca ttggcagcct gtctggcagc    2220
aagacctctg ccagcattgg cagcgcctct gctgatgccc gtatgtatgg tgttgggagc    2280
atttacttca acaccgcgac cacctctcag tctgctgcct tcccgagcaa ggcctctgcc    2340
agcattggga gctctgctgc cttcccgagc aaggcctctg ccagcatagc cagcctgtct    2400
gctgatgccc gaatgtatgg atctcagtct attgccttcg ccagcaagac ctctgccagc    2460
attgccagcc tttctgctga tggtagcgct ttccctggca aggtttgtgg ctctgccctt    2520
ctgtctatct gcaaaacagc tgagttccaa atggggtcta tctctaaaac tgctgagttc    2580
caagcgacct ccacctgtt tattgctgca tttggaagcg ctttcccggt caaggcttgt     2640
ggctccaacg ctctgtccat ctgcaaaact gctgagttcc aaatgaccgg atccacttac    2700
aactttgccg tccttaaact ggcgggccgt ggcaccaagt tcggctccgg acatgaagcc    2760
ctgactggca ctgaagcgct aattgagacc tatttctcca aaaactacca agactattga    2820
tcatgagcgg ccgcaagctt a                                             2841
```

<210> SEQ ID NO 93
<211> LENGTH: 2280
<212> TYPE: DNA
<213> ORGANISM: Artificial Sequence
<220> FEATURE:
<223> OTHER INFORMATION: delta Y-MSP-AL -synthetic gene comprising
    nucleotides coding for SEQ ID NOs: 48-51, 54-59, 62-67, 70-73,
    74-84 and restriction sites as depicted in Fig 21.

<400> SEQUENCE: 93

```
gaattcgcta gcgtggggtg gtatcgtcca gccttctctc gtgtggttgc tctgtaccgc      60
aatggcaagg accaagatgg cagcgtgggg tggtatcgtc cgccattctc tgcggtggtt     120
```

| | |
|---|---|
| catctgtaca gaaatggcaa gggctcttat cgtggccgta ctgagctgct ggcagatgct | 180 |
| attggtgagg gaaaggcgac tctgaggatc gcgaatgtac gtttctctga tgaaggaggt | 240 |
| agcggtgagg gaaaggtggc tctccgtatc cgggctgtac gcttctctga tgaaggaggt | 300 |
| ttcagatccg atgaaaaccc ggtagtccac ttcttcgcga acattgtgac gcctcgcact | 360 |
| ccaccgccgt ctcagggctc tgaaaaccca gtagtcgcct tcttcaagaa cattgcgacg | 420 |
| ccacgcacac caccgccgtc gcagggatcg gctcacaagg gattcaaggg agtcgctgcc | 480 |
| cagggcacgc tttccaaaat ttttaagctg gggtccggca cgctttctaa aattgctaag | 540 |
| ctgggaggac gcgcgagccg ctctggatcc ccgatggctc gtcgcgggtc tctgctcac | 600 |
| aagggattcg cgggagtcga tgcccagggc gcgcttttcca aaattttttaa gctgggagga | 660 |
| tctcagcggc acggatctgc gtacctggcc actgcaagca cgatggacgc agcccggcat | 720 |
| ggcttccttt ctagttccaa ggggctggcg gccgactgcg tcgcggccac ggggctgtac | 780 |
| gcctgcaagc cgctggcgga catccttatc ctgccgggct acgtgggttc tccgacctgc | 840 |
| cgcaagctgg ctgagctggg ctccaagggg ctggcggccg actgcgtcgc ggccacgggg | 900 |
| ctgtacgcct gcggtagcac ctcccgcaag ctggctgagc ttggctctgc ggggctgtgg | 960 |
| gccgcctgcg tcatggccac ggggttgtac cactgcggat ctgccatttt actgctgctt | 1020 |
| actgttcttg cctccatccg gatgggccag gagccgggta gcaaccgttt ctactacact | 1080 |
| gcgggctctg cctccccgac tcatgcggcg agtgcccacg taggtagcac tgcgggctct | 1140 |
| agctccccga ctgctgcgaa gagtgccacc gtaatgcaga aaaccagaa atactccgca | 1200 |
| cacttcagca ttcactgctg cccgccggcc accttcctca attccaagaa ggagataggc | 1260 |
| agcaagaaag aggaggactg ggcctgctgt gcctctcagg cgacccgcac cagcgcccgt | 1320 |
| gccaagtctc cgcagcggcc gaagggttcg aagcaacagc cgcgcagcag cccgcttgca | 1380 |
| gggccaggag ccagccgtgg ggggtcccgt gccaagtccc ctcagaggcc ggcgcaacag | 1440 |
| ccagcagcgc cgccagcggt gctcgaggac tacaagacca ccatctccgg cgcgggcctg | 1500 |
| agcgcaacgg taactggggg ccagaaggga agcgactaca agaccaccat ctccggcaag | 1560 |
| ggcgcgagcg caacggtaac tgggggccag aagggaagcc agaaggggcg tggttctcgt | 1620 |
| ggccaagctc aagctcattc tgcggagcgt gtgtgtcatt gtttgggaaa agcgcttgga | 1680 |
| catccggaca agggcagcgt gtacatttac ttcaacacct ggaccgcctc ccagtctatt | 1740 |
| gccttcccga gcgcgaccct tgccagcatt ggcagcctgt ctggcagcaa gacctctgcc | 1800 |
| agcattggca gcgcctctgc tgatgcccgt atgtatggtg ttgggagcat ttacttcaac | 1860 |
| accgcgacca cctctcagtc tgctgccttc ccgagcaagg cctctgccag cattgggagc | 1920 |
| tctgctgcct tcccgagcaa ggcctctgcc agcatagcca gctgtctgc tgatgcccga | 1980 |
| atgtatggat ctcagtctat tgccttcgcc agcaagacct ctgccagcat tgccagcctt | 2040 |
| tctgctgatg gtagcgcttt ccctggcaag gtttgtggct ctgcccttct gtctatctgc | 2100 |
| aaaacagctg agttccaaat ggggtctatc tctaaaactg ctgagttcca agcgaccttc | 2160 |
| cacctgttta ttgctgcatt tggaagcgct ttccgggtca aggcttgtgg ctccaacgct | 2220 |
| ctgtccatct gcaaaactgc tgagttccaa atgaccggat catgagcggc cgcaagctta | 2280 |

<210> SEQ ID NO 94
<211> LENGTH: 69
<212> TYPE: DNA
<213> ORGANISM: Artificial Sequence
<220> FEATURE:
<223> OTHER INFORMATION: MOG.p1 - primer for construction of the shMOG
      gene of SEQ ID NO: 102.

```
<400> SEQUENCE: 94
gaattcgcta gcgtggggtg gtatcgcccg ccattctctc gtgtggttca tctctaccgc      60
aatggcaag                                                             69

<210> SEQ ID NO 95
<211> LENGTH: 69
<212> TYPE: DNA
<213> ORGANISM: Artificial Sequence
<220> FEATURE:
<223> OTHER INFORMATION: MOG.p2 (rev) - primer for construction of the
      shMOG gene of SEQ ID NO:102.

<400> SEQUENCE: 95
aatagcatct ttcagcagct ctgtgcgacc gcgatatgag ccatcttggt ccttgccatt      60
gcggtagag                                                             69

<210> SEQ ID NO 96
<211> LENGTH: 69
<212> TYPE: DNA
<213> ORGANISM: Artificial Sequence
<220> FEATURE:
<223> OTHER INFORMATION: MOG.p3 - primer for construction of the shMOG
      gene of SEQ ID NO: 102.

<400> SEQUENCE: 96
ctgctgaaag atgctattgg tgagggcaag gtgactctcc gtatccgcaa tgtacgtttc      60
tcagatgaa                                                             69

<210> SEQ ID NO 97
<211> LENGTH: 69
<212> TYPE: DNA
<213> ORGANISM: Artificial Sequence
<220> FEATURE:
<223> OTHER INFORMATION: MOG.p4 (rev) - primer for construction of the
      shMOG gene of SEQ ID NO: 102.

<400> SEQUENCE: 97
ttcatccccg accagagccc ggatagggtg gcgtgggcca gatctaccac cttcatctga     60
gaaacgtac                                                             69

<210> SEQ ID NO 98
<211> LENGTH: 69
<212> TYPE: DNA
<213> ORGANISM: Artificial Sequence
<220> FEATURE:
<223> OTHER INFORMATION: MOG.p5 - primer for construction of the shMOG
      gene of SEQ ID NO: 102.

<400> SEQUENCE: 98
gctctggtcg gggatgaagt ggaattgcca tgtcgcatct ctcctgggaa gaacgctggc      60
tcactgcat                                                             69

<210> SEQ ID NO 99
<211> LENGTH: 69
<212> TYPE: DNA
<213> ORGANISM: Artificial Sequence
<220> FEATURE:
<223> OTHER INFORMATION: MOG.p6 (rev) - primer for construction of the
      shMOG gene of SEQ ID NO: 102.

<400> SEQUENCE: 99
ggatccgaac ggattacgca gctcttcaag gaattgccct gccaggcgac gatgcagtga      60
```

<210> SEQ ID NO 100
<211> LENGTH: 30
<212> TYPE: DNA
<213> ORGANISM: Artificial Sequence
<220> FEATURE:
<223> OTHER INFORMATION: MOG.p1a - primer for amplification of the shMOG gene of SEQ ID NO: 102.

<400> SEQUENCE: 100
gaattcgcta gcgtggggtg gtatcgcccg                                    30

<210> SEQ ID NO 101
<211> LENGTH: 36
<212> TYPE: DNA
<213> ORGANISM: Artificial Sequence
<220> FEATURE:
<223> OTHER INFORMATION: MOG.p6a (rev) - primer for amplification of the shMOG gene of SEQ ID NO:102.

<400> SEQUENCE: 101
aagctttcag gatccgaacg gattacgcag ctcttc                             36

<210> SEQ ID NO 102
<211> LENGTH: 333
<212> TYPE: DNA
<213> ORGANISM: Artificial Sequence
<220> FEATURE:
<223> OTHER INFORMATION: shMOG synthetic gene construct comprising nucleotides coding for the peptides of SEQ ID NOs: 22-25 and restriction sites as depicted in Fig 1.

<400> SEQUENCE: 102
gaattcgcta gcgtggggtg gtatcgcccg ccattctctc gtgtggttca tctctaccgc    60
aatggcaagg accaagatgg ctcatatcgc ggtcgcacag agctgctgaa agatgctatt   120
ggtgagggca aggtgactct ccgtatccgc aatgtacgtt tctcagatga aggtggtaga   180
tctggcccac gccaccctat ccgggctctg gtcggggatg aagtggaatt gccatgtcgc   240
atctctcctg gaagaacgc tggctcactg catcgtcgcc tggcagggca attccttgaa   300
gagctgcgta atccgttcgg atcctgaaag ctt                                333

<210> SEQ ID NO 103
<211> LENGTH: 108
<212> TYPE: PRT
<213> ORGANISM: Artificial Sequence
<220> FEATURE:
<223> OTHER INFORMATION: shMOG - polypeptide containing the peptides of SEQ ID NOs: 22-25
<220> FEATURE:
<221> NAME/KEY: DOMAIN
<222> LOCATION: (1)..(108)
<223> OTHER INFORMATION:

<400> SEQUENCE: 103

Glu Phe Ala Ser Val Gly Trp Tyr Arg Pro Pro Phe Ser Arg Val Val
1               5                   10                  15

His Leu Tyr Arg Asn Gly Lys Asp Gln Asp Gly Ser Tyr Arg Gly Arg
            20                  25                  30

Thr Glu Leu Leu Lys Asp Ala Ile Gly Glu Gly Lys Val Thr Leu Arg
        35                  40                  45

Ile Arg Asn Val Arg Phe Ser Asp Glu Gly Gly Arg Ser Gly Pro Arg
    50                  55                  60

His Pro Ile Arg Ala Leu Val Gly Asp Glu Val Glu Leu Pro Cys Arg

```
                65                  70                  75                  80
Ile Ser Pro Gly Lys Asn Ala Gly Ser Leu His Arg Arg Leu Ala Gly
                    85                  90                  95
Gln Phe Leu Glu Glu Leu Arg Asn Pro Phe Gly Ser
                100                 105

<210> SEQ ID NO 104
<211> LENGTH: 69
<212> TYPE: DNA
<213> ORGANISM: Artificial Sequence
<220> FEATURE:
<223> OTHER INFORMATION: MBP.p1 - primer for construction of the shMBP
      gene of SEQ ID NO: 114.

<400> SEQUENCE: 104
gaattcgcta gcggatccga tgaaaacccg gtagtccact tcttcaagaa cattgtgacg        60
cctcgcaca                                                                69

<210> SEQ ID NO 105
<211> LENGTH: 69
<212> TYPE: DNA
<213> ORGANISM: Artificial Sequence
<220> FEATURE:
<223> OTHER INFORMATION: MBP.p2 (rev) - primer for construction of the
      shMBP gene of SEQ ID NO: 114.

<400> SEQUENCE: 105
ggcatcgacg cccttgaaac ccttgtgagc cgagccctgc gacggcggtg gtgtgcgagg        60
cgtcacaat                                                                69

<210> SEQ ID NO 106
<211> LENGTH: 69
<212> TYPE: DNA
<213> ORGANISM: Artificial Sequence
<220> FEATURE:
<223> OTHER INFORMATION: MBP.p3 - primer for construction of the shMBP
      gene of SEQ ID NO: 114.

<400> SEQUENCE: 106
ttcaagggcg tcgatgccca gggcacgctt tccaaaattt ttaagctgtc tggcacgctt        60
tccaaaatt                                                                69

<210> SEQ ID NO 107
<211> LENGTH: 63
<212> TYPE: DNA
<213> ORGANISM: Artificial Sequence
<220> FEATURE:
<223> OTHER INFORMATION: MBP.p4 (rev)- primer for construction of the
      shMBP gene of SEQ ID NO: 114.

<400> SEQUENCE: 107
agccatcggt gagccagagc gactatcgcg gccacccagc ttaaaaattt tggaaagcgt        60
gcc                                                                      63

<210> SEQ ID NO 108
<211> LENGTH: 63
<212> TYPE: DNA
<213> ORGANISM: Artificial Sequence
<220> FEATURE:
<223> OTHER INFORMATION: MBP.p5 - primer for construction of the shMBP
      gene of SEQ ID NO: 114.

<400> SEQUENCE: 108
tctggctcac cgatggctcg tcgcggttcc cagcgccacg gttccaagta cctggccaca        60
```

<210> SEQ ID NO 109
<211> LENGTH: 63
<212> TYPE: DNA
<213> ORGANISM: Artificial Sequence
<220> FEATURE:
<223> OTHER INFORMATION: MBP.p6 (rev) - primer for construction of the shMBP gene of SEQ ID NO:114.

<400> SEQUENCE: 109
atgacgtcta gagaggaagc catgacgggc atggtccata gtgcttgctg tggccaggta    60
ctt                                                                 63

<210> SEQ ID NO 110
<211> LENGTH: 63
<212> TYPE: DNA
<213> ORGANISM: Artificial Sequence
<220> FEATURE:
<223> OTHER INFORMATION: MBP.p7 - primer for construction of the shMBP gene of SEQ ID NO: 114.

<400> SEQUENCE: 110
ttcctctcta gacgtcatgg cttcctccca cgtcaccgcg acacgggcat ccttgactcc    60
atc                                                                 63

<210> SEQ ID NO 111
<211> LENGTH: 51
<212> TYPE: DNA
<213> ORGANISM: Artificial Sequence
<220> FEATURE:
<223> OTHER INFORMATION: MBP.p8 (rev) - primer for construction of the shMBP gene of SEQ ID NO: 114.

<400> SEQUENCE: 111
aagctttcaa ctagtaaaga agcgcccgat ggagtcaagg atgcccgtgt c             51

<210> SEQ ID NO 112
<211> LENGTH: 36
<212> TYPE: DNA
<213> ORGANISM: Artificial Sequence
<220> FEATURE:
<223> OTHER INFORMATION: MBP.p1a- primer for amplification of the shMBP gene of SEQ ID NO: 114.

<400> SEQUENCE: 112
gaattcgcta gcggatccga tgaaaacccg gtagtc                              36

<210> SEQ ID NO 113
<211> LENGTH: 33
<212> TYPE: DNA
<213> ORGANISM: Artificial Sequence
<220> FEATURE:
<223> OTHER INFORMATION: MBP.p8a (rev) - primer for amplification of the shMBP gene of SEQ ID NO: 114.

<400> SEQUENCE: 113
aagctttcaa ctagtaaaga agcgcccgat gga                                 33

Figure 2:
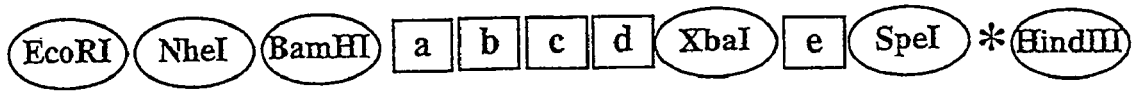
FIG. 2 depicts a scheme of the herein designated shMBP gene in which the sequences of epitope clusters a-e are SEQ ID NO:26-30, respectively.

<210> SEQ ID NO 114
<211> LENGTH: 378
<212> TYPE: DNA
<213> ORGANISM: Artificial Sequence
<220> FEATURE:
<223> OTHER INFORMATION: shMBP synthetic gene construct comprising nucleotides coding for the amino acids of SEQ ID NOs: 26-30 and -continued restriction sites as depicted in Fig 2.

<400> SEQUENCE: 114

```
gaattcgcta gcggatccga tgaaaacccg gtagtccact tcttcaagaa cattgtgacg    60
cctcgcacac caccgccgtc gcagggctcg gctcacaagg gtttcaaggg cgtcgatgcc   120
cagggcacgc tttccaaaat ttttaagctg tctggcacgc tttccaaaat ttttaagctg   180
ggtggccgcg atagtcgctc tggctcaccg atggctcgtc gcggttccca gcgccacggt   240
tccaagtacc tggccacagc aagcactatg gaccatgccc gtcatggctt cctctctaga   300
cgtcatggct cctcccacg tcaccgcgac acgggcatcc ttgactccat cgggcgcttc   360
tttactagtt gaaagctt                                                 378
```

<210> SEQ ID NO 115
<211> LENGTH: 123
<212> TYPE: PRT
<213> ORGANISM: Artificial Sequence
<220> FEATURE:
<223> OTHER INFORMATION: shMBP - polypeptide containing the peptides
      of SEQ ID NOs: 26-30
<220> FEATURE:
<221> NAME/KEY: DOMAIN
<222> LOCATION: (1)..(123)
<223> OTHER INFORMATION:

<400> SEQUENCE: 115

```
Glu Phe Ala Ser Gly Ser Asp Glu Asn Pro Val Val His Phe Phe Lys
1               5                   10                  15

Asn Ile Val Thr Pro Arg Thr Pro Pro Pro Ser Gln Gly Ser Ala His
            20                  25                  30

Lys Gly Phe Lys Gly Val Asp Ala Gln Gly Thr Leu Ser Lys Ile Phe
        35                  40                  45

Lys Leu Ser Gly Thr Leu Ser Lys Ile Phe Lys Leu Gly Gly Arg Asp
    50                  55                  60

Ser Arg Ser Gly Ser Pro Met Ala Arg Arg Gly Ser Gln Arg His Gly
65                  70                  75                  80

Ser Lys Tyr Leu Ala Thr Ala Ser Thr Met Asp His Ala Arg His Gly
                85                  90                  95

Phe Leu Ser Arg Arg His Gly Phe Leu Pro Arg His Arg Asp Thr Gly
            100                 105                 110

Ile Leu Asp Ser Ile Gly Arg Phe Phe Thr Ser
        115                 120
```

<210> SEQ ID NO 116
<211> LENGTH: 66
<212> TYPE: DNA
<213> ORGANISM: Artificial Sequence
<220> FEATURE:
<223> OTHER INFORMATION: OSP.p1 - primer for construction of the shOSP
      gene of SEQ ID NO:128.

<400> SEQUENCE: 116

```
gaattcacta gttccaaggg gctgtgggcc gactgcgtca tggccacggg gctgtaccac    60
tgcaag                                                              66
```

<210> SEQ ID NO 117
<211> LENGTH: 66
<212> TYPE: DNA
<213> ORGANISM: Artificial Sequence
<220> FEATURE:
<223> OTHER INFORMATION: OSP.p2 (rev)- primer for construction of the
      shOSP gene of SEQ ID NO:128.

-continued

<400> SEQUENCE: 117
ggtcggagag cccacgtagc ccggcaggat gaggatgtcc accagcggct tgcagtggta     60
cagccc                                                                66

<210> SEQ ID NO 118
<211> LENGTH: 66
<212> TYPE: DNA
<213> ORGANISM: Artificial Sequence
<220> FEATURE:
<223> OTHER INFORMATION: OSP.p3 - primer for construction of the shOSP
      gene of SEQ ID NO: 128.

<400> SEQUENCE: 118
tacgtgggct ctccgacctg ccgcaagctg gatgagctgg ctccaaggg gctgtgggcc      60 gactgc                                                                66

<210> SEQ ID NO 119
<211> LENGTH: 66
<212> TYPE: DNA
<213> ORGANISM: Artificial Sequence
<220> FEATURE:
<223> OTHER INFORMATION: OSP.p4 (rev) - primer for construction of the
      shOSP gene of SEQ ID NO:128.

<400> SEQUENCE: 119
cagcagtaaa atggctgaac cgcagtggta cagccccgtg gccatgacgc agtcggccca     60
cagccc                                                                66

<210> SEQ ID NO 120
<211> LENGTH: 66
<212> TYPE: DNA
<213> ORGANISM: Artificial Sequence
<220> FEATURE:
<223> OTHER INFORMATION: OSP.p5 - primer for construction of the shOSP
      gene of SEQ ID NO: 128.

<400> SEQUENCE: 120
tcagccattt tactgctgct gactgttctt ccgtgcatcc gtatgggcca ggagccaggt     60
tccaac                                                                66

<210> SEQ ID NO 121
<211> LENGTH: 66
<212> TYPE: DNA
<213> ORGANISM: Artificial Sequence
<220> FEATURE:
<223> OTHER INFORMATION: OSP.p6 (rev) - primer for construction of the
      shOSP gene of SEQ ID NO:128.

<400> SEQUENCE: 121
actcttcgca tgagtcgggg agctagagcc cgcagtgtag tagaaacggt tggaacctgg     60
ctcctg                                                                66

<210> SEQ ID NO 122
<211> LENGTH: 66
<212> TYPE: DNA
<213> ORGANISM: Artificial Sequence
<220> FEATURE:
<223> OTHER INFORMATION: OSP.p7 - primer for construction of the shOSP
      gene of SEQ ID NO:128.

<400> SEQUENCE: 122
ccgactcatg cgaagagtgc ccacgtaatg cattggatcg gggtcatcgt gaccacctcc     60

```
accaat                                                              66

<210> SEQ ID NO 123
<211> LENGTH: 66
<212> TYPE: DNA
<213> ORGANISM: Artificial Sequence
<220> FEATURE:
<223> OTHER INFORMATION: OSP.p8 (rev) - primer for construction of the
      shOSP gene of SEQ ID NO:128.

<400> SEQUENCE: 123
gagcaaaacg gaccctggga tggtgtagcc gcaggtcacc acccagtcat tggtggaggt    60
ggtcac                                                              66

<210> SEQ ID NO 124
<211> LENGTH: 66
<212> TYPE: DNA
<213> ORGANISM: Artificial Sequence
<220> FEATURE:
<223> OTHER INFORMATION: OSP.p9 - primer for construction of the shOSP
      gene of SEQ ID NO:128.

<400> SEQUENCE: 124
ccagggtccg ttttgctcat tctgctggct ctctgcgccc ttgttgccac catctggttc    60
cctgtg                                                              66

<210> SEQ ID NO 125
<211> LENGTH: 63
<212> TYPE: DNA
<213> ORGANISM: Artificial Sequence
<220> FEATURE:
<223> OTHER INFORMATION: OSP.p10 (rev) - primer for construction of the
      shOSP gene of SEQ ID NO:128.

<400> SEQUENCE: 125
aagctttcac tgcaggatgg tggtctcacg gtgggcgcac acaggaacc agatggtggc     60 aac                                                                 63

<210> SEQ ID NO 126
<211> LENGTH: 30
<212> TYPE: DNA
<213> ORGANISM: Artificial Sequence
<220> FEATURE:
<223> OTHER INFORMATION: OSP.p1a - primer for amplification of the shOSP
      gene of SEQ ID NO:128.

<400> SEQUENCE: 126
gaattcacta gttccaaggg gctgtgggcc                                    30

<210> SEQ ID NO 127
<211> LENGTH: 36
<212> TYPE: DNA
<213> ORGANISM: Artificial Sequence
<220> FEATURE:
<223> OTHER INFORMATION: OSP.p10a (rev) - primer for amplification of
      the shOSP gene of SEQ ID NO:128.

<400> SEQUENCE: 127
aagctttcac tgcaggatgg tggtctcacg gtgggc                             36

<210> SEQ ID NO 128
<211> LENGTH: 489
<212> TYPE: DNA
<213> ORGANISM: Artificial Sequence
<220> FEATURE:
<223> OTHER INFORMATION: shOSP synthetic gene construct comprising
``` nucleotides coding for the amino acids of SEQ ID NOs: 10, 31-35
and restriction sites as depicted in Fig 3.

<400> SEQUENCE: 128

```
gaattcacta gttccaaggg gctgtgggcc gactgcgtca tggccacggg gctgtaccac    60
tgcaagccgc tggtggacat cctcatcctg ccgggctacg tgggctctcc gacctgccgc   120
aagctggatg agctgggctc caaggggctg tgggccgact gcgtcatggc cacggggctg   180
taccactgcg gttcagccat tttactgctg ctgactgttc ttccgtgcat ccgtatgggc   240
caggagccag gttccaaccg tttctactac actgcgggct ctagctcccc gactcatgcg   300
aagagtgccc acgtaatgca ttggatcggg gtcatcgtga ccacctccac caatgactgg   360
gtggtgacct gcggctacac catcccaggg tccgttttgc tcattctgct ggctctctgc   420
gcccttgttg ccaccatctg gttccctgtg tgcgcccacc gtgagaccac catcctgcag   480
tgaaagctt                                                           489
```

<210> SEQ ID NO 129
<211> LENGTH: 160
<212> TYPE: PRT
<213> ORGANISM: Artificial Sequence
<220> FEATURE:
<223> OTHER INFORMATION: shOSP - polypeptide containing the peptides of
      SEQ ID NOs: 10, 31-35.
<220> FEATURE:
<221> NAME/KEY: DOMAIN
<222> LOCATION: (1)..(160)
<223> OTHER INFORMATION:

<400> SEQUENCE: 129

```
Glu Phe Thr Ser Ser Lys Gly Leu Trp Ala Asp Cys Val Met Ala Thr
1               5                   10                  15

Gly Leu Tyr His Cys Lys Pro Leu Val Asp Ile Leu Ile Leu Pro Gly
            20                  25                  30

Tyr Val Gly Ser Pro Thr Cys Arg Lys Leu Asp Glu Leu Gly Ser Lys
        35                  40                  45

Gly Leu Trp Ala Asp Cys Val Met Ala Thr Gly Leu Tyr His Cys Gly
    50                  55                  60

Ser Ala Ile Leu Leu Leu Leu Thr Val Leu Pro Cys Ile Arg Met Gly
65                  70                  75                  80

Gln Glu Pro Gly Ser Asn Arg Phe Tyr Tyr Thr Ala Gly Ser Ser Ser
                85                  90                  95

Pro Thr His Ala Lys Ser Ala His Val Met His Trp Ile Gly Val Ile
            100                 105                 110

Val Thr Thr Ser Thr Asn Asp Trp Val Val Thr Cys Gly Tyr Thr Ile
        115                 120                 125

Pro Gly Ser Val Leu Leu Ile Leu Leu Ala Leu Cys Ala Leu Val Ala
    130                 135                 140

Thr Ile Trp Phe Pro Val Cys Ala His Arg Glu Thr Thr Ile Leu Gln
145                 150                 155                 160
```

<210> SEQ ID NO 130
<211> LENGTH: 69
<212> TYPE: DNA
<213> ORGANISM: Artificial Sequence
<220> FEATURE:
<223> OTHER INFORMATION: MOBP.p1 - primer for construction of the shMOBP
      gene of SEQ ID NO: 138.

<400> SEQUENCE: 130

```
gaattcgcta gcctgcagaa aaaccagaag tacagcgaac acttcagcat tcactgctgc    60
```

```
ccgccgttc                                                                  69

<210> SEQ ID NO 131
<211> LENGTH: 69
<212> TYPE: DNA
<213> ORGANISM: Artificial Sequence
<220> FEATURE:
<223> OTHER INFORMATION: MOBP.p2 (rev) - primer for construction of the
      shMOBP gene of SEQ ID NO:138.

<400> SEQUENCE: 131
gtcctcctct ttcttctgag agccaatctc cttcttggaa ttgaggaagg tgaacggcgg         60
gcagcagtg                                                                  69

<210> SEQ ID NO 132
<211> LENGTH: 69
<212> TYPE: DNA
<213> ORGANISM: Artificial Sequence
<220> FEATURE:
<223> OTHER INFORMATION: MOBP.p3 - primer for construction of the shMOBP
      gene of SEQ ID NO: 138.

<400> SEQUENCE: 132
cagaagaaag aggaggactg gatctgctgc gcctgccaga agacccgcac cagccgccgt         60
gccaagtct                                                                  69

<210> SEQ ID NO 133
<211> LENGTH: 72
<212> TYPE: DNA
<213> ORGANISM: Artificial Sequence
<220> FEATURE:
<223> OTHER INFORMATION: MOBP.p4 (rev) - primer for construction of the
      shMOBP gene of SEQ ID NO: 138.

<400> SEQUENCE: 133
cccacggagt gggctgctgc gcggctgttg cttagagccc ttcgggcgct gaggagactt         60
ggcacggcgg ct                                                              72

<210> SEQ ID NO 134
<211> LENGTH: 69
<212> TYPE: DNA
<213> ORGANISM: Artificial Sequence
<220> FEATURE:
<223> OTHER INFORMATION: MOBP.p5 - primer for construction of the shMOBP
      gene of SEQ ID NO: 138.

<400> SEQUENCE: 134
agcagcccac tccgtgggcc aggcgctagt cgtggtgggt cctcccgtgc caagccgcct         60
cagcgccca                                                                  69

<210> SEQ ID NO 135
<211> LENGTH: 63
<212> TYPE: DNA
<213> ORGANISM: Artificial Sequence
<220> FEATURE:
<223> OTHER INFORMATION: MOBP.p6 (rev) - primer for construction of the
      shMOBP gene of SEQ ID NO: 138.

<400> SEQUENCE: 135
aagctttcac tcgagcaccg ccggcggcgc agcaggctgt tgctttgggc gctgaggcgg         60
ctt                                                                        63

<210> SEQ ID NO 136
```

```
<211> LENGTH: 36
<212> TYPE: DNA
<213> ORGANISM: Artificial Sequence
<220> FEATURE:
<223> OTHER INFORMATION: MOBP.p1a - primer for amplification of the
      shMOBP gene of SEQ ID NO: 138.

<400> SEQUENCE: 136
gaattcgcta gcctgcagaa aaccagaag tacagc                              36

<210> SEQ ID NO 137
<211> LENGTH: 33
<212> TYPE: DNA
<213> ORGANISM: Artificial Sequence
<220> FEATURE:
<223> OTHER INFORMATION: MOBP.p6a (rev) - primer for amplification of
      the shMOBP gene of SEQ ID NO: 138.

<400> SEQUENCE: 137
aagctttcac tcgagcaccg ccggcggcgc agc                                33

<210> SEQ ID NO 138
<211> LENGTH: 321
<212> TYPE: DNA
<213> ORGANISM: Artificial Sequence
<220> FEATURE:
<223> OTHER INFORMATION: shMOBP synthetic gene construct comprising
      nucleotides coding for the amino acids of SEQ ID NOs: 36-39 and
      restriction sites as depicted in Fig 4.

<400> SEQUENCE: 138
gaattcgcta gcctgcagaa aaaccagaag tacagcgaac acttcagcat tcactgctgc    60
ccgccgttca ccttcctcaa ttccaagaag gagattggct ctcagaagaa agaggaggac   120
tggatctgct gcgcctgcca agacccgc accagccgcc gtgccaagtc tcctcagcgc    180
ccgaagggct ctaagcaaca gccgcgcagc agcccactcc gtgggccagg cgctagtcgt   240
ggtgggtcct cccgtgccaa gccgcctcag cgcccaaagc aacagcctgc tgcgccgccg   300
gcggtgctcg agtgaaagct t                                            321

<210> SEQ ID NO 139
<211> LENGTH: 104
<212> TYPE: PRT
<213> ORGANISM: Artificial Sequence
<220> FEATURE:
<223> OTHER INFORMATION: shMOBP - polypeptide containing the peptides of
      SEQ ID NOs: 36-39
<220> FEATURE:
<221> NAME/KEY: DOMAIN
<222> LOCATION: (1)..(104)
<223> OTHER INFORMATION:

<400> SEQUENCE: 139

Glu Phe Ala Ser Leu Gln Lys Asn Gln Lys Tyr Ser Glu His Phe Ser
1               5                   10                  15

Ile His Cys Cys Pro Pro Phe Thr Phe Leu Asn Ser Lys Lys Glu Ile
                20                  25                  30

Gly Ser Gln Lys Lys Glu Glu Asp Trp Ile Cys Cys Ala Cys Gln Lys
            35                  40                  45

Thr Arg Thr Ser Arg Arg Ala Lys Ser Pro Gln Arg Pro Lys Gly Ser
    50                  55                  60

Lys Gln Gln Pro Arg Ser Ser Pro Leu Arg Gly Pro Gly Ala Ser Arg
65                  70                  75                  80

Gly Gly Ser Ser Arg Ala Lys Pro Pro Gln Arg Pro Lys Gln Gln Pro
                85                  90                  95
```

Ala Ala Pro Pro Ala Val Leu Glu
            100

<210> SEQ ID NO 140
<211> LENGTH: 69
<212> TYPE: DNA
<213> ORGANISM: Artificial Sequence
<220> FEATURE:
<223> OTHER INFORMATION: PLP.p1 - primer for construction of the shPLP
      gene of SEQ ID NO:154.

<400> SEQUENCE: 140
gaattcgcta gcctcgagga ctacaagacc accatctgcg gcaagggcct gagcgcaacg    60
gtaacaggg                                                            69

<210> SEQ ID NO 141
<211> LENGTH: 69
<212> TYPE: DNA
<213> ORGANISM: Artificial Sequence
<220> FEATURE:
<223> OTHER INFORMATION: PLP.p2 (rev) - primer for construction of the
      shPLP gene of SEQ ID NO:154.

<400> SEQUENCE: 141
agcttgatgt tggccacggg aaccgcgccc cttctgtgac cccttctggc ccctgttac    60 cgttgcgct                                                            69

<210> SEQ ID NO 142
<211> LENGTH: 69
<212> TYPE: DNA
<213> ORGANISM: Artificial Sequence
<220> FEATURE:
<223> OTHER INFORMATION: PLP.p3 - primer for construction of the shPLP
      gene of SEQ ID NO:154.

<400> SEQUENCE: 142
cgtggccaac atcaagctca ttctttggag cgcgtgtgtc attgtttggg caaatggcta    60
ggccatccg                                                            69

<210> SEQ ID NO 143
<211> LENGTH: 69
<212> TYPE: DNA
<213> ORGANISM: Artificial Sequence
<220> FEATURE:
<223> OTHER INFORMATION: PLP.p4 (rev) - primer for construction of the
      shPLP gene of SEQ ID NO: 154.

<400> SEQUENCE: 143
agactggcag gtggtccagg tgttgaagta aatgtacacc gagcccttgt ccggatggcc    60
tagccattt                                                            69

<210> SEQ ID NO 144
<211> LENGTH: 69
<212> TYPE: DNA
<213> ORGANISM: Artificial Sequence
<220> FEATURE:
<223> OTHER INFORMATION: PLP.p5 - primer for construction of the shPLP
      gene of SEQ ID NO:154.

<400> SEQUENCE: 144
tggaccacct gccagtctat tgccttcccg agcaagacct ctgccagtat cggcagtctc    60
tgtggcagc                                                            69

```
<210> SEQ ID NO 145
<211> LENGTH: 70
<212> TYPE: DNA
<213> ORGANISM: Artificial Sequence
<220> FEATURE:
<223> OTHER INFORMATION: PLP.p6 (rev) - primer for construction of the
      shPLP gene of SEQ ID NO:154.

<400> SEQUENCE: 145
accatacatg cgggcatcag cacagagact gccgatactg cagaggtct tgctgccaca       60 gagactgccv                                                            70

<210> SEQ ID NO 146
<211> LENGTH: 69
<212> TYPE: DNA
<213> ORGANISM: Artificial Sequence
<220> FEATURE:
<223> OTHER INFORMATION: PLP.p7 - primer for construction of the shPLP
      gene of SEQ ID NO:154.

<400> SEQUENCE: 146
gatgcccgca tgtatggtgt tggctctatt gccttcccga gcaagacctc tgccagtatt     60
ggcagtctc                                                             69

<210> SEQ ID NO 147
<211> LENGTH: 69
<212> TYPE: DNA
<213> ORGANISM: Artificial Sequence
<220> FEATURE:
<223> OTHER INFORMATION: PLP.p8 (rev) - primer for construction of the
      shPLP gene of SEQ ID NO: 154.

<400> SEQUENCE: 147
gccacaaacc ttgccaggga agccgagcc atacatgcgg gcatcagcac agagactgcc      60
aatactggc                                                             69

<210> SEQ ID NO 148
<211> LENGTH: 69
<212> TYPE: DNA
<213> ORGANISM: Artificial Sequence
<220> FEATURE:
<223> OTHER INFORMATION: PLP.p9 - primer for construction of the shPLP
      gene of SEQ ID NO:154.

<400> SEQUENCE: 148
cctggcaagg tttgtggctc caaccttctg tccatctgca aaacagcgga gttccaaatg     60
accttccac                                                             69

<210> SEQ ID NO 149
<211> LENGTH: 69
<212> TYPE: DNA
<213> ORGANISM: Artificial Sequence
<220> FEATURE:
<223> OTHER INFORMATION: PLP.p10 (rev) - primer for construction of the
      shPLP gene of SEQ ID NO: 154.

<400> SEQUENCE: 149
gagtttaagg acggcaaagt tgtaagtgga tccaaatgca gcaataaaca ggtggaaggt     60
catttggaa                                                             69

<210> SEQ ID NO 150
<211> LENGTH: 72
<212> TYPE: DNA
<213> ORGANISM: Artificial Sequence
<220> FEATURE:
```

-continued

<223> OTHER INFORMATION: PLP.p11 - primer for construction of the shPLP
      gene of SEQ ID NO: 154.

<400> SEQUENCE: 150
tttgccgtcc ttaaactcat gggccgtggc accaagttct ctggtcatga agccctcact    60
ggcacagaaa ag                                                        72

<210> SEQ ID NO 151
<211> LENGTH: 69
<212> TYPE: DNA
<213> ORGANISM: Artificial Sequence
<220> FEATURE:
<223> OTHER INFORMATION: PLP.p12 (rev) - primer for construction of the
      shPLP gene of SEQ ID NO: 154.

<400> SEQUENCE: 151
cgctcatgat caatagtctt ggtagttttt ggagaaatag gtctcaatca gcttttctgt    60
gccagtgag                                                            69

<210> SEQ ID NO 152
<211> LENGTH: 36
<212> TYPE: DNA
<213> ORGANISM: Artificial Sequence
<220> FEATURE:
<223> OTHER INFORMATION: PLP.p1a - primer for amplification of the shPLP
      gene of SEQ ID NO: 154.

<400> SEQUENCE: 152
gaattcgcta gcctcgagga ctacaagacc accatc                              36

<210> SEQ ID NO 153
<211> LENGTH: 42
<212> TYPE: DNA
<213> ORGANISM: Artificial Sequence
<220> FEATURE:
<223> OTHER INFORMATION: PLP.p12a - primer for amplification of the
      shPLP gene of SEQ ID NO: 154.

<400> SEQUENCE: 153
taagcttgcg gccgctcatg atcaatagtc ttggtagttt tt                       42

Figure 5:
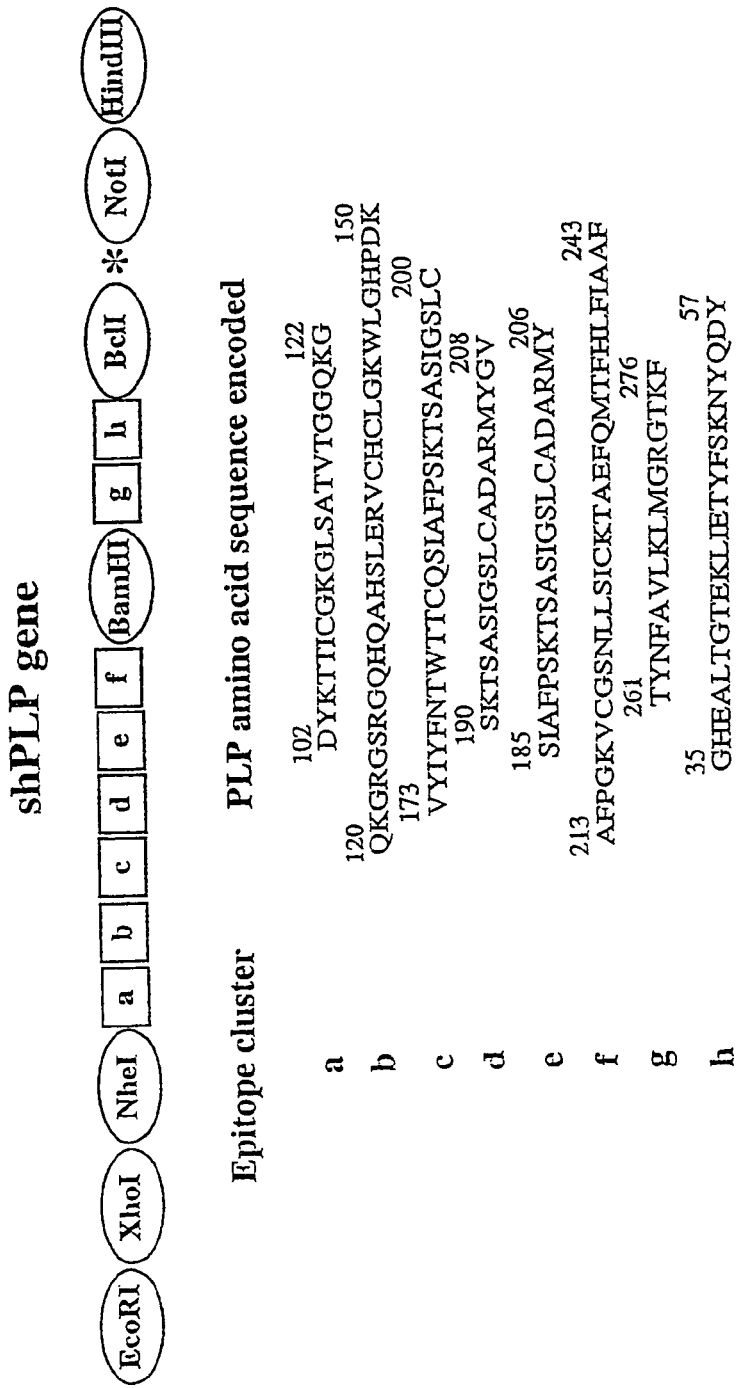
FIG. 5 depicts a scheme of the herein designated shPLP gene in which the sequences of epitope clusters a-h are SEQ ID NO:40-45, 47 and 46, respectively.

<210> SEQ ID NO 154
<211> LENGTH: 645
<212> TYPE: DNA
<213> ORGANISM: Artificial Sequence
<220> FEATURE:
<223> OTHER INFORMATION: shPLP synthetic gene construct comprising
      nucleotides coding for the amino acids of SEQ ID NOs: 40-47 and
      restriction sites as depicted in Fig 5.

<400> SEQUENCE: 154
gaattcgcta gcctcgagga ctacaagacc accatctgcg gcaagggcct gagcgcaacg    60
gtaacagggg gccagaaggg gtcacagaag gggcgcggtt cccgtggcca acatcaagct   120
cattctttgg agcgcgtgtg tcattgtttg gcaaatggc taggccatcc ggacaagggc   180
tcggtgtaca tttacttcaa cacctggacc acctgccagt ctattgcctt cccgagcaag   240
acctctgcca gtatcggcag tctctgtggc agcaagacct ctgccagtat cggcagtctc   300
tgtgctgatg cccgcatgta tggtgttggc tctattgcct cccgagcaa gacctctgcc   360 agtattggca gtctctgtgc tgatgcccgc atgtatggct cggctttccc tggcaaggtt   420
tgtggctcca accttctgtc catctgcaaa acagcggagt tccaaatgac cttccacctg   480
tttattgctg catttggatc cacttacaac tttgccgtcc ttaaactcat gggccgtggc   540

```
accaagttct ctggtcatga agccctcact ggcacagaaa agctgattga gacctatttc    600
tccaaaaact accaagacta ttgatcatga gcggccgcaa gctta                    645
```

<210> SEQ ID NO 155
<211> LENGTH: 207
<212> TYPE: PRT
<213> ORGANISM: Artificial Sequence
<220> FEATURE:
<223> OTHER INFORMATION: shPLP - polypeptide containing the peptides of
      SEQ ID NOs: 40-47.
<220> FEATURE:
<221> NAME/KEY: DOMAIN
<222> LOCATION: (1)..(207)
<223> OTHER INFORMATION:

<400> SEQUENCE: 155

```
Glu Phe Ala Ser Leu Glu Asp Tyr Lys Thr Thr Ile Cys Gly Lys Gly
1               5                   10                  15

Leu Ser Ala Thr Val Thr Gly Gly Gln Lys Gly Ser Gln Lys Gly Arg
            20                  25                  30

Gly Ser Arg Gly Gln His Gln Ala His Ser Leu Glu Arg Val Cys His
        35                  40                  45

Cys Leu Gly Lys Trp Leu Gly His Pro Asp Lys Gly Ser Val Tyr Ile
    50                  55                  60

Tyr Phe Asn Thr Trp Thr Thr Cys Gln Ser Ile Ala Phe Pro Ser Lys
65                  70                  75                  80

Thr Ser Ala Ser Ile Gly Ser Leu Cys Gly Ser Lys Thr Ser Ala Ser
                85                  90                  95

Ile Gly Ser Leu Cys Ala Asp Ala Arg Met Tyr Gly Val Gly Ser Ile
            100                 105                 110

Ala Phe Pro Ser Lys Thr Ser Ala Ser Ile Gly Ser Leu Cys Ala Asp
        115                 120                 125

Ala Arg Met Tyr Gly Ser Ala Phe Pro Gly Lys Val Cys Gly Ser Asn
    130                 135                 140

Leu Leu Ser Ile Cys Lys Thr Ala Glu Phe Gln Met Thr Phe His Leu
145                 150                 155                 160

Phe Ile Ala Ala Phe Gly Ser Thr Tyr Asn Phe Ala Val Leu Lys Leu
                165                 170                 175

Met Gly Arg Gly Thr Lys Phe Ser Gly His Glu Ala Leu Thr Gly Thr
            180                 185                 190

Glu Lys Leu Ile Glu Thr Tyr Phe Ser Lys Asn Tyr Gln Asp Tyr
        195                 200                 205
```

<210> SEQ ID NO 156
<211> LENGTH: 75
<212> TYPE: DNA
<213> ORGANISM: Artificial Sequence
<220> FEATURE:
<223> OTHER INFORMATION: MOG.AL.p1 - primer for construction of the
      shMOG-AL gene of SEQ ID NO: 87.

<400> SEQUENCE: 156

```
gaattcgcta gcgtggggtg gtatcgtcca gccttctctc gtgtggttgc tctgtaccgc    60
aatggcaagg accaa                                                     75
```

<210> SEQ ID NO 157
<211> LENGTH: 72
<212> TYPE: DNA
<213> ORGANISM: Artificial Sequence
<220> FEATURE:
<223> OTHER INFORMATION: MOG.AL.p2 (rev) - primer for construction of the shMOG-AL gene of SEQ ID NO: 87.

<400> SEQUENCE: 157
gtacagatga accaccgcag agaatggcgg acgataccac cccacgctgc catcttggtc    60
cttgccattg cg                                                       72

<210> SEQ ID NO 158
<211> LENGTH: 72
<212> TYPE: DNA
<213> ORGANISM: Artificial Sequence
<220> FEATURE:
<223> OTHER INFORMATION: MOG.AL.p3 - primer for construction of the
      shMOG-AL gene of SEQ ID NO: 87.

<400> SEQUENCE: 158
gcggtggttc atctgtacag aaatggcaag ggctcttatc gtggccgtac tgagctgctg    60
gcagatgcta tt                                                       72

<210> SEQ ID NO 159
<211> LENGTH: 72
<212> TYPE: DNA
<213> ORGANISM: Artificial Sequence
<220> FEATURE:
<223> OTHER INFORMATION: MOG.AL.p4 (rev) - primer for construction of
      the shMOG-AL gene of SEQ ID NO: 87.

<400> SEQUENCE: 159
tccttcatca gagaaacgta cattcgcgat cctcagagtc gcctttccct caccaatagc    60
atctgccagc ag                                                       72

<210> SEQ ID NO 160
<211> LENGTH: 75
<212> TYPE: DNA
<213> ORGANISM: Artificial Sequence
<220> FEATURE:
<223> OTHER INFORMATION: MOG.AL.p5 - primer for construction of the
      shMOG-AL gene of SEQ ID NO: 87.

<400> SEQUENCE: 160
cgtttctctg atgaaggagg tagcggtgag ggaaaggtgg ctctccgtat ccgggctgta    60
cgcttctctg atgaa                                                    75

<210> SEQ ID NO 161
<211> LENGTH: 72
<212> TYPE: DNA
<213> ORGANISM: Artificial Sequence
<220> FEATURE:
<223> OTHER INFORMATION: MOG.AL.p6 (rev) - primer for construction of
      the shMOG-AL gene of SEQ ID NO: 87.

<400> SEQUENCE: 161
ttcatccccg accagagccg cgatacggtg tcgtggtcca gatctgaaac ctccttcatc    60
agagaagcgt ac                                                       72

<210> SEQ ID NO 162
<211> LENGTH: 72
<212> TYPE: DNA
<213> ORGANISM: Artificial Sequence
<220> FEATURE:
<223> OTHER INFORMATION: MOG.AL.p7 - primer for construction of the
      shMOG-AL gene of SEQ ID NO: 87.

<400> SEQUENCE: 162
gctctggtcg gggatgaagt ggaattggca tctcgcatct ctccggggaa gaacgctggc    60

```
tctctgcatc ga                                                           72

<210> SEQ ID NO 163
<211> LENGTH: 65
<212> TYPE: DNA
<213> ORGANISM: Artificial Sequence
<220> FEATURE:
<223> OTHER INFORMATION: MOG.AL.p8 (rev) - primer for construction of
      the shMOG-AL gene of SEQ ID NO: 87.

<400> SEQUENCE: 163
gatccgaacg gatttcgcag ctcttcaagg gcttgccctg caagacgtcg atgcagagag       60
ccagc                                                                   65

<210> SEQ ID NO 164
<211> LENGTH: 30
<212> TYPE: DNA
<213> ORGANISM: Artificial Sequence
<220> FEATURE:
<223> OTHER INFORMATION: MOG.AL.p1a - primer for amplification of the
      shMOG-AL gene of SEQ ID NO: 87.

<400> SEQUENCE: 164
gaattcgcta gcgtggggtg gtatcgtcca                                        30

<210> SEQ ID NO 165
<211> LENGTH: 36
<212> TYPE: DNA
<213> ORGANISM: Artificial Sequence
<220> FEATURE:
<223> OTHER INFORMATION: MOG.AL.p8a (rev) - primer for amplification of
      the shMOG-AL gene of SEQ ID NO: 87.

<400> SEQUENCE: 165
aagctttcag gatccgaacg gatttcgcag ctcttc                                 36

<210> SEQ ID NO 166
<211> LENGTH: 150
<212> TYPE: PRT
<213> ORGANISM: Artificial Sequence
<220> FEATURE:
<223> OTHER INFORMATION: shMOG-AL - polypeptide containing the peptides
      of SEQ ID NOs: 48-53
<220> FEATURE:
<221> NAME/KEY: DOMAIN
<222> LOCATION: (1)..(150)
<223> OTHER INFORMATION:

<400> SEQUENCE: 166

Glu Phe Ala Ser Val Gly Trp Tyr Arg Pro Ala Phe Ser Arg Val Val
1               5                   10                  15

Ala Leu Tyr Arg Asn Gly Lys Asp Gln Asp Gly Ser Val Gly Trp Tyr
            20                  25                  30

Arg Pro Pro Phe Ser Ala Val Val His Leu Tyr Arg Asn Gly Lys Gly
        35                  40                  45

Ser Tyr Arg Gly Arg Thr Glu Leu Leu Ala Asp Ala Ile Gly Glu Gly
    50                  55                  60

Lys Ala Thr Leu Arg Ile Ala Asn Val Arg Phe Ser Asp Glu Gly Gly
65                  70                  75                  80

Ser Gly Glu Gly Lys Val Ala Leu Arg Ile Arg Ala Val Arg Phe Ser
                85                  90                  95

Asp Glu Gly Gly Phe Arg Ser Gly Pro Arg His Arg Ile Ala Ala Leu
            100                 105                 110
```

```
Val Gly Asp Glu Val Glu Leu Ala Ser Arg Ile Ser Pro Gly Lys Asn
        115                 120                 125

Ala Gly Ser Leu His Arg Arg Leu Ala Gly Gln Ala Leu Glu Glu Leu
    130                 135                 140

Arg Asn Pro Phe Gly Ser
145                 150
```

```
<210> SEQ ID NO 167
<211> LENGTH: 72
<212> TYPE: DNA
<213> ORGANISM: Artificial Sequence
<220> FEATURE:
<223> OTHER INFORMATION: MBP.AL.p1- primer for construction of the
      shMBP-AL gene of SEQ ID NO: 88.

<400> SEQUENCE: 167
gaattcgcta gcggatccga tgaaaacccg gtagtccact tcttcgcgaa cattgtgacg    60
cctcgcactc ca                                                       72

<210> SEQ ID NO 168
<211> LENGTH: 78
<212> TYPE: DNA
<213> ORGANISM: Artificial Sequence
<220> FEATURE:
<223> OTHER INFORMATION: MBP.AL.p2 (rev) - primer for construction of
      the shMBP-AL gene of
      SEQ ID NO: 88.

<400> SEQUENCE: 168
cgtcgcaatg ttcttgaaga aggcgactac tgggttttca gagccctgag acggcggtgg    60
agtgcgaggc gtcacaat                                                 78

<210> SEQ ID NO 169
<211> LENGTH: 75
<212> TYPE: DNA
<213> ORGANISM: Artificial Sequence
<220> FEATURE:
<223> OTHER INFORMATION: MBP.AL.p3 - primer for construction of the
      shMBP-AL gene of SEQ ID NO: 88.

<400> SEQUENCE: 169
ttcaagaaca ttgcgacgcc acgcacacca ccgccgtcgc agggatcggc tcacaaggga    60
ttcaagggag tcgct                                                    75

<210> SEQ ID NO 170
<211> LENGTH: 72
<212> TYPE: DNA
<213> ORGANISM: Artificial Sequence
<220> FEATURE:
<223> OTHER INFORMATION: MBP.AL.p4 (rev) - primer for construction of
      the shMBP-AL gene of SEQ ID NO: 88.

<400> SEQUENCE: 170
tttagaaagc gtgccggacc ccagcttaaa aattttggaa agcgtgccct gggcagcgac    60
tcccttgaat cc                                                       72

<210> SEQ ID NO 171
<211> LENGTH: 75
<212> TYPE: DNA
<213> ORGANISM: Artificial Sequence
<220> FEATURE:
<223> OTHER INFORMATION: MBP.AL.p5 - primer for construction of the
      shMBP-AL gene of SEQ ID NO: 88.

<400> SEQUENCE: 171
```

```
tccggcacgc tttctaaaat tgctaagctg ggaggacgcg cgagccgctc tggatcgccg    60
atggctcgtc gcggg                                                    75

<210> SEQ ID NO 172
<211> LENGTH: 75
<212> TYPE: DNA
<213> ORGANISM: Artificial Sequence
<220> FEATURE:
<223> OTHER INFORMATION: MBP.AL.p6 (rev)- primer for construction of
      the shMBP-AL gene of SEQ ID NO: 88.

<400> SEQUENCE: 172
aattttggaa agcgcgccct gggcatcgac tcccgcgaat cccttgtgag cagaggaccc    60
gcgacgagcc atcgg                                                    75

<210> SEQ ID NO 173
<211> LENGTH: 75
<212> TYPE: DNA
<213> ORGANISM: Artificial Sequence
<220> FEATURE:
<223> OTHER INFORMATION: MBP.AL.p7 - primer for construction of the
      shMBP-AL gene of SEQ ID NO: 88.

<400> SEQUENCE: 173
ggcgcgcttt ccaaaatttt taagctggga ggatctcagc ggcacggatc tgcgtacctg    60
gccactgcaa gcacg                                                    75

<210> SEQ ID NO 174
<211> LENGTH: 75
<212> TYPE: DNA
<213> ORGANISM: Artificial Sequence
<220> FEATURE:
<223> OTHER INFORMATION: MBP.AL.p8 (rev) - primer for construction of
      the shMBP-AL gene of SEQ ID NO: 88.

<400> SEQUENCE: 174
gtgccgtgga aggaagccat gccgtctaga aaggaagcca tgccgggctg cgtccatcgt    60
gcttgcagtg gccag                                                    75

<210> SEQ ID NO 175
<211> LENGTH: 75
<212> TYPE: DNA
<213> ORGANISM: Artificial Sequence
<220> FEATURE:
<223> OTHER INFORMATION: MBP.AL.p9 - primer for construction of the
      shMBP-AL gene of SEQ I D NO: 88.

<400> SEQUENCE: 175
ggcttccttc cacggcaccg tgccacgggc atccttgact ccatcgggcg cttctttggt    60
tccggcttcc tgcca                                                    75

<210> SEQ ID NO 176
<211> LENGTH: 72
<212> TYPE: DNA
<213> ORGANISM: Artificial Sequence
<220> FEATURE:
<223> OTHER INFORMATION: MBP.AL.p10 (rev) - primer for construction of
      the shMBP-AL gene of SEQ ID NO: 88.

<400> SEQUENCE: 176
tcaactagta aagaagcgcc cgatggagtc aaggatgccc gtgtctgcgt gacgtggcag    60
gaagccggaa cc                                                       72
```

<210> SEQ ID NO 177
<211> LENGTH: 36
<212> TYPE: DNA
<213> ORGANISM: Artificial Sequence
<220> FEATURE:
<223> OTHER INFORMATION: MBP.AL.p1a - primer for amplification of the
shMBP-AL gene of SEQ ID NO: 88.

<400> SEQUENCE: 177
gaattcgcta gcggatccga tgaaaacccg gtagtc                                36

<210> SEQ ID NO 178
<211> LENGTH: 36
<212> TYPE: DNA
<213> ORGANISM: Artificial Sequence
<220> FEATURE:
<223> OTHER INFORMATION: MBP.AL.p10a (rev) - primer for amplification
of the shMBP-AL gene of SEQ ID NO: 88.

<400> SEQUENCE: 178
aagctttcaa ctagtaaaga agcgcccgat ggagtc                                36

<210> SEQ ID NO 179
<211> LENGTH: 192
<212> TYPE: PRT
<213> ORGANISM: Artificial Sequence
<220> FEATURE:
<223> OTHER INFORMATION: shMBP-AL - polypeptide containing the peptides
of SEQ ID NOs: 54-61
<220> FEATURE:
<221> NAME/KEY: DOMAIN
<222> LOCATION: (1)..(192)
<223> OTHER INFORMATION:

<400> SEQUENCE: 179

Glu Phe Ala Ser Gly Ser Asp Glu Asn Pro Val Val His Phe Phe Ala
1               5                   10                  15

Asn Ile Val Thr Pro Arg Thr Pro Pro Ser Gln Gly Ser Glu Asn
            20                  25                  30

Pro Val Val Ala Phe Phe Lys Asn Ile Ala Thr Pro Arg Thr Pro Pro
        35                  40                  45

Pro Ser Gln Gly Ser Ala His Lys Gly Phe Lys Gly Val Ala Ala Gln
    50                  55                  60

Gly Thr Leu Ser Lys Ile Phe Lys Leu Gly Gly Thr Leu Ser Lys
65                  70                  75                  80

Ile Ala Lys Leu Gly Gly Arg Ala Ser Arg Ser Gly Ser Pro Met Ala
                85                  90                  95

Arg Arg Gly Ser Ser Ala His Lys Gly Phe Ala Gly Val Asp Ala Gln
            100                 105                 110

Gly Ala Leu Ser Lys Ile Phe Lys Leu Gly Gly Ser Gln Arg His Gly
        115                 120                 125

Ser Ala Tyr Leu Ala Thr Ala Ser Thr Met Asp Ala Ala Arg His Gly
    130                 135                 140

Phe Leu Ser Arg Arg His Gly Phe Leu Pro Arg His Arg Ala Thr Gly
145                 150                 155                 160

Ile Leu Asp Ser Ile Gly Arg Phe Phe Gly Ser Gly Phe Leu Pro Arg
                165                 170                 175

His Ala Asp Thr Gly Ile Leu Asp Ser Ile Gly Arg Phe Phe Thr Ser
            180                 185                 190

<210> SEQ ID NO 180
<211> LENGTH: 69

```
<212> TYPE: DNA
<213> ORGANISM: Artificial Sequence
<220> FEATURE:
<223> OTHER INFORMATION: OSP.AL.p1 - primer for construction of the
      shOSP-AL gene of SEQ ID NO: 89.

<400> SEQUENCE: 180
gaattcacta gttccaaggg gctggcggcc gactgcgtcg cggccacggg gctgtacgcc    60
tgcaagccg                                                           69

<210> SEQ ID NO 181
<211> LENGTH: 69
<212> TYPE: DNA
<213> ORGANISM: Artificial Sequence
<220> FEATURE:
<223> OTHER INFORMATION: OSP.AL.p2 (rev) - primer for construction of
      the shOSP-AL gene of SEQ ID NO: 89.

<400> SEQUENCE: 181
gcggcaggtc ggagaaccca cgtagcccgg caggataagg atgtccgcca gcggcttgca    60
ggcgtacag                                                           69

<210> SEQ ID NO 182
<211> LENGTH: 69
<212> TYPE: DNA
<213> ORGANISM: Artificial Sequence
<220> FEATURE:
<223> OTHER INFORMATION: OSP.AL.p3 - primer for construction of the
      shOSP-AL gene of SEQ ID NO: 89.

<400> SEQUENCE: 182
ggttctccga cctgccgcaa gctggctgag ctgggctcca aggggctggc ggccgactgc    60
gtcgcggcc                                                           69

<210> SEQ ID NO 183
<211> LENGTH: 69
<212> TYPE: DNA
<213> ORGANISM: Artificial Sequence
<220> FEATURE:
<223> OTHER INFORMATION: OSP.AL.p4 (rev) - primer for construction of
      the shOSP-AL gene of SEQ ID NO: 89.

<400> SEQUENCE: 183
gccaagctca gccagcttgc gggaggtgct accgcaggcg tacagccccg tggccgcgac    60
gcagtcggc                                                           69

<210> SEQ ID NO 184
<211> LENGTH: 69
<212> TYPE: DNA
<213> ORGANISM: Artificial Sequence
<220> FEATURE:
<223> OTHER INFORMATION: OSP.AL.p5- primer for construction of the
      shOSP-AL gene of SEQ ID NO: 89.

<400> SEQUENCE: 184
aagctggctg agcttggctc tgcggggctg tgggccgcct gcgtcatggc cacggggttg    60
taccactgc                                                           69

<210> SEQ ID NO 185
<211> LENGTH: 69
<212> TYPE: DNA
<213> ORGANISM: Artificial Sequence
<220> FEATURE:
<223> OTHER INFORMATION: OSP.AL.p6 (rev) - primer for construction of
      the shOSP-AL gene of SEQ ID NO: 89.
```

```
<400> SEQUENCE: 185
gcccatccgg atggaggcaa gaacagtaag cagcagtaaa atggcagatc cgcagtggta    60
caaccccgt                                                            69

<210> SEQ ID NO 186
<211> LENGTH: 69
<212> TYPE: DNA
<213> ORGANISM: Artificial Sequence
<220> FEATURE:
<223> OTHER INFORMATION: OSP.AL.p7 - primer for construction of the
      shOSP-AL gene of SEQ ID NO: 89.

<400> SEQUENCE: 186
gcctccatcc ggatgggcca ggagccgggt agcaaccgtt tctactacac tgcgggctct    60
gcctccccg                                                            69

<210> SEQ ID NO 187
<211> LENGTH: 69
<212> TYPE: DNA
<213> ORGANISM: Artificial Sequence
<220> FEATURE:
<223> OTHER INFORMATION: OSP.AL.p8 (rev) - primer for construction of
      the shOSP-AL gene of SEQ ID NO: 89.

<400> SEQUENCE: 187
cggggagcta gagcccgcag tgctacctac gtgggcactc ccgcatgag tcggggaggc     60 agagcccgc                                                            69

<210> SEQ ID NO 188
<211> LENGTH: 69
<212> TYPE: DNA
<213> ORGANISM: Artificial Sequence
<220> FEATURE:
<223> OTHER INFORMATION: OSP.AL.p9 - primer for construction of the
      shOSP-AL gene of SEQ ID NO: 89.

<400> SEQUENCE: 188
gcgggctcta gctccccgac tgctgcgaag agtgcccacg taatgcattg gatcgggtc     60 atcgtgacc                                                            69

<210> SEQ ID NO 189
<211> LENGTH: 69
<212> TYPE: DNA
<213> ORGANISM: Artificial Sequence
<220> FEATURE:
<223> OTHER INFORMATION: OSP.AL.p10 (rev) - primer for construction of
      the shOSP-AL gene of SEQ ID NO: 89.

<400> SEQUENCE: 189
gctgcctggg atggtgtagc cggaggtcac cacccagtca ttggcggagg tggtcacgat    60
gaccccgat                                                            69

<210> SEQ ID NO 190
<211> LENGTH: 69
<212> TYPE: DNA
<213> ORGANISM: Artificial Sequence
<220> FEATURE:
<223> OTHER INFORMATION: OSP.AL.p11- primer for construction of the
      shOSP-AL gene of SEQ ID NO: 89.

<400> SEQUENCE: 190
tacaccatcc caggcagcgt tttgcttatt ctgcttgctg cctgcgccct tgttgccacc    60
```

-continued atctggttc 69

<210> SEQ ID NO 191
<211> LENGTH: 63
<212> TYPE: DNA
<213> ORGANISM: Artificial Sequence
<220> FEATURE:
<223> OTHER INFORMATION: OSP.AL.p12 (rev) - primer for construction of
the shOSP-AL gene of SEQ ID NO: 89.

<400> SEQUENCE: 191
aagctttcac tgcaggatgg tggtctcacg gtgggcgcac acagcgaacc agatggtggc 60
aac 63

<210> SEQ ID NO 192
<211> LENGTH: 30
<212> TYPE: DNA
<213> ORGANISM: Artificial Sequence
<220> FEATURE:
<223> OTHER INFORMATION: OSP.AL.p1a - primer for amplification of the
shOSP-AL gene of SEQ ID NO: 89.

<400> SEQUENCE: 192
gaattcacta gttccaaggg gctggcggcc 30

<210> SEQ ID NO 193
<211> LENGTH: 36
<212> TYPE: DNA
<213> ORGANISM: Artificial Sequence
<220> FEATURE:
<223> OTHER INFORMATION: OSP.AL.p12a (rev) - primer for amplification of
the shOSP-AL gene of SEQ ID NO: 89.

<400> SEQUENCE: 193
aagctttcac tgcaggatgg tggtctcacg gtgggc 36

<210> SEQ ID NO 194
<211> LENGTH: 205
<212> TYPE: PRT
<213> ORGANISM: Artificial Sequence
<220> FEATURE:
<223> OTHER INFORMATION: shOSP-AL - polypeptide containing the peptides
of SEQ ID NOs: 62-69
<220> FEATURE:
<221> NAME/KEY: DOMAIN
<222> LOCATION: (1)..(205)
<223> OTHER INFORMATION:

<400> SEQUENCE: 194

Glu Phe Thr Ser Ser Lys Gly Leu Ala Ala Asp Cys Val Ala Ala Thr
1               5                   10                  15

Gly Leu Tyr Ala Cys Lys Pro Leu Ala Asp Ile Leu Ile Leu Pro Gly
            20                  25                  30

Tyr Val Gly Ser Pro Thr Cys Arg Lys Leu Ala Glu Leu Gly Ser Lys
        35                  40                  45

Gly Leu Ala Ala Asp Cys Val Ala Ala Thr Gly Leu Tyr Ala Cys Gly
    50                  55                  60

Ser Thr Ser Arg Lys Leu Ala Glu Leu Gly Ser Ala Gly Leu Trp Ala
65                  70                  75                  80

Ala Cys Val Met Ala Thr Gly Leu Tyr His Cys Gly Ser Ala Ile Leu
                85                  90                  95

Leu Leu Leu Thr Val Leu Ala Ser Ile Arg Met Gly Gln Glu Pro Gly
            100                 105                 110

Ser Asn Arg Phe Tyr Tyr Thr Ala Gly Ser Ala Ser Pro Thr His Ala

```
            115                 120                 125
Ala Ser Ala His Val Gly Ser Thr Ala Gly Ser Ser Pro Thr Ala
    130                 135                 140

Ala Lys Ser Ala His Val Met His Trp Ile Gly Val Ile Val Thr Thr
145                 150                 155                 160

Ser Ala Asn Asp Trp Val Val Thr Ser Gly Tyr Thr Ile Pro Gly Ser
                165                 170                 175

Val Leu Leu Ile Leu Leu Ala Ala Cys Ala Leu Val Ala Thr Ile Trp
            180                 185                 190

Phe Ala Val Cys Ala His Arg Glu Thr Thr Ile Leu Gln
            195                 200                 205

<210> SEQ ID NO 195
<211> LENGTH: 66
<212> TYPE: DNA
<213> ORGANISM: Artificial Sequence
<220> FEATURE:
<223> OTHER INFORMATION: MOBP.AL.p1 - primer for construction of the
      shMOBP-AL gene of SEQ ID NO: 90.

<400> SEQUENCE: 195
gaattcgcta gcctgcagaa aaaccagaaa tactccgcac acttcagcat tcactgctgc      60
ccgccg                                                                 66

<210> SEQ ID NO 196
<211> LENGTH: 69
<212> TYPE: DNA
<213> ORGANISM: Artificial Sequence
<220> FEATURE:
<223> OTHER INFORMATION: MOBP.AL.p2 (rev)- primer for construction of
      the shMOBP-AL gene of SEQ ID NO: 90.

<400> SEQUENCE: 196
gtcctcctct ttcttgctgc ctatctcctt cttggaattg aggaaggtgg ccggcgggca      60
gcagtgaat                                                              69

<210> SEQ ID NO 197
<211> LENGTH: 69
<212> TYPE: DNA
<213> ORGANISM: Artificial Sequence
<220> FEATURE:
<223> OTHER INFORMATION: MOBP.AL.p3- primer for construction of the
      shMOBP-AL gene of SEQ ID NO: 90.

<400> SEQUENCE: 197
agcaagaaag aggaggactg ggcctgctgt gcctctcagg cgacccgcac cagcgcccgt      60
gccaagtct                                                              69

<210> SEQ ID NO 198
<211> LENGTH: 69
<212> TYPE: DNA
<213> ORGANISM: Artificial Sequence
<220> FEATURE:
<223> OTHER INFORMATION: MOBP.AL.p4 (rev)- primer for construction of
      the shMOBP-AL gene of SEQ ID NO: 90.

<400> SEQUENCE: 198
tgcaagcggg ctgctgcgcg gctgttgctt cgaacccttc ggccgctgcg gagacttggc      60
acgggcgct                                                              69

<210> SEQ ID NO 199
<211> LENGTH: 69
```

```
<212> TYPE: DNA
<213> ORGANISM: Artificial Sequence
<220> FEATURE:
<223> OTHER INFORMATION: MOBP.AL.p5 - primer for construction of the
      shMOBP-AL gene of SEQ ID NO: 90.

<400> SEQUENCE: 199
cgcagcagcc cgcttgcagg gccaggagcc agccgtgggg ggtcccgtgc caagtcccct    60
cagaggccg                                                            69

<210> SEQ ID NO 200
<211> LENGTH: 63
<212> TYPE: DNA
<213> ORGANISM: Artificial Sequence
<220> FEATURE:
<223> OTHER INFORMATION: MOBP.AL.p6 (rev)- primer for construction of
      the shMOBP-AL gene of SEQ ID NO: 90.

<400> SEQUENCE: 200
aagctttcac tcgagcaccg ctggcggcgc tgctggctgt tgcgccggcc tctgagggga    60
ctt                                                                  63

<210> SEQ ID NO 201
<211> LENGTH: 36
<212> TYPE: DNA
<213> ORGANISM: Artificial Sequence
<220> FEATURE:
<223> OTHER INFORMATION: MOBP.AL.p1a - primer for amplification of the
      shMOBP-AL gene of SEQ ID NO: 90.

<400> SEQUENCE: 201
gaattcgcta gcctgcagaa aaaccagaaa tactcc                              36

<210> SEQ ID NO 202
<211> LENGTH: 36
<212> TYPE: DNA
<213> ORGANISM: Artificial Sequence
<220> FEATURE:
<223> OTHER INFORMATION: MOBP.AL.p6a (rev)- primer for amplification of
      the shMOBP-AL gene of SEQ ID NO: 90.

<400> SEQUENCE: 202
aagctttcac tcgagcaccg ctggcggcgc tgctgg                              36

<210> SEQ ID NO 203
<211> LENGTH: 102
<212> TYPE: PRT
<213> ORGANISM: Artificial Sequence
<220> FEATURE:
<223> OTHER INFORMATION: shMOBP-AL - polypeptide containing the peptides
      of SEQ ID NOs: 70-73
<220> FEATURE:
<221> NAME/KEY: DOMAIN
<222> LOCATION: (1)..(102)
<223> OTHER INFORMATION:

<400> SEQUENCE: 203

Glu Phe Ala Ser Leu Gln Lys Asn Gln Lys Tyr Ser Ala His Phe Ser
1               5                   10                  15

Ile His Cys Cys Pro Pro Ala Thr Phe Leu Asn Ser Lys Lys Glu Ile
            20                  25                  30

Gly Ser Lys Lys Glu Glu Asp Trp Ala Cys Cys Ala Ser Gln Ala Thr
        35                  40                  45

Arg Thr Ser Ala Arg Ala Lys Ser Pro Gln Pro Lys Gly Ser Lys
    50                  55                  60
```

-continued

Gln Gln Pro Arg Ser Ser Pro Leu Ala Gly Pro Gly Ala Ser Arg Gly
 65                  70                  75                  80

Gly Ser Arg Ala Lys Ser Pro Gln Arg Pro Ala Gln Gln Pro Ala Ala
                 85                  90                  95

Pro Pro Ala Val Leu Glu
            100

<210> SEQ ID NO 204
<211> LENGTH: 69
<212> TYPE: DNA
<213> ORGANISM: Artificial Sequence
<220> FEATURE:
<223> OTHER INFORMATION: PLP.AL.p1 - primer for construction of the
      shPLP-AL gene of SEQ ID NO: 91.

<400> SEQUENCE: 204
gaattcgcta gcctcgagga ctacaagacc accatctccg gcgcgggcct gagcgcaacg    60
gtaactggg                                                           69

<210> SEQ ID NO 205
<211> LENGTH: 69
<212> TYPE: DNA
<213> ORGANISM: Artificial Sequence
<220> FEATURE:
<223> OTHER INFORMATION: PLP.AL.p2 (rev)- primer for construction of the
      shPLP-AL gene of SEQ ID NO: 91.

<400> SEQUENCE: 205
gctcgcgccc ttgccggaga tggtggtctt gtagtcgctt cccttctggc ccccagttac    60
cgttgcgct                                                           69

<210> SEQ ID NO 206
<211> LENGTH: 69
<212> TYPE: DNA
<213> ORGANISM: Artificial Sequence
<220> FEATURE:
<223> OTHER INFORMATION: PLP.AL.p3 - primer for construction of the
      shPLP-AL gene of SEQ ID NO: 91.

<400> SEQUENCE: 206
tccggcaagg gcgcgagcgc aacggtaact gggggccaga agggaagcca gaagggcgt    60 ggttctcgt                                                           69

<210> SEQ ID NO 207
<211> LENGTH: 69
<212> TYPE: DNA
<213> ORGANISM: Artificial Sequence
<220> FEATURE:
<223> OTHER INFORMATION: PLP.AL.p4 (rev)- primer for construction of the
      shPLP-AL gene of SEQ ID NO: 91.

<400> SEQUENCE: 207
ttttcccaaa caatgacaca cacgctccgc agaatgagct tgagcttggc cacgagaacc    60
acgccccctt                                                          69

<210> SEQ ID NO 208
<211> LENGTH: 69
<212> TYPE: DNA
<213> ORGANISM: Artificial Sequence
<220> FEATURE:
<223> OTHER INFORMATION: PLP.AL.p5 - primer for construction of the
      shPLP-AL gene of SEQ ID NO: 91.

<400> SEQUENCE: 208

```
tgtcattgtt tgggaaaagc gcttggacat ccggacaagg gcagcgtgta catttacttc    60
aacacctgg                                                            69
```

<210> SEQ ID NO 209
<211> LENGTH: 69
<212> TYPE: DNA
<213> ORGANISM: Artificial Sequence
<220> FEATURE:
<223> OTHER INFORMATION: PLP.AL.p6 (rev)- primer for construction of the
      shPLP-AL gene of SEQ ID NO: 91.

<400> SEQUENCE: 209

```
gccaatgctg gcagaggtcg cgctcgggaa ggcaatagac tgggaggcgg tccaggtgtt    60
gaagtaaat                                                            69
```

<210> SEQ ID NO 210
<211> LENGTH: 69
<212> TYPE: DNA
<213> ORGANISM: Artificial Sequence
<220> FEATURE:
<223> OTHER INFORMATION: PLP.AL.p7 - primer for construction of the
      shPLP-AL gene of SEQ ID NO: 91.

<400> SEQUENCE: 210

```
acctctgcca gcattggcag cctgtctggc agcaagacct ctgccagcat tggcagcgcc    60
tctgctgat                                                            69
```

<210> SEQ ID NO 211
<211> LENGTH: 69
<212> TYPE: DNA
<213> ORGANISM: Artificial Sequence
<220> FEATURE:
<223> OTHER INFORMATION: PLP.AL.p8 (rev)- primer for construction of the
      shPLP-AL gene of SEQ ID NO: 91.

<400> SEQUENCE: 211

```
agaggtggtc gcggtgttga agtaaatgct cccaacacca tacatacggg catcagcaga    60
ggcgctgcc                                                            69
```

<210> SEQ ID NO 212
<211> LENGTH: 69
<212> TYPE: DNA
<213> ORGANISM: Artificial Sequence
<220> FEATURE:
<223> OTHER INFORMATION: PLP.AL.p9 - primer for construction of the
      shPLP-AL gene of SEQ ID NO: 91.

<400> SEQUENCE: 212

```
aacaccgcga ccacctctca gtctgctgcc ttcccgagca aggcctctgc cagcattggg    60
agctctgct                                                            69
```

<210> SEQ ID NO 213
<211> LENGTH: 69
<212> TYPE: DNA
<213> ORGANISM: Artificial Sequence
<220> FEATURE:
<223> OTHER INFORMATION: PLP.AL.p10 (rev)- primer for construction of
      the shPLP-AL gene of SEQ ID NO: 91.

<400> SEQUENCE: 213

```
ggcatcagca gacaggctgg ctatgctggc agaggccttg ctcgggaagg cagcagagct    60
cccaatgct                                                            69
```

```
<210> SEQ ID NO 214
<211> LENGTH: 69
<212> TYPE: DNA
<213> ORGANISM: Artificial Sequence
<220> FEATURE:
<223> OTHER INFORMATION: PLP.AL.p11 - primer for construction of the
      shPLP-AL gene of SEQ ID NO: 91.

<400> SEQUENCE: 214
agcctgtctg ctgatgcccg aatgtatgga tctcagtcta ttgccttcgc cagcaagacc      60
tctgccagc                                                              69

<210> SEQ ID NO 215
<211> LENGTH: 69
<212> TYPE: DNA
<213> ORGANISM: Artificial Sequence
<220> FEATURE:
<223> OTHER INFORMATION: PLP.AL.p12 (rev)- primer for construction of
      the shPLP-AL gene of SEQ ID NO: 91.

<400> SEQUENCE: 215
gccacaaacc ttgccaggga aagcgctacc atcagcagaa aggctggcaa tgctggcaga      60
ggtcttgct                                                              69

<210> SEQ ID NO 216
<211> LENGTH: 69
<212> TYPE: DNA
<213> ORGANISM: Artificial Sequence
<220> FEATURE:
<223> OTHER INFORMATION: PLP.AL.p13 - primer for construction of the
      shPLP-AL gene of SEQ ID NO: 91.

<400> SEQUENCE: 216
cctggcaagg tttgtggctc tgcccttctg tctatctgca aacagcaga gttccaaatg       60 gggtctatc                                                              69

<210> SEQ ID NO 217
<211> LENGTH: 69
<212> TYPE: DNA
<213> ORGANISM: Artificial Sequence
<220> FEATURE:
<223> OTHER INFORMATION: PLP.AL.p14 (rev)- primer for construction of
      the shPLP-AL gene of SEQ ID NO: 91.

<400> SEQUENCE: 217
aaatgcagca ataaacaggt ggaaggtcgc ttggaactca gcagttttag agatagaccc      60
catttggaa                                                              69

<210> SEQ ID NO 218
<211> LENGTH: 72
<212> TYPE: DNA
<213> ORGANISM: Artificial Sequence
<220> FEATURE:
<223> OTHER INFORMATION: PLP.AL.p15 - primer for construction of the
      shPLP-AL gene of SEQ ID NO: 91.

<400> SEQUENCE: 218
ctgtttattg ctgcatttgg aagcgctttc ccggtcaagg cttgtggctc caacgctctg      60
tccatctgca aa                                                          72

<210> SEQ ID NO 219
<211> LENGTH: 72
<212> TYPE: DNA
<213> ORGANISM: Artificial Sequence
<220> FEATURE:
```

<223> OTHER INFORMATION: PLP.AL.p16 (rev)- primer for construction of
      the shPLP-AL gene of SEQ ID NO: 91.

<400> SEQUENCE: 219
cagtttaagg acggcaaagt tgtaagtgga tccggtcatt tggaactcag cagttttgca    60
gatggacaga gc    72

<210> SEQ ID NO 220
<211> LENGTH: 72
<212> TYPE: DNA
<213> ORGANISM: Artificial Sequence
<220> FEATURE:
<223> OTHER INFORMATION: PLP.AL.p17 - primer for construction of the
      shPLP-AL gene of SEQ ID NO: 91.

<400> SEQUENCE: 220
tttgccgtcc ttaaactggc gggccgtggc accaagttcg gctccggaca tgaagccctg    60
actggcactg aa    72

<210> SEQ ID NO 221
<211> LENGTH: 72
<212> TYPE: DNA
<213> ORGANISM: Artificial Sequence
<220> FEATURE:
<223> OTHER INFORMATION: PLP.AL.p18 (rev)- primer for construction of
      the shPLP-AL gene of SEQ ID NO: 91.

<400> SEQUENCE: 221
cgctcatgat caatagtctt ggtagttttt ggagaaatag gtctcaatta gcgcttcagt    60
gccagtcagg gc    72

<210> SEQ ID NO 222
<211> LENGTH: 36
<212> TYPE: DNA
<213> ORGANISM: Artificial Sequence
<220> FEATURE:
<223> OTHER INFORMATION: PLP.AL.p1a - primer for amplification of the
      shPLP-AL gene of SEQ ID NO: 91.

<400> SEQUENCE: 222
gaattcgcta gcctcgagga ctacaagacc accatc    36

<210> SEQ ID NO 223
<211> LENGTH: 45
<212> TYPE: DNA
<213> ORGANISM: Artificial Sequence
<220> FEATURE:
<223> OTHER INFORMATION: PLP.AL.p18a (rev)- primer for amplification of
      the shPLP-AL gene of SEQ ID NO: 91.

<400> SEQUENCE: 223
taagcttgcg gccgctcatg atcaatagtc ttggtagttt ttgga    45

<210> SEQ ID NO 224
<211> LENGTH: 312
<212> TYPE: PRT
<213> ORGANISM: Artificial Sequence
<220> FEATURE:
<223> OTHER INFORMATION: shPLP-AL - polypeptide containing the peptides
      of SEQ ID NOs: 74-86

<400> SEQUENCE: 224

Glu Phe Ala Ser Leu Glu Asp Tyr Lys Thr Thr Ile Ser Gly Ala Gly
1               5                   10                  15

Leu Ser Ala Thr Val Thr Gly Gly Gln Lys Gly Ser Asp Tyr Lys Thr

```
                    20                  25                  30
Thr Ile Ser Gly Lys Gly Ala Ser Ala Thr Val Thr Gly Gly Gln Lys
                35                  40                  45

Gly Ser Gln Lys Gly Arg Gly Ser Arg Gly Gln Ala Gln Ala His Ser
            50                  55                  60

Ala Glu Arg Val Cys His Cys Leu Gly Lys Ala Leu Gly His Pro Asp
 65                  70                  75                  80

Lys Gly Ser Val Tyr Ile Tyr Phe Asn Thr Trp Thr Ala Ser Gln Ser
                85                  90                  95

Ile Ala Phe Pro Ser Ala Thr Ser Ala Ser Ile Gly Ser Leu Ser Gly
               100                 105                 110

Ser Lys Thr Ser Ala Ser Ile Gly Ser Ala Ser Ala Asp Ala Arg Met
           115                 120                 125

Tyr Gly Val Gly Ser Ile Tyr Phe Asn Thr Ala Thr Thr Ser Gln Ser
       130                 135                 140

Ala Ala Phe Pro Ser Lys Ala Ser Ala Ser Ile Gly Ser Ser Ala Ala
145                 150                 155                 160

Phe Pro Ser Lys Ala Ser Ala Ser Ile Ala Ser Leu Ser Ala Asp Ala
               165                 170                 175

Arg Met Tyr Gly Ser Gln Ser Ile Ala Phe Ala Ser Lys Thr Ser Ala
           180                 185                 190

Ser Ile Ala Ser Leu Ser Ala Asp Gly Ser Ala Phe Pro Gly Lys Val
       195                 200                 205

Cys Gly Ser Ala Leu Leu Ser Ile Cys Lys Thr Ala Glu Phe Gln Met
   210                 215                 220

Gly Ser Ile Ser Lys Thr Ala Glu Phe Gln Ala Thr Phe His Leu Phe
225                 230                 235                 240

Ile Ala Ala Phe Gly Ser Ala Phe Pro Val Lys Ala Cys Gly Ser Asn
               245                 250                 255

Ala Leu Ser Ile Cys Lys Thr Ala Glu Phe Gln Met Thr Gly Ser Thr
           260                 265                 270

Tyr Asn Phe Ala Val Leu Lys Leu Ala Gly Arg Gly Thr Lys Phe Gly
       275                 280                 285

Ser Gly His Glu Ala Leu Thr Gly Thr Glu Ala Leu Ile Glu Thr Tyr
   290                 295                 300

Phe Ser Lys Asn Tyr Gln Asp Tyr
305                 310

<210> SEQ ID NO 225
<211> LENGTH: 2064
<212> TYPE: DNA
<213> ORGANISM: Artificial Sequence
<220> FEATURE:
<223> OTHER INFORMATION: Y-MSPe- synthetic gene comprising the
      nucleotide sequences of SEQ ID NOs: 102, 114, 128, 138, 154 and
      restriction sites as depicted in Fig 6.

<400> SEQUENCE: 225
gaattcgcta gcgtggggtg gtatcgcccg ccattctctc gtgtggttca tctctaccgc    60
aatggcaagg accaagatgg ctcatatcgc ggtcgcacag agctgctgaa agatgctatt   120
ggtgagggca aggtgactct ccgtatccgc aatgtacgtt tctcagatga aggtggtaga   180
tctggcccac gccaccctat ccgggctctg gtcggggatg aagtggaatt gccatgtcgc   240
atctctcctg ggaagaacgc tggctcactg catcgtcgcc tggcagggca attccttgaa   300
gagctgcgta atccgttcgg atccgatgaa aacccggtag tccacttctt caagaacatt   360
```

```
gtgacgcctc gcacaccacc gccgtcgcag ggctcggctc acaagggttt caagggcgtc    420
gatgcccagg gcacgctttc caaaatttttt aagctgtctg gcacgctttc caaaatttttt   480 aagctgggtg gccgcgatag tcgctctggc tcaccgatgg ctcgtcgcgg ttcccagcgc    540
cacggttcca agtacctggc cacagcaagc actatggacc atgcccgtca tggcttcctc    600
tctagacgtc atggcttcct cccacgtcac cgcgacacgg gcatccttga ctccatcggg    660
cgcttcttta ctagttccaa ggggctgtgg gccgactgcg tcatggccac ggggctgtac    720
cactgcaagc cgctggtgga catcctcatc ctgccgggct acgtgggctc tccgacctgc    780
cgcaagctgg atgagctggg ctccaagggg ctgtgggccg actgcgtcat ggccacgggg    840
ctgtaccact gcggttcagc catttttactg ctgctgactg ttcttccgtg catccgtatg    900
ggccaggagc caggttccaa ccgtttctac tacactgcgg gctctagctc cccgactcat    960
gcgaagagtg cccacgtaat gcattggatc ggggtcatcg tgaccacctc caccaatgac   1020
tgggtggtga cctgcggcta caccatccca gggtccgttt tgctcattct gctggctctc   1080
tgcgcccttg ttgccaccat ctggttccct gtgtgcgccc accgtgagac caccatcctg   1140
cagaaaaacc agaagtacag cgaacacttc agcattcact gctgcccgcc gttcaccttc   1200
ctcaattcca agaaggagat tggctctcag aagaaagagg aggactggat ctgctgcgcc   1260
tgccagaaga cccgcaccag ccgccgtgcc aagtctcctc agcgcccgaa gggctctaag   1320
caacagccgc gcagcagccc actccgtggg ccaggcgcta gtcgtggtgg gtcctcccgt   1380
gccaagccgc ctcagcgccc aaagcaacag cctgctgcgc cgccggcggt gctcgaggac   1440
tacaagacca ccatctgcgg caagggcctg agcgcaacgg taacagggg ccagaagggg   1500 tcacagaagg ggcgcggttc ccgtggccaa catcaagctc attctttgga gcgcgtgtgt   1560
cattgtttgg gcaaatggct aggccatccg gacaagggct cggtgtacat ttacttcaac   1620
acctggacca cctgccagtc tattgccttc ccgagcaaga cctctgccag tatcggcagt   1680
ctctgtggca gcaagacctc tgccagtatc ggcagtctct gtgctgatgc ccgcatgtat   1740
ggtgttggct ctattgcctt cccgagcaag acctctgcca gtattggcag tctctgtgct   1800
gatgcccgca tgtatggctc ggcttttccct ggcaaggttt gtggctccaa ccttctgtcc   1860
atctgcaaaa cagcggagtt ccaaatgacc ttccacctgt ttattgctgc atttggatcc   1920
acttacaact ttgccgtcct taaactcatg gccgtggca ccaagttctc tggtcatgaa    1980
gccctcactg gcacagaaaa gctgattgag acctatttct ccaaaaacta ccaagactat   2040
tgatcatgag cggccgcaag ctta                                           2064
```

<210> SEQ ID NO 226
<211> LENGTH: 680
<212> TYPE: PRT
<213> ORGANISM: Artificial Sequence
<220> FEATURE:
<223> OTHER INFORMATION: Polypeptide expressed by the DNA of SEQ ID NO: 225

<400> SEQUENCE: 226

Glu Phe Ala Ser Val Gly Trp Tyr Arg Pro Pro Phe Ser Arg Val Val
1               5                   10                  15

His Leu Tyr Arg Asn Gly Lys Asp Gln Asp Gly Ser Tyr Arg Gly Arg
            20                  25                  30

Thr Glu Leu Leu Lys Asp Ala Ile Gly Glu Gly Lys Val Thr Leu Arg
        35                  40                  45

Ile Arg Asn Val Arg Phe Ser Asp Glu Gly Gly Arg Ser Gly Pro Arg
    50                  55                  60

-continued

```
His Pro Ile Arg Ala Leu Val Gly Asp Glu Val Glu Leu Pro Cys Arg
 65                  70                  75                  80

Ile Ser Pro Gly Lys Asn Ala Gly Ser Leu His Arg Arg Leu Ala Gly
                 85                  90                  95

Gln Phe Leu Glu Glu Leu Arg Asn Pro Phe Gly Ser Asp Glu Asn Pro
            100                 105                 110

Val Val His Phe Phe Lys Asn Ile Val Thr Pro Arg Thr Pro Pro
            115                 120                 125

Ser Gln Gly Ser Ala His Lys Gly Phe Lys Gly Val Asp Ala Gln Gly
130                 135                 140

Thr Leu Ser Lys Ile Phe Lys Leu Ser Gly Thr Leu Ser Lys Ile Phe
145                 150                 155                 160

Lys Leu Gly Gly Arg Asp Ser Arg Ser Gly Ser Pro Met Ala Arg Arg
                165                 170                 175

Gly Ser Gln Arg His Gly Ser Lys Tyr Leu Ala Thr Ala Ser Thr Met
            180                 185                 190

Asp His Ala Arg His Gly Phe Leu Ser Arg Arg His Gly Phe Leu Pro
            195                 200                 205

Arg His Arg Asp Thr Gly Ile Leu Asp Ser Ile Gly Arg Phe Phe Thr
            210                 215                 220

Ser Ser Lys Gly Leu Trp Ala Asp Cys Val Asn Ala Thr Gly Leu Tyr
225                 230                 235                 240

His Cys Lys Pro Leu Val Asp Ile Leu Ile Leu Pro Gly Tyr Val Gly
                245                 250                 255

Ser Pro Thr Cys Arg Lys Leu Asp Glu Leu Gly Ser Lys Gly Leu Trp
            260                 265                 270

Ala Asp Cys Val Met Ala Thr Gly Leu Tyr His Cys Gly Ser Ala Ile
            275                 280                 285

Leu Leu Leu Leu Thr Val Leu Pro Cys Ile Arg Met Gly Gln Glu Pro
290                 295                 300

Gly Ser Asn Arg Phe Tyr Tyr Thr Ala Gly Ser Ser Pro Thr His
305                 310                 315                 320

Ala Lys Ser Ala His Val Met His Trp Ile Gly Val Ile Val Thr Thr
                325                 330                 335

Ser Thr Asn Asp Trp Val Val Thr Cys Gly Tyr Thr Ile Pro Gly Ser
            340                 345                 350

Val Leu Leu Ile Leu Leu Ala Leu Cys Ala Leu Val Ala Thr Ile Trp
            355                 360                 365

Phe Pro Val Cys Ala His Arg Glu Thr Thr Ile Leu Gln Lys Asn Gln
370                 375                 380

Lys Tyr Ser Glu His Phe Ser Ile His Cys Cys Pro Pro Phe Thr Phe
385                 390                 395                 400

Leu Asn Ser Lys Lys Glu Ile Gly Ser Gln Lys Lys Glu Glu Asp Trp
                405                 410                 415

Ile Cys Cys Ala Cys Gln Lys Thr Arg Thr Ser Arg Arg Ala Lys Ser
            420                 425                 430

Pro Gln Arg Pro Lys Gly Ser Lys Gln Gln Pro Arg Ser Ser Pro Leu
            435                 440                 445

Arg Gly Pro Gly Ala Ser Arg Gly Gly Ser Ser Arg Ala Lys Pro Pro
            450                 455                 460

Gln Arg Pro Lys Gln Gln Pro Ala Ala Pro Ala Val Leu Glu Asp
465                 470                 475                 480

Tyr Lys Thr Thr Ile Cys Gly Lys Gly Leu Ser Ala Thr Val Thr Gly
```

```
                    485                 490                 495
Gly Gln Lys Gly Ser Lys Gly Arg Gly Ser Arg Gly Gln His Gln
            500                 505                 510

Ala His Ser Leu Glu Arg Val Cys His Cys Leu Gly Lys Trp Leu Gly
            515                 520                 525

His Pro Asp Lys Gly Ser Val Tyr Ile Tyr Phe Asn Thr Trp Thr Thr
        530                 535                 540

Cys Gln Ser Ile Ala Phe Pro Ser Lys Thr Ser Ala Ser Ile Gly Ser
545                 550                 555                 560

Leu Cys Gly Ser Lys Thr Ser Ala Ser Ile Gly Ser Leu Cys Ala Asp
                565                 570                 575

Ala Arg Met Tyr Gly Val Gly Ser Ile Ala Phe Pro Ser Lys Thr Ser
            580                 585                 590

Ala Ser Ile Gly Ser Leu Cys Ala Asp Ala Arg Met Tyr Gly Ser Ala
            595                 600                 605

Phe Pro Gly Lys Val Cys Gly Ser Asn Leu Leu Ser Ile Cys Lys Thr
        610                 615                 620

Ala Glu Phe Gln Met Thr Phe His Leu Phe Ile Ala Ala Phe Gly Ser
625                 630                 635                 640

Thr Tyr Asn Phe Ala Val Leu Lys Leu Met Gly Arg Gly Thr Lys Phe
                645                 650                 655

Ser Gly His Glu Ala Leu Thr Gly Thr Glu Lys Leu Ile Glu Thr Tyr
            660                 665                 670

Phe Ser Lys Asn Tyr Gln Asp Tyr
        675                 680

<210> SEQ ID NO 227
<211> LENGTH: 1569
<212> TYPE: DNA
<213> ORGANISM: Artificial Sequence
<220> FEATURE:
<223> OTHER INFORMATION: delta Y-MSPe-synthetic gene comprising
      nucleotides coding for SEQ ID NOs: 10, 22, 23, 26-29, 31-33,
      36-39, 40-45 and restriction sites as depicted in Fig 7.

<400> SEQUENCE: 227
gaattcgcta gcgtggggtg gtatcgcccg ccattctctc gtgtggttca tctctaccgc      60
aatggcaagg accaagatgg ctcatatcgc ggtcgcacag agctgctgaa agatgctatt     120
ggtgagggca aggtgactct ccgtatccgc aatgtacgtt tctcagatga aggtggtaga     180
tccgatgaaa acccggtagt ccacttcttc aagaacattg tgacgcctcg cacaccaccg     240
ccgtcgcagg gctcggctca aagggtttc aagggcgtcg atgcccaggg cacgcttttcc    300 aaaatttta gctgtctgg cacgcttttcc aaaatttta gctgggtgg ccgcgatagt       360 cgctctggct caccgatggc tcgtcgcggt tcccagcgcc acggttccaa gtacctggcc     420
acagcaagca ctatggacca tgcccgtcat ggcttcctct ctagttccaa ggggctgtgg     480
gccgactgcg tcatggccac ggggctgtac cactgcaagc cgctggtgga catcctcatc     540
ctgccgggct acgtgggctc tccgacctgc cgcaagctgg atgagctggg ctccaagggg     600
ctgtgggccg actgcgtcat ggccacgggg ctgtaccact gcggttcagc cattttactg     660
ctgctgactg ttcttccgtg catccgtatg ggccaggagc aggttccaa ccgtttctac      720 tacactgcgg gctctagctc cccgactcat gcgaagagtg cccacgtaat gcagaaaaac     780
cagaagtaca gcgaacactt cagcattcac tgctgcccgc cgttcacctt cctcaattcc    840
aagaaggaga ttggctctca gaagaaagag gaggactgga tctgctgcgc ctgccagaag    900
```

-continued

```
acccgcacca gccgccgtgc caagtctcct cagcgcccga agggctctaa gcaacagccg    960
cgcagcagcc cactccgtgg gccaggcgct agtcgtggtg ggtcctcccg tgccaagccg   1020
cctcagcgcc caaagcaaca gcctgctgcg ccgccggcgg tgctcgagga ctacaagacc   1080
accatctgcg gcaagggcct gagcgcaacg gtaacagggg ccagaagggg gtcacagaag   1140
gggcgcggtt cccgtggcca acatcaagct cattctttgg agcgcgtgtg tcattgtttg   1200
ggcaaatggc taggccatcc ggacaagggc tcggtgtaca tttacttcaa cacctggacc   1260
acctgccagt ctattgcctt cccgagcaag acctctgcca gtatcggcag tctctgtggc   1320
agcaagacct ctgccagtat cggcagtctc tgtgctgatg cccgcatgta tggtgttggc   1380
tctattgcct tcccgagcaa gacctctgcc agtattggca gtctctgtgc tgatgcccgc   1440
atgtatggct cggcttttcc ctgcaaggtt tgtggctcca accttctgtc catctgcaaa   1500
acagcggagt tccaaatgac cttccacctg tttattgctg catttggatc atgagcggcc   1560
gcaagctta                                                           1569
```

<210> SEQ ID NO 228
<211> LENGTH: 517
<212> TYPE: PRT
<213> ORGANISM: Artificial Sequence
<220> FEATURE:
<223> OTHER INFORMATION: Polypeptide expressed by the DNA of SEQ ID NO: 227

<400> SEQUENCE: 228

```
Glu Phe Ala Ser Val Gly Trp Tyr Arg Pro Phe Ser Arg Val Val
1               5                   10                  15

His Leu Tyr Arg Asn Gly Lys Asp Gln Asp Gly Ser Tyr Arg Gly Arg
            20                  25                  30

Thr Glu Leu Leu Lys Asp Ala Ile Gly Glu Gly Lys Val Thr Leu Arg
        35                  40                  45

Ile Arg Asn Val Arg Phe Ser Asp Glu Gly Gly Arg Ser Asp Glu Asn
    50                  55                  60

Pro Val Val His Phe Phe Lys Asn Ile Val Thr Pro Arg Thr Pro Pro
65                  70                  75                  80

Pro Ser Gln Gly Ser Ala His Lys Gly Phe Lys Gly Val Asp Ala Gln
                85                  90                  95

Gly Thr Leu Ser Lys Ile Phe Lys Leu Ser Gly Thr Leu Ser Lys Ile
            100                 105                 110

Phe Lys Leu Gly Gly Arg Asp Ser Arg Ser Gly Ser Pro Met Ala Arg
        115                 120                 125

Arg Gly Ser Gln Arg His Gly Ser Lys Tyr Leu Ala Thr Ala Ser Thr
    130                 135                 140

Met Asp His Ala Arg His Gly Phe Leu Ser Ser Ser Lys Gly Leu Trp
145                 150                 155                 160

Ala Asp Cys Val Met Ala Thr Gly Leu Tyr His Cys Lys Pro Leu Val
                165                 170                 175

Asp Ile Leu Ile Leu Pro Gly Tyr Val Gly Ser Pro Thr Cys Arg Lys
            180                 185                 190

Leu Asp Glu Leu Gly Ser Lys Gly Leu Trp Ala Asp Cys Val Met Ala
        195                 200                 205

Thr Gly Leu Tyr His Cys Gly Ser Ala Ile Leu Leu Leu Thr Val
    210                 215                 220

Leu Pro Cys Ile Arg Met Gly Gln Gln Pro Gly Ser Asn Arg Phe Tyr
225                 230                 235                 240
```

```
Tyr Thr Ala Gly Ser Ser Pro Thr His Ala Lys Ser Ala His Val
                245                 250                 255

Met Gln Lys Asn Gln Lys Tyr Ser Glu His Phe Ser Ile His Cys Cys
        260                 265                 270

Pro Pro Phe Thr Phe Leu Asn Ser Lys Lys Glu Ile Gly Ser Gln Lys
        275                 280                 285

Lys Glu Glu Asp Trp Ile Cys Cys Ala Cys Gln Leu Thr Arg Thr Ser
        290                 295                 300

Arg Arg Ala Lys Ser Pro Gln Arg Pro Lys Gly Ser Lys Gln Gln Pro
305                 310                 315                 320

Arg Ser Ser Pro Leu Arg Gly Pro Gly Ala Ser Arg Gly Gly Ser Ser
                325                 330                 335

Arg Ala Lys Pro Pro Gln Arg Pro Lys Gln Gln Pro Ala Ala Pro Pro
                340                 345                 350

Ala Val Leu Glu Asp Tyr Lys Thr Thr Ile Cys Gly Lys Gly Leu Ser
                355                 360                 365

Ala Thr Val Thr Gly Gly Gln Lys Gly Ser Gln Lys Gly Arg Gly Ser
                370                 375                 380

Arg Gly Gln His Gln Ala His Ser Leu Glu Arg Val Cys His Cys Leu
385                 390                 395                 400

Gly Lys Trp Leu Gly His Pro Asp Lys Gly Ser Val Tyr Ile Tyr Phe
                405                 410                 415

Asn Thr Trp Thr Thr Cys Gln Ser Ile Ala Phe Pro Ser Lys Thr Ser
                420                 425                 430

Ala Ser Ile Gly Ser Leu Cys Gly Ser Lys Thr Ser Ala Ser Ile Gly
                435                 440                 445

Ser Leu Cys Ala Asp Ala Arg Met Tyr Gly Val Gly Ser Ile Ala Phe
450                 455                 460

Pro Ser Lys Thr Ser Ala Ser Ile Gly Ser Leu Cys Ala Asp Ala Arg
465                 470                 475                 480

Met Tyr Gly Ser Ala Phe Pro Gly Lys Val Cys Gly Ser Asn Leu Leu
                485                 490                 495

Ser Ile Cys Lys Thr Ala Glu Phe Gln Met Thr Phe His Leu Phe Ile
                500                 505                 510

Ala Ala Phe Gly Ser
            515

<210> SEQ ID NO 229
<211> LENGTH: 939
<212> TYPE: PRT
<213> ORGANISM: Artificial Sequence
<220> FEATURE:
<223> OTHER INFORMATION: Polypeptide exrpessed by the DNA of SEQ ID NO:
      92

<400> SEQUENCE: 229

Glu Phe Ala Ser Val Gly Trp Tyr Arg Pro Ala Phe Ser Arg Val Val
1               5                   10                  15

Ala Leu Tyr Arg Asn Gly Lys Asp Gln Asp Gly Ser Val Gly Trp Tyr
                20                  25                  30

Arg Pro Pro Phe Ser Ala Val Val His Leu Tyr Arg Asn Gly Lys Gly
            35                  40                  45

Ser Tyr Arg Gly Arg Thr Glu Leu Leu Ala Asp Ala Ile Gly Glu Gly
        50                  55                  60

Lys Ala Thr Leu Arg Ile Ala Asn Val Arg Phe Ser Asp Glu Gly Gly
65                  70                  75                  80
```

```
Ser Gly Glu Gly Lys Val Ala Leu Arg Ile Arg Ala Val Arg Phe Ser
            85                  90                  95
Asp Glu Gly Gly Phe Arg Ser Gly Pro Arg His Arg Ile Ala Ala Leu
            100                 105                 110
Val Gly Asp Glu Val Glu Leu Ala Ser Arg Ile Ser Pro Gly Lys Asn
            115                 120                 125
Ala Gly Ser Leu His Arg Arg Leu Ala Gly Gln Ala Leu Glu Glu Leu
            130                 135                 140
Arg Asn Pro Phe Gly Ser Asp Glu Asn Pro Val His Phe Phe Ala
145                 150                 155                 160
Asn Ile Val Thr Pro Arg Thr Pro Pro Ser Gln Gly Ser Glu Asn
                    165                 170                 175
Pro Val Val Ala Phe Phe Lys Asn Ile Ala Thr Pro Arg Thr Pro Pro
                180                 185                 190
Pro Ser Gln Gly Ser Ala His Lys Gly Phe Lys Gly Val Ala Ala Gln
                195                 200                 205
Gly Thr Leu Ser Lys Ile Phe Lys Leu Gly Ser Gly Thr Leu Ser Lys
            210                 215                 220
Ile Ala Lys Leu Gly Gly Arg Ala Ser Arg Ser Gly Ser Pro Met Ala
225                 230                 235                 240
Arg Arg Gly Ser Ser Ala His Lys Gly Phe Ala Gly Val Asp Ala Gln
                245                 250                 255
Gly Ala Leu Ser Lys Ile Phe Lys Leu Gly Ser Gln Arg His Gly
            260                 265                 270
Ser Ala Tyr Leu Ala Thr Ala Ser Thr Met Asp Ala Ala Arg His Gly
            275                 280                 285
Phe Leu Ser Arg Arg His Gly Phe Leu Pro Arg His Arg Ala Thr Gly
            290                 295                 300
Ile Leu Asp Ser Ile Gly Arg Phe Phe Gly Ser Gly Phe Leu Pro Arg
305                 310                 315                 320
His Ala Asp Thr Gly Ile Leu Asp Ser Ile Gly Arg Phe Phe Thr Ser
                    325                 330                 335
Ser Lys Gly Leu Ala Ala Asp Cys Val Ala Ala Thr Gly Leu Tyr Ala
            340                 345                 350
Cys Lys Pro Leu Ala Asp Ile Leu Ile Leu Pro Gly Tyr Val Gly Ser
            355                 360                 365
Pro Thr Cys Arg Lys Leu Ala Glu Leu Gly Ser Lys Gly Leu Ala Ala
            370                 375                 380
Asp Cys Val Ala Ala Thr Gly Leu Tyr Ala Cys Gly Ser Thr Ser Arg
385                 390                 395                 400
Lys Leu Ala Glu Leu Gly Ser Ala Gly Leu Trp Ala Ala Cys Val Met
                405                 410                 415
Ala Thr Gly Leu Tyr His Cys Gly Ser Ala Ile Leu Leu Leu Thr
                420                 425                 430
Val Leu Ala Ser Ile Arg Met Gly Gln Glu Pro Gly Ser Asn Arg Phe
            435                 440                 445
Tyr Tyr Thr Ala Gly Ser Ala Ser Pro Thr His Ala Ala Ser Ala His
            450                 455                 460
Val Gly Ser Thr Ala Gly Ser Ser Ser Pro Thr Ala Ala Leu Ser Ala
465                 470                 475                 480
His Val Met His Trp Ile Gly Val Ile Val Thr Ser Ala Asn Asp
                    485                 490                 495
Trp Val Val Thr Ser Gly Tyr Thr Ile Pro Gly Ser Val Leu Leu Ile
                500                 505                 510
```

```
Leu Leu Ala Ala Cys Ala Leu Val Ala Thr Ile Trp Phe Ala Val Cys
            515                 520                 525

Ala His Arg Glu Thr Thr Ile Leu Gln Lys Asn Gln Lys Tyr Ser Ala
            530                 535                 540

His Phe Ser Ile His Cys Cys Pro Ala Thr Phe Leu Asn Ser Lys
545                 550                 555                 560

Lys Glu Ile Gly Ser Lys Glu Glu Asp Trp Ala Cys Cys Ala Ser
                565                 570                 575

Gln Ala Thr Arg Thr Ser Arg Ala Lys Ser Pro Gln Arg Pro Lys
            580                 585                 590

Gly Ser Lys Gln Gln Pro Arg Ser Pro Leu Ala Gly Pro Gly Ala
            595                 600                 605

Ser Arg Gly Gly Ser Arg Ala Lys Ser Pro Gln Arg Pro Ala Gln Gln
            610                 615                 620

Pro Ala Ala Pro Pro Ala Val Leu Glu Asp Tyr Lys Thr Thr Ile Ser
625                 630                 635                 640

Gly Ala Gly Leu Ser Ala Thr Val Thr Gly Gly Gln Lys Gly Ser Asp
            645                 650                 655

Tyr Lys Thr Thr Ile Ser Gly Lys Gly Ala Ser Ala Thr Val Thr Gly
            660                 665                 670

Gly Gln Lys Gly Ser Gln Lys Gly Arg Gly Ser Arg Gly Gln Ala Gln
            675                 680                 685

Ala His Ser Ala Glu Arg Val Cys His Cys Leu Gly Lys Ala Leu Gly
            690                 695                 700

His Pro Asp Lys Gly Ser Val Tyr Ile Tyr Phe Asn Thr Trp Thr Ala
705                 710                 715                 720

Ser Gln Ser Ile Ala Phe Pro Ser Ala Thr Ser Ala Ser Ile Gly Ser
                725                 730                 735

Leu Ser Gly Ser Lys Thr Ser Ala Ser Ile Gly Ser Ala Ser Ala Asp
            740                 745                 750

Ala Arg Met Tyr Gly Val Gly Ser Ile Tyr Phe Asn Thr Ala Thr Thr
            755                 760                 765

Ser Gln Ser Ala Ala Phe Pro Ser Lys Ala Ser Ala Ser Ile Gly Ser
            770                 775                 780

Ser Ala Ala Phe Pro Ser Lys Ala Ser Ala Ser Ile Ala Ser Leu Ser
785                 790                 795                 800

Ala Asp Ala Arg Met Tyr Gly Ser Gln Ser Ile Ala Phe Ala Ser Lys
                805                 810                 815

Thr Ser Ala Ser Ile Ala Ser Leu Ser Ala Asp Gly Ser Ala Phe Pro
            820                 825                 830

Gly Lys Val Cys Gly Ser Ala Leu Leu Ser Ile Cys Lys Thr Ala Glu
            835                 840                 845

Phe Gln Met Gly Ser Ile Ser Lys Thr Ala Glu Phe Gln Ala Thr Phe
            850                 855                 860

His Leu Phe Ile Ala Ala Phe Gly Ser Ala Phe Pro Val Lys Ala Cys
865                 870                 875                 880

Gly Ser Asn Ala Leu Ser Ile Cys Lys Thr Ala Glu Phe Gln Met Thr
            885                 890                 895

Gly Ser Thr Tyr Asn Phe Ala Val Leu Lys Leu Ala Gly Arg Gly Thr
            900                 905                 910

Lys Phe Gly Ser Gly His Glu Ala Leu Thr Gly Thr Glu Ala Leu Ile
            915                 920                 925

Glu Thr Tyr Phe Ser Lys Asn Tyr Gln Asp Tyr
```

<210> SEQ ID NO 230
<211> LENGTH: 754
<212> TYPE: PRT
<213> ORGANISM: Artificial Sequence
<220> FEATURE:
<223> OTHER INFORMATION: Polypeptide expressed by the DNA of SEQ ID NO: 93
<220> FEATURE:
<221> NAME/KEY: DOMAIN
<222> LOCATION: (1)..(754)
<223> OTHER INFORMATION:

<400> SEQUENCE: 230

```
Glu Phe Ala Ser Val Gly Trp Tyr Arg Pro Ala Phe Ser Arg Val Val
1               5                   10                  15

Ala Leu Tyr Arg Asn Gly Lys Asp Gln Asp Gly Ser Val Gly Trp Tyr
            20                  25                  30

Arg Pro Pro Phe Ser Ala Val Val His Leu Tyr Arg Asn Gly Lys Gly
        35                  40                  45

Ser Tyr Arg Gly Arg Thr Glu Leu Leu Ala Asp Ala Ile Gly Glu Gly
    50                  55                  60

Lys Ala Thr Leu Arg Ile Ala Asn Val Arg Phe Ser Asp Glu Gly Gly
65                  70                  75                  80

Ser Gly Glu Gly Lys Val Ala Leu Arg Ile Arg Ala Val Arg Phe Ser
                85                  90                  95

Asp Glu Gly Gly Phe Arg Ser Asp Glu Asn Pro Val Val His Phe Phe
            100                 105                 110

Ala Asn Ile Val Thr Pro Arg Thr Pro Pro Ser Gln Gly Ser Glu
        115                 120                 125

Asn Pro Val Val Ala Phe Phe Lys Asn Ile Ala Thr Pro Arg Thr Pro
    130                 135                 140

Pro Pro Ser Gln Gly Ser Ala His Lys Gly Phe Lys Gly Val Ala Ala
145                 150                 155                 160

Gln Gly Thr Leu Ser Lys Ile Phe Lys Leu Gly Ser Gly Thr Leu Ser
                165                 170                 175

Lys Ile Ala Lys Leu Gly Gly Arg Ala Ser Arg Ser Gly Ser Pro Met
            180                 185                 190

Ala Arg Arg Gly Ser Ser Ala His Lys Gly Phe Ala Gly Val Asp Ala
        195                 200                 205

Gln Gly Ala Leu Ser Lys Ile Phe Lys Leu Gly Gly Ser Gln Arg His
    210                 215                 220

Gly Ser Ala Tyr Leu Ala Thr Ala Ser Thr Met Asp Ala Ala Arg His
225                 230                 235                 240

Gly Phe Leu Ser Ser Ser Lys Gly Leu Ala Ala Asp Cys Val Ala Ala
                245                 250                 255

Thr Gly Leu Tyr Ala Cys Lys Pro Leu Ala Asp Ile Leu Ile Leu Pro
            260                 265                 270

Gly Tyr Val Gly Ser Pro Thr Cys Arg Lys Leu Ala Glu Leu Gly Ser
        275                 280                 285

Lys Gly Leu Ala Ala Asp Cys Val Ala Ala Thr Gly Leu Tyr Ala Cys
    290                 295                 300

Gly Ser Thr Ser Arg Lys Leu Ala Glu Leu Gly Ser Ala Gly Leu Trp
305                 310                 315                 320

Ala Ala Cys Val Met Ala Thr Gly Leu Tyr His Cys Gly Ser Ala Ile
                325                 330                 335
```

-continued

```
Leu Leu Leu Leu Thr Val Leu Ala Ser Ile Arg Met Gly Gln Glu Pro
            340                 345                 350

Gly Ser Asn Arg Phe Tyr Tyr Thr Ala Gly Ser Ala Ser Pro Thr His
        355                 360                 365

Ala Ala Ser Ala His Val Gly Ser Thr Ala Gly Ser Ser Ser Pro Thr
    370                 375                 380

Ala Ala Lys Ser Ala His Val Met Gln Lys Asn Gln Lys Tyr Ser Ala
385                 390                 395                 400

His Phe Ser Ile His Cys Cys Pro Ala Thr Phe Leu Asn Ser Lys
                405                 410                 415

Lys Glu Ile Gly Ser Lys Glu Glu Asp Trp Ala Cys Cys Ala Ser
            420                 425                 430

Gln Ala Thr Arg Thr Ser Ala Arg Ala Lys Ser Pro Gln Arg Pro Lys
        435                 440                 445

Gly Ser Lys Gln Gln Pro Arg Ser Ser Pro Leu Ala Gly Pro Gly Ala
    450                 455                 460

Ser Arg Gly Gly Ser Arg Ala Lys Ser Pro Gln Arg Pro Ala Gln Gln
465                 470                 475                 480

Pro Ala Ala Pro Pro Ala Val Leu Glu Asp Tyr Lys Thr Thr Ile Ser
                485                 490                 495

Gly Ala Gly Leu Ser Ala Thr Val Thr Gly Gly Gln Lys Gly Ser Asp
            500                 505                 510

Tyr Lys Thr Thr Ile Ser Gly Lys Gly Ala Ser Ala Thr Val Thr Gly
        515                 520                 525

Gly Gln Lys Gly Ser Gln Lys Gly Arg Gly Ser Arg Gly Gln Ala Gln
    530                 535                 540

Ala His Ser Ala Glu Arg Val Cys His Cys Leu Gly Lys Ala Leu Gly
545                 550                 555                 560

His Pro Asp Lys Gly Ser Val Tyr Ile Tyr Phe Asn Thr Trp Thr Ala
                565                 570                 575

Ser Gln Ser Ile Ala Phe Pro Ser Ala Thr Ser Ala Ser Ile Gly Ser
            580                 585                 590

Leu Ser Gly Ser Lys Thr Ser Ala Ser Ile Gly Ser Ala Ser Ala Asp
        595                 600                 605

Ala Arg Met Tyr Gly Val Gly Ser Ile Tyr Phe Asn Thr Ala Thr Thr
    610                 615                 620

Ser Gln Ser Ala Ala Phe Pro Ser Lys Ala Ser Ala Ser Ile Gly Ser
625                 630                 635                 640

Ser Ala Ala Phe Pro Ser Lys Ala Ser Ala Ser Ile Ala Ser Leu Ser
                645                 650                 655

Ala Asp Ala Arg Met Tyr Gly Ser Gln Ser Ile Ala Phe Ala Ser Lys
            660                 665                 670

Thr Ser Ala Ser Ile Ala Ser Leu Ser Ala Asp Gly Ser Ala Phe Pro
        675                 680                 685

Gly Lys Val Cys Gly Ser Ala Leu Leu Ser Ile Cys Lys Thr Ala Glu
    690                 695                 700

Phe Gln Met Gly Ser Ile Ser Lys Thr Ala Glu Phe Gln Ala Thr Phe
705                 710                 715                 720

His Leu Phe Ile Ala Ala Phe Gly Ser Ala Phe Pro Val Lys Ala Cys
                725                 730                 735

Gly Ser Asn Ala Leu Ser Ile Cys Lys Thr Ala Glu Phe Gln Met Thr
            740                 745                 750

Gly Ser
```

```
<210> SEQ ID NO 231
<211> LENGTH: 16
<212> TYPE: PRT
<213> ORGANISM: Artificial Sequence
<220> FEATURE:
<223> OTHER INFORMATION: Synthetic peptide containing sequence 37-52 of
      MOG.
<220> FEATURE:
<221> NAME/KEY: DOMAIN
<222> LOCATION: (1)..(16)
<223> OTHER INFORMATION:

<400> SEQUENCE: 231

Val Gly Trp Tyr Arg Pro Pro Phe Ser Arg Val Val His Leu Tyr Arg
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: The peptide of SEQ ID NO:231 in which the
      residue at position 8 was replaced by Ala.
<220> FEATURE:
<221> NAME/KEY: DOMAIN
<222> LOCATION: (1)..(16)
<223> OTHER INFORMATION:

<400> SEQUENCE: 232

Val Gly Trp Tyr Arg Pro Pro Ala Ser Arg Val Val His Leu Tyr Arg
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: The peptide of SEQ ID NO:231 in which the
      residue at position 5 was replaced by Gln.
<220> FEATURE:
<221> NAME/KEY: DOMAIN
<222> LOCATION: (1)..(16)
<223> OTHER INFORMATION:

<400> SEQUENCE: 233

Val Gly Trp Tyr Gln Pro Pro Phe Ser Arg Val Val His Leu Tyr Arg
1               5                   10                  15

<210> SEQ ID NO 234
<211> LENGTH: 21
<212> TYPE: PRT
<213> ORGANISM: Artificial Sequence
<220> FEATURE:
<223> OTHER INFORMATION: Synthetic peptide containing sequence 35-55 of
      MOG.
<220> FEATURE:
<221> NAME/KEY: DOMAIN
<222> LOCATION: (1)..(21)
<223> OTHER INFORMATION:

<400> SEQUENCE: 234

Met Glu Val Gly Trp Tyr Arg Pro Pro Phe Ser Arg Val Val His Leu
1               5                   10                  15

Tyr Arg Asn Gly Lys
            20
```

The invention claimed is:

1. A synthetic polypeptide comprising amino acid sequences of at least one immunogenic epitope cluster (IEC) of at least two different human autoantigens related to multiple sclerosis (MS) selected from the group consisting of myelin-associated glycoprotein (MAG), myelin basic protein (MBP), myelin oligodendrocyte glycoprotein (MOG), myelin-oligodendrocytic basic protein (MOBP), oligodendrocyte-specific protein (OSP) and proteolipid protein (PLP), and wherein said IEC's are altered from their native sequence and are selected from the group consisting of the MOG-AL peptides of SEQ ID NOs: 48-53 and 232-233; the MBP-AL peptides of SEQ ID NOs: 54-61; the OSP-AL peptides of SEQ ID NOs: 62-69; the MOBP-AL peptides of SEQ ID NOs: 70-73; and the PLP-AL peptides of SEQ ID NOs: 74-86.

2. A synthetic polypeptide according to claim 1, wherein said at least one IEC of each of said at least two autoantigens is a polypeptide having at least two polypeptides selected from the group consisting of shMOG-AL (SEQ ID NO:166), shMBP-AL (SEQ ID NO:179), shOSP-AL (SEQ ID NO:194), shMOBP-AL (SEQ ID NO:203), and shPLP-AL (SEQ ID NO:224).

3. A synthetic polypeptide according to claim 2, selected from the group consisting of the polypeptides Y-MSP-AL (SEQ ID NO:229) and ΔY-MSP-AL (SEQ ID NO:230).

4. A pharmaceutical composition, comprising a polypeptide according to claim 1, and a pharmaceutically acceptable carrier.

* * * * *